(12) United States Patent
Longinotti-Buitoni et al.

(10) Patent No.: US 11,013,275 B2
(45) Date of Patent: **\*May 25, 2021**

(54) FLEXIBLE FABRIC RIBBON CONNECTORS FOR GARMENTS WITH SENSORS AND ELECTRONICS

(71) Applicant: L.I.F.E. Corporation S.A., Luxembourg (LU)

(72) Inventors: Gianluigi Longinotti-Buitoni, Haute-Nendaz (CH); Andrea Aliverti, Como (IT); Fabrizio Pallai, Milan (IT)

(73) Assignee: L.I.F.E. Corporation S.A., Luxembourg (LU)

( \* ) Notice: Subject to any disclaimer, the term of this patent is extended or adjusted under 35 U.S.C. 154(b) by 0 days.

This patent is subject to a terminal disclaimer.

(21) Appl. No.: 16/875,700

(22) Filed: May 15, 2020

(65) Prior Publication Data

US 2020/0323285 A1    Oct. 15, 2020

Related U.S. Application Data

(63) Continuation of application No. 15/877,378, filed on Jan. 22, 2018, now Pat. No. 10,653,190, which is a
(Continued)

(51) Int. Cl.
*H01R 33/00*     (2006.01)
*A41D 1/00*      (2018.01)
(Continued)

(52) U.S. Cl.
CPC ............. *A41D 1/005* (2013.01); *A41B 1/08* (2013.01); *A42B 1/046* (2013.01); *A61B 5/0205* (2013.01);
(Continued)

(58) Field of Classification Search
CPC .... A41D 1/005; A61B 5/0205; A61B 5/6804; A61B 5/04004; A61B 5/0402;
(Continued)

(56) References Cited

U.S. PATENT DOCUMENTS 3,591,526 A   7/1971   Kawashima
3,793,716 A   2/1974   Smith Johannsen
(Continued)

FOREIGN PATENT DOCUMENTS

CN   1294504 A   5/2001
CN   1985761 A   12/2006
(Continued)

OTHER PUBLICATIONS

Aliverti et al.; Compartmental analysis of breathing in the supine and prone positions by, optoelectronic plethysmography; Ann Biomed Eng; 29(1):60-70; Jan. 2001.
(Continued)

*Primary Examiner* — Yuriy Semenenko
(74) *Attorney, Agent, or Firm* — Shay Glenn LLP

(57) ABSTRACT

Elastic electrical connectors that may be incorporated into a garment to connect multiple electrical components in the garment. These electrical connectors are typically long strips of fabric substrate to which wires are attached along a length of one side in a sinusoidal or zig-zag pattern. The connector may also include an adhesive coating on one side to secure it to a fabric. The wires are electrically insulated, which may be a thermoremovable insulation (e.g., a polyurethane having a melting point of <400° C.). The wires may be attached to the surface of the fabric strip by a stitch at each peak and trough of the sinusoidal or zig-zag pattern with a length between peak and trough stitches between about 1 mm and 15 mm.

20 Claims, 49 Drawing Sheets

Related U.S. Application Data continuation-in-part of application No. PCT/IB2016/001146, filed on Jul. 20, 2016, and a continuation-in-part of application No. 15/813,073, filed on Nov. 14, 2017, now Pat. No. 10,045,439, which is a continuation of application No. 15/324,152, filed as application No. PCT/IB2015/001802 on Jul. 14, 2015, now Pat. No. 9,817,440, which is a continuation-in-part of application No. 14/612,060, filed on Feb. 2, 2015, now Pat. No. 9,986,771, and a continuation-in-part of application No. 14/331,185, filed on Jul. 14, 2014, now Pat. No. 8,945,328, which is a continuation-in-part of application No. 14/023,830, filed on Sep. 11, 2013, now Pat. No. 9,282,893, said application No. 14/612,060 is a continuation of application No. 14/331,185, filed on Jul. 14, 2014, now Pat. No. 8,945,328.

(60) Provisional application No. 62/194,731, filed on Jul. 20, 2015, provisional application No. 61/950,782, filed on Mar. 10, 2014, provisional application No. 61/862,936, filed on Aug. 6, 2013, provisional application No. 61/699,440, filed on Sep. 11, 2012.

(51) Int. Cl.
*A61B 5/00* (2006.01)
*A61B 5/0205* (2006.01)
*A41B 1/08* (2006.01)
*A42B 1/046* (2021.01)
*H01R 33/92* (2006.01)
*A61B 5/30* (2021.01)
*A61B 5/318* (2021.01)

(52) U.S. Cl.
CPC ............ *A61B 5/6804* (2013.01); *H01R 33/92* (2013.01); *A61B 5/30* (2021.01); *A61B 5/318* (2021.01); *A61B 5/4806* (2013.01); *A61B 2562/222* (2013.01)

(58) Field of Classification Search
CPC . A61B 5/4806; A61B 2562/222; A42B 1/046; A41B 1/08; H01R 33/92
See application file for complete search history.

(56) References Cited

U.S. PATENT DOCUMENTS

| | | | |
|---|---|---|---|
| 4,624,817 A | 11/1986 | Gusack et al. | |
| 4,710,981 A | 12/1987 | Sanchez | |
| 4,823,240 A | 4/1989 | Shenker | |
| 4,867,166 A | 9/1989 | Axelgaard et al. | |
| 5,036,865 A | 8/1991 | Keaton | |
| 5,111,818 A | 5/1992 | Suzuki et al. | |
| 5,148,002 A | 9/1992 | Kuo et al. | |
| 5,163,006 A | 11/1992 | Deziel | |
| 5,241,300 A | 8/1993 | Bushmann | |
| 5,280,265 A | 1/1994 | Kramer et al. | |
| 5,352,315 A | 10/1994 | Carrier et al. | |
| 5,379,461 A | 1/1995 | Wilmers | |
| 5,395,508 A | 3/1995 | Jolly et al. | |
| 5,557,263 A | 9/1996 | Fisher et al. | |
| 5,581,492 A | 12/1996 | Janik | |
| 5,635,909 A | 6/1997 | Cole | |
| 5,678,448 A | 10/1997 | Fullen et al. | |
| 5,694,645 A | 12/1997 | Triplette | |
| 5,749,365 A | 5/1998 | Magill | |
| 5,802,607 A | 9/1998 | Triplette | |
| 5,824,996 A | 10/1998 | Kochman et al. | |
| 5,845,644 A | 12/1998 | Hughes et al. | |
| 5,853,005 A | 12/1998 | Scanlon | |
| 5,865,740 A | 2/1999 | Kelly et al. | |
| 5,903,222 A | 5/1999 | Kawarizadeh et al. | |
| 5,906,004 A | 5/1999 | Lebby et al. | |
| 5,912,653 A | 6/1999 | Fitch | |
| 5,921,674 A | 7/1999 | Koczi | |
| 5,984,063 A | 11/1999 | Wallace, III | |
| 6,016,476 A | 1/2000 | Maes et al. | |
| 6,019,877 A | 2/2000 | Dupelle et al. | |
| 6,024,575 A | 2/2000 | Ulrich | |
| 6,047,203 A | 4/2000 | Sackrier et al. | |
| 6,080,690 A | 6/2000 | Lebby et al. | |
| 6,097,297 A | 8/2000 | Fard | |
| 6,136,127 A | 10/2000 | De Bastiani | |
| 6,144,120 A | 11/2000 | Doi et al. | |
| 6,210,771 B1 | 4/2001 | Post et al. | |
| 6,232,879 B1 | 5/2001 | Tyren | |
| 6,259,399 B1 | 7/2001 | Krasner | |
| 6,319,015 B1 | 11/2001 | Faunce | |
| 6,325,066 B1 | 12/2001 | Hughes et al. | |
| 6,341,504 B1 * | 1/2002 | Istook | H05K 1/0283 66/172 E |
| 6,349,201 B1 | 2/2002 | Ford | |
| 6,415,176 B1 | 7/2002 | Scheirer et al. | |
| 6,436,064 B1 | 8/2002 | Kloecker | |
| 6,490,534 B1 | 12/2002 | Pfister | |
| 6,561,814 B2 | 5/2003 | Tilbury et al. | |
| 6,563,424 B1 | 5/2003 | Kaario | |
| 6,642,467 B2 | 11/2003 | Farringdon | |
| 6,668,380 B2 | 12/2003 | Marmaropolous et al. | |
| 6,713,733 B2 | 3/2004 | Kochman et al. | |
| 6,729,025 B2 | 5/2004 | Farrell et al. | |
| 6,792,124 B2 | 9/2004 | Tilbury et al. | |
| 6,801,140 B2 | 10/2004 | Mantyjarvi et al. | |
| 6,830,344 B2 | 12/2004 | Reho et al. | |
| 6,895,261 B1 | 5/2005 | Palamides | |
| 6,930,608 B2 | 8/2005 | Grajales et al. | |
| 6,968,075 B1 | 11/2005 | Chang | |
| 6,970,731 B1 | 11/2005 | Jayaraman et al. | |
| 6,982,115 B2 | 1/2006 | Poulos et al. | |
| 7,020,508 B2 | 3/2006 | Stivoric et al. | |
| 7,034,685 B2 | 4/2006 | Fabre et al. | |
| 7,161,084 B2 | 1/2007 | Sandbach | |
| 7,173,437 B2 | 2/2007 | Hervieux et al. | |
| 7,191,803 B2 | 3/2007 | Orr et al. | |
| 7,210,939 B2 | 5/2007 | Marmaropolous et al. | |
| 7,211,053 B2 | 5/2007 | Marmaropolous et al. | |
| 7,230,610 B2 | 6/2007 | Jung et al. | |
| 7,248,756 B2 | 7/2007 | Ebbesen et al. | |
| 7,250,547 B1 | 7/2007 | Hofmeister et al. | |
| 7,299,034 B2 | 11/2007 | Kates | |
| 7,299,964 B2 | 11/2007 | Jayaraman et al. | |
| 7,319,895 B2 | 1/2008 | Klefstad-Sillonville et al. | |
| 7,320,947 B2 | 1/2008 | Child et al. | |
| 7,321,785 B2 | 1/2008 | Harris | |
| 7,324,841 B2 | 1/2008 | Reho et al. | |
| 7,344,379 B2 | 3/2008 | Marmaropolous et al. | |
| 7,348,645 B2 | 3/2008 | Xu | |
| 1,365,031 A1 | 4/2008 | Swallow et al. | |
| 7,377,133 B2 | 5/2008 | Sandbach et al. | |
| 7,388,166 B2 | 6/2008 | Marmaropolous et al. | |
| 7,429,959 B2 | 9/2008 | Gerder et al. | |
| 7,448,874 B2 | 11/2008 | Willis | |
| 7,476,104 B2 | 1/2009 | Marmaropolous et al. | |
| 7,559,768 B2 | 7/2009 | Marmaropolous et al. | |
| 7,578,195 B2 | 8/2009 | DeAngelis et al. | |
| 7,616,112 B2 | 11/2009 | Miller, III | |
| 7,645,220 B2 | 1/2010 | Hoffman et al. | |
| 7,665,288 B2 | 2/2010 | Karayianni et al. | |
| 7,683,643 B2 | 3/2010 | Qi et al. | |
| 7,712,373 B2 | 5/2010 | Nagle et al. | |
| 7,715,873 B1 | 5/2010 | Biere et al. | |
| 7,719,007 B2 | 5/2010 | Thompkins et al. | |
| 7,732,002 B2 | 6/2010 | Kodas et al. | |
| 7,753,685 B2 | 7/2010 | Lee et al. | |
| 7,753,845 B2 | 7/2010 | Gopinathan et al. | |
| 7,760,082 B2 | 7/2010 | Wong et al. | |
| 7,769,412 B1 | 8/2010 | Gailloux | |
| 7,770,473 B2 | 8/2010 | Von Lilienfeld-Toal et al. | |
| 7,779,656 B2 | 8/2010 | Dias et al. | |
| 7,783,334 B2 | 8/2010 | Nam et al. | |

(56) References Cited

U.S. PATENT DOCUMENTS

| | | | |
|---|---|---|---|
| 7,787,726 B2 | 8/2010 | Ten Eyck et al. |
| 7,849,888 B2 | 12/2010 | Karayianni et al. |
| 7,862,624 B2 | 1/2011 | Tran |
| 7,870,761 B2 | 1/2011 | Valentine et al. |
| 7,872,557 B2 | 1/2011 | Seibert |
| 7,878,030 B2 | 2/2011 | Burr |
| 7,880,607 B2 | 2/2011 | Olson et al. |
| 7,891,020 B2 | 2/2011 | Von Bluecher |
| 7,914,108 B2 | 3/2011 | Konno et al. |
| 7,933,554 B2 | 4/2011 | Hoyt et al. |
| 7,955,696 B2 | 6/2011 | Baikerikar et al. |
| 7,976,480 B2 | 7/2011 | Grajales et al. |
| 7,982,613 B2 | 7/2011 | Zheng |
| 7,983,876 B2 | 7/2011 | Vock et al. |
| 8,008,606 B2 | 8/2011 | Kaiserman et al. |
| 8,024,023 B2 | 9/2011 | Tolvanen |
| 8,032,199 B2 | 10/2011 | Linti et al. |
| 8,063,307 B2 | 11/2011 | Bukshpun et al. |
| 8,099,258 B2 | 1/2012 | Alten et al. |
| 8,140,143 B2 | 3/2012 | Picard et al. |
| 8,146,171 B2 | 4/2012 | Chung et al. |
| 8,162,857 B2 | 4/2012 | Lanfermann et al. |
| 8,186,231 B2 | 5/2012 | Graumann et al. |
| 8,214,008 B2 | 7/2012 | Hassonjee et al. |
| 8,228,202 B2 | 7/2012 | Buchner et al. |
| 8,253,586 B1 | 8/2012 | Matak |
| 8,262,217 B2 | 9/2012 | Furukawa |
| 8,263,215 B2 | 9/2012 | Burr et al. |
| 8,267,862 B2 | 9/2012 | Jeong et al. |
| 8,308,489 B2 | 11/2012 | Lee et al. |
| 8,331,097 B2 | 12/2012 | Yang et al. |
| 8,340,740 B2 | 12/2012 | Holzer et al. |
| 8,348,841 B2 | 1/2013 | Varadan |
| 8,348,865 B2 | 1/2013 | Jeong et al. |
| 8,362,882 B2 | 1/2013 | Heubel et al. |
| 8,373,079 B2 | 2/2013 | Walkington |
| 8,398,546 B2 | 3/2013 | Pacione et al. |
| 8,403,845 B2 | 3/2013 | Stivoric et al. |
| 8,416,579 B2 | 4/2013 | Biesheuvel et al. |
| 8,475,371 B2 | 7/2013 | Derchak et al. |
| 8,540,363 B2 | 9/2013 | Abreu |
| 8,739,397 B2 | 6/2014 | Nagata et al. |
| 8,798,708 B2 | 8/2014 | Tremblay |
| 8,862,431 B2 | 10/2014 | Hodge |
| 8,925,393 B2 | 1/2015 | Cannard et al. |
| 8,945,328 B2 | 2/2015 | Longinotti-Buitoni et al. |
| 8,948,839 B1 | 2/2015 | Longinotti-Buitoni et al. |
| 8,954,129 B1 | 2/2015 | Schlegel et al. |
| 9,282,893 B2 | 3/2016 | Longinotti-Buitoni et al. |
| 9,566,032 B2 | 2/2017 | Babaeizadeh et al. |
| 9,582,072 B2 | 2/2017 | Connor |
| 9,802,080 B2 | 10/2017 | Burich et al. |
| 9,817,440 B2 | 11/2017 | Longinotti-Buitoni et al. |
| 9,979,547 B2 | 5/2018 | Starner et al. |
| 10,039,354 B2 | 8/2018 | Van der Laan |
| 10,045,439 B2 | 8/2018 | Longinotti-Buitoni et al. |
| 10,154,791 B2 | 12/2018 | Longinotti-Buitoni et al. |
| 10,159,440 B2 | 12/2018 | Longinotti-Buitoni et al. |
| 10,201,310 B2 | 2/2019 | Mauri et al. |
| 10,258,092 B2 | 4/2019 | Longinotti-Buitoni et al. |
| 10,462,898 B2 | 10/2019 | Longinotti-Buitoni |
| 10,467,744 B2 | 11/2019 | Aliverti et al. |
| 10,653,190 B2 | 5/2020 | Longinotti-Buitoni et al. |
| 10,699,403 B2 | 6/2020 | Aliverti et al. |
| 10,736,213 B2 | 8/2020 | Longinotti-Buitoni et al. |
| 2002/0093515 A1 | 7/2002 | Fay et al. |
| 2003/0139692 A1 | 7/2003 | Barrey et al. |
| 2004/0115430 A1 | 6/2004 | Leonard |
| 2004/0249242 A1 | 12/2004 | Lau et al. |
| 2005/0022894 A1 | 2/2005 | Shannon |
| 2005/0029680 A1 | 2/2005 | Jung et al. |
| 2005/0058744 A1 | 3/2005 | Steinberg et al. |
| 2005/0067816 A1 | 3/2005 | Buckman |
| 2005/0107722 A1 | 5/2005 | Ozaki et al. |
| 2005/0228234 A1 | 10/2005 | Yang |
| 2006/0007059 A1 | 1/2006 | Bell |
| 2006/0062993 A1 | 3/2006 | Ogata et al. |
| 2006/0080182 A1 | 4/2006 | Thompson et al. |
| 2006/0124470 A1 | 6/2006 | Zama et al. |
| 2006/0139165 A1 | 6/2006 | Bader |
| 2006/0155182 A1 | 7/2006 | Mazzarolo |
| 2007/0000912 A1 | 1/2007 | Aisenbrey |
| 2007/0046720 A1 | 3/2007 | Konno et al. |
| 2007/0049842 A1 | 3/2007 | Hill et al. |
| 2007/0151312 A1 | 7/2007 | Bruce et al. |
| 2007/0153363 A1 | 7/2007 | Gruner |
| 2007/0177770 A1 | 8/2007 | Derchak et al. |
| 2007/0178716 A1 | 8/2007 | Glaser et al. |
| 2007/0202765 A1 | 8/2007 | Krans et al. |
| 2007/0293781 A1 | 12/2007 | Sims et al. |
| 2007/0299325 A1* | 12/2007 | Farrell .............. A61B 5/6805 600/301 |
| 2008/0045815 A1 | 2/2008 | Derchak et al. |
| 2008/0058744 A1 | 3/2008 | Tippey et al. |
| 2008/0064964 A1 | 3/2008 | Nagata et al. |
| 2008/0083720 A1 | 4/2008 | Gentile et al. |
| 2008/0083721 A1* | 4/2008 | Kaiserman ............. A43B 7/04 219/211 |
| 2008/0083740 A1 | 4/2008 | Kaiserman et al. |
| 2008/0171914 A1 | 7/2008 | Ouwerkerk et al. |
| 2008/0177168 A1 | 7/2008 | Callahan et al. |
| 2008/0234561 A1 | 9/2008 | Roesicke et al. |
| 2008/0241391 A1 | 10/2008 | Kim et al. |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0269629 A1 | 10/2008 | Reiner |
| 2008/0269652 A1 | 10/2008 | Reiner |
| 2008/0287769 A1 | 11/2008 | Kurzweil et al. |
| 2008/0287770 A1 | 11/2008 | Kurzweil et al. |
| 2008/0294019 A1 | 11/2008 | Tran |
| 2009/0012408 A1 | 1/2009 | Nagata et al. |
| 2009/0018410 A1 | 1/2009 | Coene et al. |
| 2009/0105795 A1 | 4/2009 | Minogue et al. |
| 2009/0112078 A1 | 4/2009 | Tabe |
| 2009/0157327 A1 | 6/2009 | Nissila |
| 2009/0227856 A1 | 9/2009 | Russell et al. |
| 2009/0281394 A1 | 11/2009 | Russell et al. |
| 2009/0286055 A1 | 11/2009 | Pourdeyhimi et al. |
| 2010/0004720 A1 | 1/2010 | Li et al. |
| 2010/0029598 A1 | 2/2010 | Kopitz et al. |
| 2010/0041974 A1 | 2/2010 | Ting et al. |
| 2010/0059274 A1 | 3/2010 | Ives et al. |
| 2010/0071205 A1 | 3/2010 | Grattmann et al. |
| 2010/0077528 A1 | 4/2010 | Lind et al. |
| 2010/0112195 A1 | 5/2010 | Kodas et al. |
| 2010/0113910 A1 | 5/2010 | Brauers et al. |
| 2010/0149567 A1 | 6/2010 | Kanazawa et al. |
| 2010/0176952 A1 | 7/2010 | Bajcsy et al. |
| 2010/0185062 A1 | 7/2010 | Salazar et al. |
| 2010/0185398 A1 | 7/2010 | Berns et al. |
| 2010/0194815 A1 | 8/2010 | Furukawa |
| 2010/0234715 A1 | 9/2010 | Shin et al. |
| 2010/0274100 A1 | 10/2010 | Behar et al. |
| 2010/0292598 A1 | 11/2010 | Roschk et al. |
| 2010/0309209 A1 | 12/2010 | Hodgins et al. |
| 2010/0312071 A1 | 12/2010 | Schenk |
| 2010/0324405 A1 | 12/2010 | Niemi et al. |
| 2011/0000412 A1 | 1/2011 | Chung et al. |
| 2011/0004088 A1 | 1/2011 | Grossman |
| 2011/0015498 A1 | 1/2011 | Mestrovic et al. |
| 2011/0028815 A1 | 2/2011 | Simpson et al. |
| 2011/0032103 A1 | 2/2011 | Bhat et al. |
| 2011/0042125 A1 | 2/2011 | Lee et al. |
| 2011/0074380 A1* | 3/2011 | Jeon ....................... D03D 13/00 323/318 |
| 2011/0087115 A1 | 4/2011 | Sackner et al. |
| 2011/0092795 A1 | 4/2011 | Derchak |
| 2011/0100683 A1 | 5/2011 | Bhattachaiya et al. |
| 2011/0102304 A1 | 5/2011 | Nelson |
| 2011/0115624 A1 | 5/2011 | Tran |
| 2011/0125064 A1 | 5/2011 | Shyr |
| 2011/0130643 A1 | 6/2011 | Derchak et al. |
| 2011/0144457 A1 | 6/2011 | Coulon |

(56) References Cited

U.S. PATENT DOCUMENTS

| | | |
|---|---|---|
| 2011/0181238 A1 | 7/2011 | Soar |
| 2011/0183068 A1 | 7/2011 | Yamakawa et al. |
| 2011/0184270 A1 | 7/2011 | Russell et al. |
| 2011/0259638 A1 | 10/2011 | Sherrill et al. |
| 2011/0267578 A1 | 11/2011 | Wilson |
| 2011/0277206 A1 | 11/2011 | Sokolowski |
| 2011/0283435 A1 | 11/2011 | Smith et al. |
| 2011/0288605 A1 | 11/2011 | Kaib et al. |
| 2012/0024833 A1 | 2/2012 | Klewer et al. |
| 2012/0029299 A1 | 2/2012 | Deremer et al. |
| 2012/0030935 A1 | 2/2012 | Slade et al. |
| 2012/0031431 A1 | 2/2012 | Carlson et al. |
| 2012/0035426 A1 | 2/2012 | Mielcarz et al. |
| 2012/0071039 A1 | 3/2012 | Debock et al. |
| 2012/0071793 A1 | 3/2012 | Gal |
| 2012/0078127 A1 | 3/2012 | McDonald et al. |
| 2012/0088986 A1 | 4/2012 | David et al. |
| 2012/0101357 A1 | 4/2012 | Hoskuldsson et al. |
| 2012/0118427 A1 | 5/2012 | Brookstein et al. |
| 2012/0127687 A1 | 5/2012 | Allee et al. |
| 2012/0136231 A1* | 5/2012 | Markel ............... A61B 5/6804 600/388 |
| 2012/0143093 A1 | 6/2012 | Stirling et al. |
| 2012/0144551 A1 | 6/2012 | Guldalian |
| 2012/0144561 A1 | 6/2012 | Begriche et al. |
| 2012/0144934 A1 | 6/2012 | Russell et al. |
| 2012/0146797 A1 | 6/2012 | Oskin et al. |
| 2012/0156933 A1 | 6/2012 | Kreger et al. |
| 2012/0158074 A1 | 6/2012 | Hall |
| 2012/0165645 A1 | 6/2012 | Russell et al. |
| 2012/0165717 A1 | 6/2012 | Al Khaburi |
| 2012/0184826 A1 | 7/2012 | Keenan et al. |
| 2012/0188158 A1 | 7/2012 | Tan et al. |
| 2012/0197224 A1 | 8/2012 | Chagger |
| 2012/0215076 A1 | 8/2012 | Yang et al. |
| 2012/0223833 A1 | 9/2012 | Thomas et al. |
| 2012/0233751 A1 | 9/2012 | Hexels |
| 2012/0238845 A1 | 9/2012 | Yang |
| 2012/0246795 A1 | 10/2012 | Scheffler et al. |
| 2012/0255166 A1 | 10/2012 | Kim et al. |
| 2012/0324616 A1 | 12/2012 | Hyde et al. |
| 2012/0330109 A1 | 12/2012 | Tran |
| 2013/0013331 A1 | 1/2013 | Horseman |
| 2013/0019372 A1 | 1/2013 | Esses |
| 2013/0019383 A1 | 1/2013 | Korkala et al. |
| 2013/0041272 A1 | 2/2013 | Guillen et al. |
| 2013/0053674 A1 | 2/2013 | Volker |
| 2013/0066168 A1 | 3/2013 | Yang et al. |
| 2013/0072777 A1 | 3/2013 | Tremblay |
| 2013/0077263 A1 | 3/2013 | Oleson et al. |
| 2013/0079860 A1 | 3/2013 | Besio |
| 2013/0144111 A1 | 6/2013 | Wang et al. |
| 2013/0179288 A1 | 7/2013 | Moses et al. |
| 2013/0211208 A1 | 8/2013 | Varadan |
| 2013/0212900 A1 | 8/2013 | Stewart |
| 2013/0231711 A1 | 9/2013 | Kalb |
| 2013/0244121 A1 | 9/2013 | Gogotsi et al. |
| 2013/0245423 A1 | 9/2013 | Derchak et al. |
| 2013/0281795 A1 | 10/2013 | Varadan |
| 2013/0314668 A1 | 11/2013 | Haddadi et al. |
| 2014/0061273 A1 | 3/2014 | Bullivant et al. |
| 2014/0100436 A1 | 4/2014 | Brunner et al. |
| 2014/0135593 A1 | 5/2014 | Jayalth et al. |
| 2014/0135602 A1 | 5/2014 | Lemke et al. |
| 2014/0172134 A1 | 6/2014 | Casillas et al. |
| 2014/0182880 A1 | 7/2014 | Simenhaus et al. |
| 2014/0206948 A1 | 7/2014 | Romem |
| 2014/0303470 A1 | 10/2014 | Tsukada et al. |
| 2014/0312027 A1 | 10/2014 | Augustine et al. |
| 2014/0352023 A1 | 12/2014 | Mordecai et al. |
| 2015/0143601 A1 | 5/2015 | Longinotti-Buitoni et al. |
| 2015/0289820 A1 | 10/2015 | Miller et al. |
| 2015/0342266 A1 | 12/2015 | Cooper et al. |
| 2016/0148531 A1 | 5/2016 | Bleich et al. |
| 2016/0253487 A1 | 9/2016 | Sarkar et al. |
| 2016/0262462 A1 | 9/2016 | Kawamura et al. |
| 2017/0084100 A1 | 3/2017 | Shibutani et al. |
| 2017/0112440 A1* | 4/2017 | Mauri ...................... A61B 5/11 |
| 2017/0319132 A1 | 11/2017 | Longinotti-Buitoni et al. |
| 2018/0004924 A1 | 1/2018 | Tieu et al. |
| 2018/0038041 A1 | 2/2018 | Longinotti-Buitoni et al. |
| 2018/0184735 A1 | 7/2018 | Longinotti-Buitoni et al. |
| 2018/0249767 A1* | 9/2018 | Begriche .............. A61B 5/0492 |
| 2018/0271441 A1 | 9/2018 | Dabby |
| 2018/0317814 A1* | 11/2018 | Nurkka ................ A61B 5/0806 |
| 2019/0133474 A1 | 5/2019 | Longinotti-Buitoni |
| 2019/0373963 A9* | 12/2019 | Longinotti-Buitoni ...................... H01R 33/92 |

FOREIGN PATENT DOCUMENTS

| | | |
|---|---|---|
| CN | 101108125 A | 1/2008 |
| CN | 101917903 A | 12/2010 |
| CN | 102970925 A | 3/2013 |
| EP | 1057923 A1 | 12/2000 |
| EP | 1335831 A1 | 8/2003 |
| EP | 1478249 A1 | 11/2004 |
| EP | 1509128 A1 | 3/2005 |
| EP | 1622512 A2 | 2/2006 |
| EP | 1709903 A1 | 10/2006 |
| EP | 1905112 A2 | 4/2008 |
| EP | 1907075 A2 | 4/2008 |
| EP | 1925718 A2 | 5/2008 |
| EP | 2025369 A2 | 2/2009 |
| EP | 2191737 A1 | 6/2010 |
| EP | 2196142 A1 | 6/2010 |
| EP | 2217145 A1 | 8/2010 |
| EP | 2314744 A2 | 4/2011 |
| EP | 3037036 A1 | 6/2016 |
| JP | H02-139608 U | 11/1990 |
| JP | H04-338452 A | 11/1992 |
| JP | H05-77208 U | 10/1993 |
| JP | 2008229084 A | 10/2008 |
| JP | 2009228161 A | 10/2009 |
| JP | 2011521122 A | 7/2011 |
| JP | 2012526204 A | 10/2012 |
| JP | 2012214968 A | 11/2012 |
| JP | 2014505529 A | 3/2014 |
| JP | 2015206130 A | 11/2015 |
| WO | WO90/06189 A1 | 6/1990 |
| WO | WO00/16493 A1 | 3/2000 |
| WO | WO01/01855 A1 | 1/2001 |
| WO | WO03/000015 A2 | 1/2003 |
| WO | WO03/060449 A1 | 7/2003 |
| WO | WO2004/076731 A1 | 9/2004 |
| WO | WO2004/107831 A2 | 12/2004 |
| WO | WO2005/032447 A2 | 4/2005 |
| WO | WO2005/067796 A1 | 7/2005 |
| WO | WO2005/096133 A1 | 10/2005 |
| WO | WO2006/064447 A2 | 6/2006 |
| WO | WO2006/102538 A2 | 9/2006 |
| WO | WO2007/056557 A1 | 5/2007 |
| WO | WO2008/137046 A1 | 11/2008 |
| WO | WO2008/153786 A1 | 12/2008 |
| WO | WO2009/040696 A1 | 4/2009 |
| WO | WO2009/112281 A1 | 9/2009 |
| WO | WO2010/038176 A1 | 4/2010 |
| WO | WO2010/044018 A1 | 4/2010 |
| WO | WO2010/058346 A2 | 5/2010 |
| WO | WO2010/085671 A1 | 7/2010 |
| WO | WO2010/085688 A1 | 7/2010 |
| WO | WO2010/096907 A1 | 9/2010 |
| WO | WO2010/120945 A1 | 10/2010 |
| WO | WO2010/139087 A1 | 12/2010 |
| WO | WO2011/092620 A1 | 8/2011 |
| WO | WO2011/131235 A1 | 10/2011 |
| WO | WO2011/156095 A2 | 12/2011 |
| WO | WO2012/011068 A1 | 1/2012 |
| WO | WO2012/060524 A1 | 5/2012 |
| WO | WO2012/066056 A1 | 5/2012 |
| WO | WO2012/073076 A1 | 6/2012 |
| WO | WO2012/073230 A1 | 6/2012 |
| WO | WO2012/083066 A2 | 6/2012 |
| WO | WO2012/104484 A1 | 8/2012 |

(56) References Cited

FOREIGN PATENT DOCUMENTS

| WO | WO2012/110954 A1 | 8/2012 |
|---|---|---|
| WO | WO2012/112186 A1 | 8/2012 |
| WO | WO2012/113014 A1 | 8/2012 |
| WO | WO2012/140079 A1 | 10/2012 |
| WO | WO2012/140522 A2 | 10/2012 |
| WO | WO2012/168836 A2 | 12/2012 |
| WO | WO2012/176193 A1 | 12/2012 |
| WO | WO2014/025430 A2 | 2/2014 |
| WO | WO2014/075682 A1 | 5/2014 |
| WO | WO2014/204323 A1 | 12/2014 |
| WO | WO2015/103620 A1 | 7/2015 |
| WO | WO2015/138515 A1 | 9/2015 |
| WO | WO2016/035350 A1 | 3/2016 |

OTHER PUBLICATIONS

Babchenko et al.; Fiber optic sensor for the measurement of respiratory chest circumference changes; J Biomed Opt; 4(2):224-229; Apr. 1999.

Cala et al.; Chest wall and lung volume estimation by optical reflectance motion analysis; J Appl Physiol; 81(6);2680-2689; Dec. 1996.

Chadha et al.; Validation of respiratory inductive plethysmography using different calibration procedures; Am Rev Respir Dis; 125:644-649; Jun. 1982.

Chen et al.; Color structured light system of chest wall motion measurement for respiratory volume evaluation; J Biomed Opt; 15(2):026013; Mar.-Apr. 2010.

Chourabi et al.; Understanding smart cities: An integrative framework; 45th Hawii International Conference on System Sciences; pp. 2289-2297; Jan. 4, 2012.

D'Angelo et al.; A system for respiratory motion detection using optical fibers embedded into textiles; Conf Prof IEEE Med Biol Sac; 3694-3697; Aug. 2008.

Dodgson; Variation and extrema of human interpupillary distance; Prod. of SPIE: Stereoscopic Displays and Virtual Reality Systems XI; vol. 5291; pp. 36-46; Jan. 2004.

Ferrigno et al.; Three-dimensional optical analysis of chest wall motion; J Appl Physiol; 77(3):1224-1231; Sep. 1994.

Gramse et al.; Novel concept for a noninvasive cardiopulmonary monitor for infants: a pair of pajamas with an integrated sensor module; Ann Biomed Eng; 31(2):152-158; Feb. 2003.

Heilman et al.; Accuracy of the LifeShirt (Vivometrics) in the detection of cardiac rhythms; Biol Psychol; 75(3)300-305; Jul. 2007.

Hossain et al.; Human identity verification by using physiological and behavioural biometric traits; International Journal of Bioscience, Biochemistry and Bioinformatics; 1(3); pp. 199-205; Sep. 2011.

Kenyon et al.; Rib cage mechanics during quiet breathing and exercise in humans; J Appl Physiol; 83(4):1242-1255; Oct. 1997.

Konno et al.; Measurement of the separate volume changes of rib cage and abdomen during breathing; J Appl Physiol; 22(3):407-422; Mar. 1967.

Lafortuna et al.; A new instrument for the measurement of rib cage and abdomen circumference variation in respiration at rest and during exercise; Eur J App Physiol Occup Physiol; 71(2-3):259-265; Mar. 1995.

Milledge et al.; Inductive plethysmography—a new respiratory transducer; J Physiol; 267(1):4P-5P, May 1977.

Peacock et al.; Optical mapping of the thoracoabdominal wall; Thorax; 39(2):93-100; Feb. 1984.

Peacock et el., Optical measurement of the change in trunk volume with breathing, Bull Eur Physiopathol Respir; 21(2):125-129; Mar.-Apr. 1985.

Pennock B.E.; Rib cage and abdominal piezoelectric film belts to measure ventilatory airflow; J Clin Monit; 6(4):276-283, Oct. 1990.

Purao et al.; Modeling citizen-centric services in smart cities; 32nd. International Conference on Conceptual Modeling; Hong Kong; pp. 438-445; (8 pages, retrieved from the internet at https://icity.smu.edu.sg/sites/icity.smu.edu.sg/files/publications/Modeling-Citizen-centric-Services-in-Smart-Cities_ER2013.pdf); Nov. 11-13, 2013.

Sackner et al.; Calibration of respiratory inductive plethysmograph during natural breathing; J App Physiol; 66(1):410-420; Jan. 1989.

Saumarez; Automated optical measurements of human torso surface movements during freathing; J. Appl. Physiol.; 60(2); pp. 702-709; Feb. 1986.

Zimmerman et al.; Postural changes in rib cage and abdominal volume-motion coefficients and their effect on the calibration of a respiratory inductance plethysmograph; Am Rev Respir Dis; 127(2):209-214; Feb. 1983.

Qian Junhao; Constitution of Conductive Ink; New Ink Printing Technology; Chinese Light Industry Press; pp. 64-66; (English Summary Included); Jan. 2002.

Yan Suzhai et al.; 984. Conductive materials can be divided into what kind of two major categories according to material properties; 1000 Questions on Screen Printing Ink; Printing Industry Press; pp. 241-242; (English Summary Included); Apr. 2005.

Pang et al.; Review on fabric-based sensor; Industrial Textiles; Issue 6, (English Summary Included); (year of pub. sufficiently earlier than effective US filing date and any foreign priority date); 2012.

Aliverti et al.; U.S. Appl. No. 16/914,093 entiteld Systems and methods to automatically determine garment fit,: filed Jun. 26, 2020.

\* cited by examiner

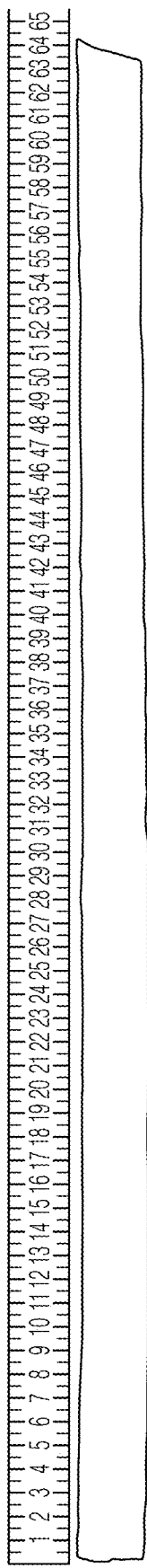
FIG. 13
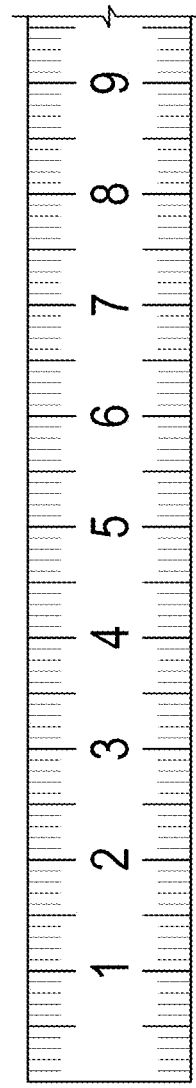
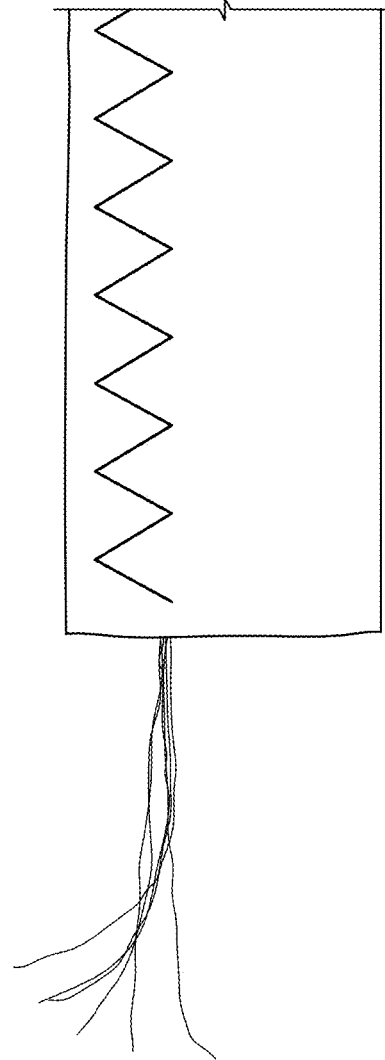
FIG. 14

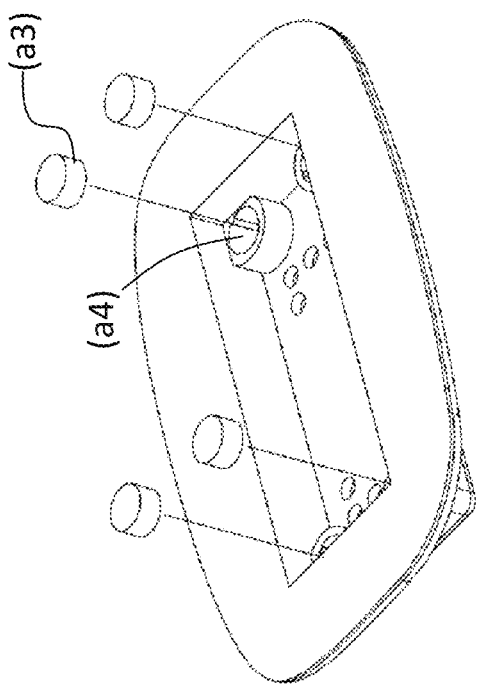
FIG. 23
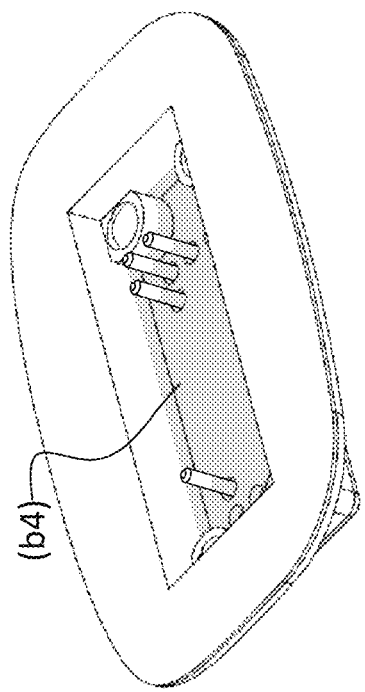
FIG. 25
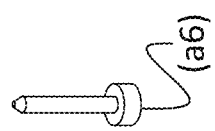
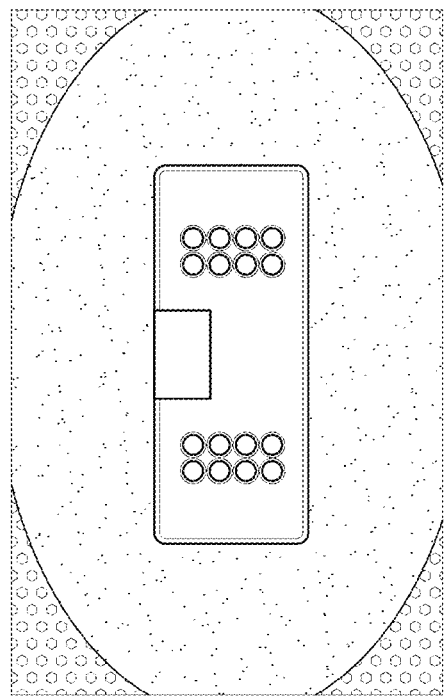
FIG. 22
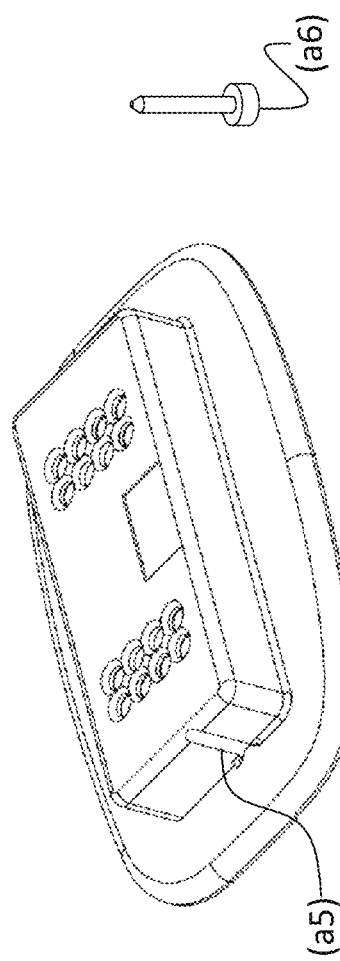
FIG. 24

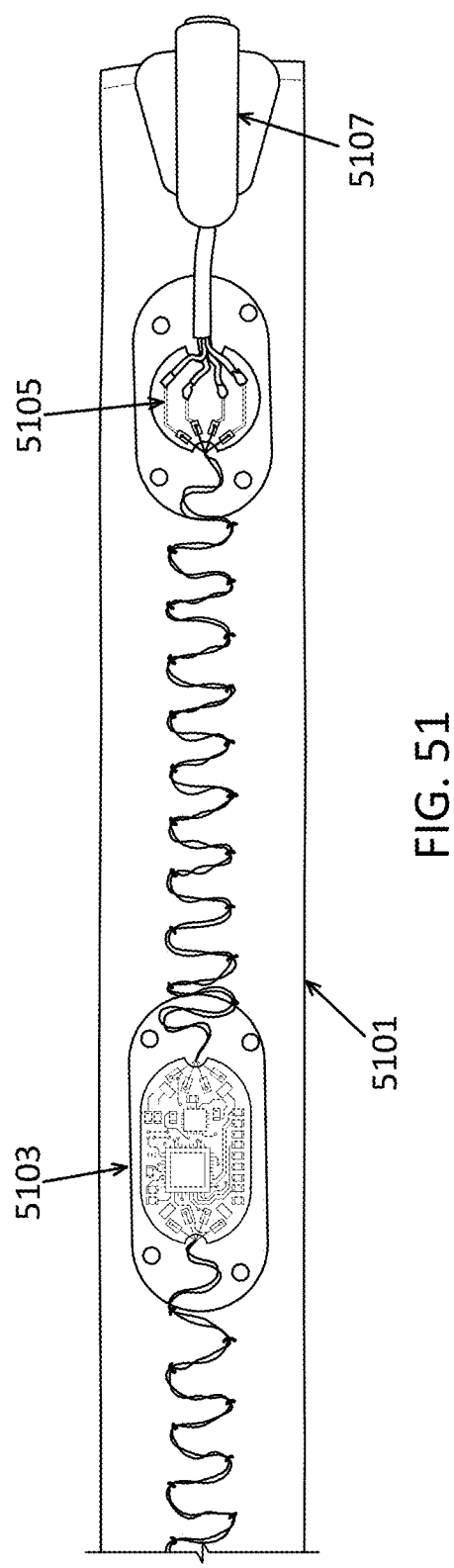

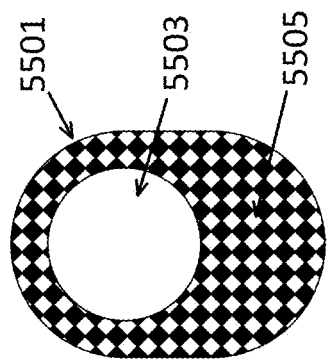
FIG. 55A
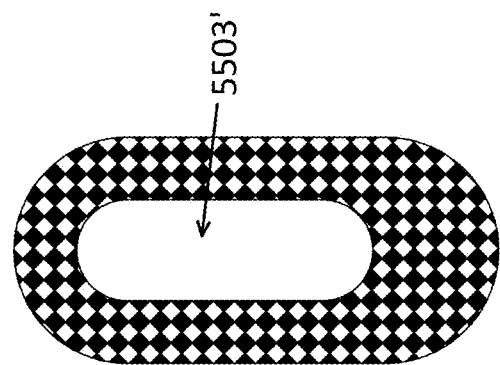
FIG. 55B
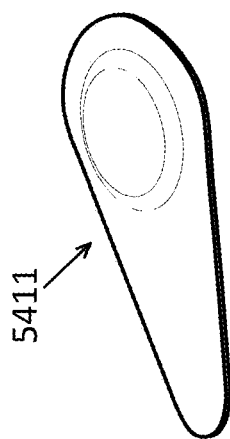
FIG. 54B
 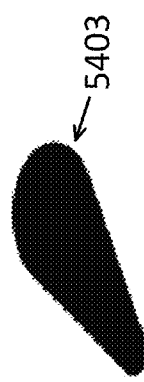 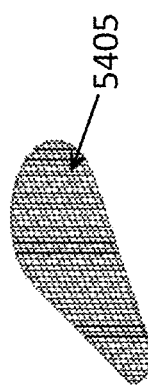  
FIG. 54A

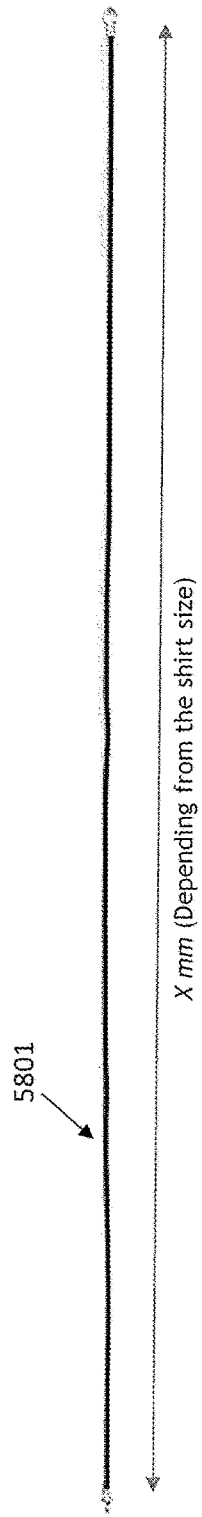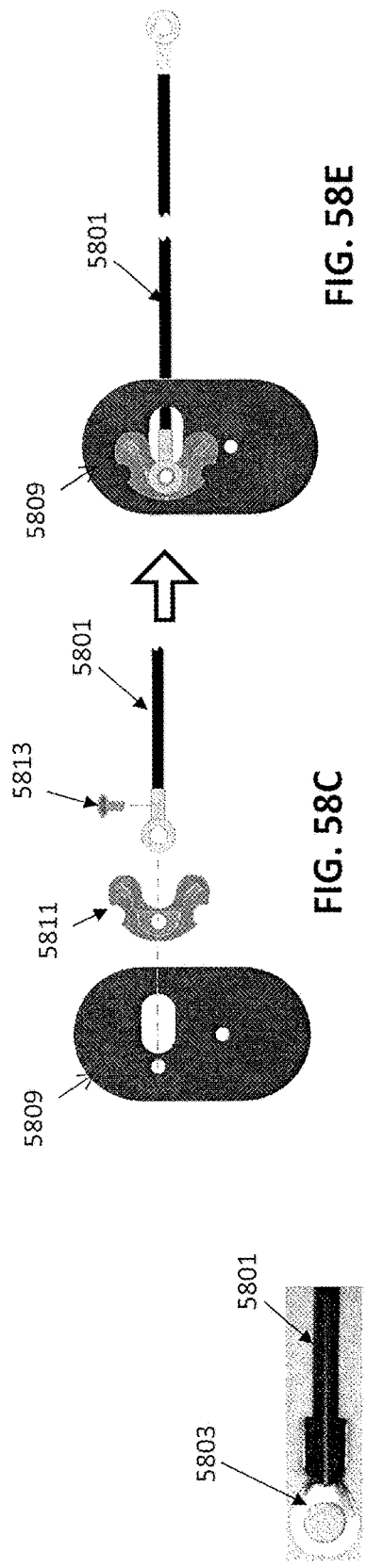

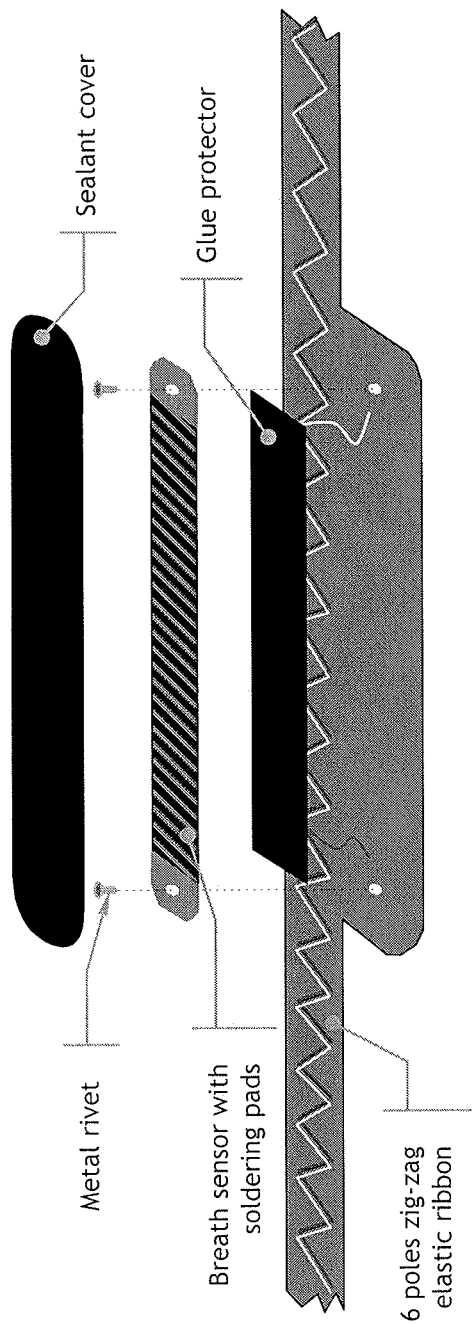

FLEXIBLE FABRIC RIBBON CONNECTORS FOR GARMENTS WITH SENSORS AND ELECTRONICS

CROSS REFERENCE TO RELATED APPLICATIONS

This application is a continuation of U.S. patent application Ser. No. 15/877,378, filed on Jan. 22, 2018, and titled "FLEXIBLE FABRIC RIBBON CONNECTORS FOR GARMENTS WITH SENSORS AND ELECTRONICS," which claims priority as a continuation-in-part of International Patent Application No. PCT/IB2016/001146, filed on Jul. 20, 2016, and titled "FLEXIBLE FABRIC RIBBON CONNECTORS FOR GARMENTS WITH SENSORS AND ELECTRONICS," which claims priority to U.S. Provisional Patent Application No. 62/194,731, titled "FLEXIBLE FABRIC RIBBON CONNECTORS FOR GARMENTS WITH SENSORS AND ELECTRONICS," and filed on Jul. 20, 2015.

This application is also a continuation-in-part of U.S. patent application Ser. No. 15/813,073, filed Nov. 14, 2017, titled "GARMENTS HAVING STRETCHABLE AND CONDUCTIVE INK," now U.S. Pat. No. 10,045,439, which is a continuation of U.S. patent application Ser. No. 15/324,152, filed Jan. 5, 2017, titled "GARMENTS HAVING STRETCHABLE AND CONDUCTIVE INK," now U.S. Pat. No. 9,817,440, which is a national phase application under 35 USC 371 of International Patent Application No. PCT/IB2015/001802, filed Jul. 14, 2015, titled "GARMENTS HAVING STRETCHABLE AND CONDUCTIVE INK," which is a continuation-in-part of U.S. patent application Ser. No. 14/331,185, filed Jul. 14, 2014, titled "METHODS OF MAKING GARMENTS HAVING STRETCHABLE AND CONDUCTIVE INK," now U.S. Pat. No. 8,945,328, which is a continuation-in-part of U.S. Pat. Ser. No. 14/023,830, filed Sep. 11, 2013, titled "WEARABLE COMMUNICATION PLATFORM," now U.S. Pat. No. 9,282,893, which claims the benefit of U.S. Provisional Patent Application No. 61/699,440, filed Sep. 11, 2012, titled "SMARTWEAR SYSTEM," and U.S. Provisional Patent Application No. 61/862,936, filed Aug. 6, 2013, and titled "WEARABLE COMMUNICATION PLATFORM."

U.S. patent application Ser. No. 14/331,185 claims the benefit of U.S. Provisional Patent Application No. 61/950,782, filed Mar. 10, 2014 and titled "PHYSIOLOGICAL MONITORING GARMENTS."

International Patent Application No. PCT/IB2015/001802 is also a continuation-in-part of U.S. patent application Ser. No. 14/612,060, filed Feb. 2, 2015, titled "GARMENTS HAVING STRETCHABLE AND CONDUCTIVE INK," now U.S. Pat. No. 9,986,771, which is a continuation of U.S. patent application Ser. No. 14/331,185, filed Jul. 14, 2014, titled "METHODS OF MAKING GARMENTS HAVING STRETCHABLE AND CONDUCTIVE INK," now U.S. Pat. No. 8,945,328

This application may be related to U.S. patent application Ser. No. 14/612,060, filed on Feb. 2, 2015 ("GARMENTS HAVING STRETCHABLE AND CONDUCTIVE INK"), which is a continuation of U.S. patent application Ser. No. 14/331,142 filed Jul. 14, 2014 ("COMPRESSION GARMETS HAVING STRETCHABLE AND CONDUCTIVE INK"). This application may also be related to U.S. patent application Ser. No. 14/644,180 filed Mar. 10, 2015 ("PHYSIOLOGICAL MONITORING GARMENTS"), which claims priority to U.S. Provisional Patent Application No. 62/097,560, filed on Dec. 29, 2015 ("STRETCHABLE, CONDUCTIVE TRACES AND METHODS OF MAKING AND USING SAME").

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The disclosure herein relates to electrical connectors for garments having multiple integrated electrical components (including sensors), and garments including them. In particular, this disclosure relates to strips of elastic electrical connectors that may be used to connect multiple electrical devices on a garment having integrated electrical devices.

BACKGROUND

In recent years the development of wearable electronics has dramatically expanded. Computers with ever-faster computer processors enabled faster communication with increased processing speed and improved analysis of vast quantities of data. In addition, sensor technology has also rapidly expanded how patients have been monitored, even by non-professionals. The development of various sensors enabled a variety of measurements to be taken and analyzed by a computer to generate useful information. The use of medical sensing technology in combination with various communications platforms may provide new and interesting ways for people, including patients, to be monitored or to monitor themselves and communicate the results of the monitoring with their physician or caregiver.

Cardiovascular and other health-related problems, including respiratory problems may be detected by monitoring a patient. Monitoring may allow early and effective intervention, and medical assistance may be obtained based on monitored physiological characteristics before a particular health issue becomes fatal. Unfortunately, most currently available cardiovascular and other types of health monitoring systems are cumbersome and inconvenient (e.g., impractical for everyday use) and in particular, are difficult or impractical to use for long-term monitoring, particularly in an unobtrusive manner.

Clothing that includes sensors have been previously suggested. See, e.g., US2007/0178716 to Glaser et al., which describes a "modular microelectronic-system" designed for use with wearable electronics. US2012/0071039 to Debock et al. describes interconnect and termination methodology fore-textiles that include a "conductive layer that includes conductors includes a terminal and a base separately provided from the terminal. The terminal has a mating end and a mounting end." US2005/0029680 to Jung et al. describes a method and apparatus for the integration of electronics in textiles. These wearable electronic garments are limited however, in their ability to comfortably and accurately link electronics (including sensors) on the garment.

It has been proposed that patient health parameters, including vital signs (such as ECG, respiration, blood oxygenation, heart rate, etc.) could be actively monitoring using one or more wearable monitors, however, to date such monitors have proven difficult to use and relatively inaccurate. Ideally such monitors could be unobtrusively worn by the subject (e.g., as part of a garment, jewelry, or the like). To date, the wearable electronics garments proposed all suffer from a number of deficits, including being uncomfortable, difficult to use and manufacture, and providing inaccurate results. For example, in applications such as US 2012/0136231, a number of individual electrodes are positioned on the garment and connected to a processor by woven conductive fibers or the like; although such garments "require . . . consistent and firm conductive contact with the subject's skin," in order to provide accurate readings, such designs require that the garment be restrictive in order to prevent movement of the garment (and thus sensors) contacting these skin regions. Such a configuration rapidly becomes uncomfortable, particularly in a garment that would ideally be worn for many hours or even days. In addition, even such tightly worn garments often move relative to the wearer (e.g., slip or ride up). Further, devices/garments such as those described in the prior art are difficult and expensive to manufacture, and are often rather "fragile", preventing robust usage and washing. Finally, such devices/garments typically do not allow processing of manual user input directly on the garment, but either relay entirely on passive monitoring, or require an interface of some sort (including off-garment interfaces).

The use of garments including one or more sensors that may sense biometric data have not found widespread use. In part, this may be because such garments may be limited in the kinds and versatility of the inputs that they accept, as well as limits in the comfort, and form factor of the garment. For example, sensors, and the leads providing power to and receiving signals from the sensors have not been fully integrated with the garment in a way that allows the garment to be flexible, attractive, practical, and above all, comfortable. For example, most such proposed garments have not been sufficiently stretchable. Finally, such proposed garments are also limited in the kind of data that they can receive, and how they process the received information.

What is needed are apparatuses (including garments) having multiple sensors that may be comfortably worn, yet provide relatively accurate and movement-insensitive measurements over a sustained period of time. It would also be beneficial to provide garments that can be easily and inexpensively manufactured.

In particular, what is needed are stretchable and conductive connectors that can be attached or applied onto a garment. These stretchable, conductive connectors may be used even with the most stretchable of fabrics, and/or with compression fabrics/compression garments, and moved through numerous stretch/relaxation cycles with the underlying fabric without breaking and while maintaining a stable electrical connection over time and use. The apparatuses, including devices and systems including them described herein may address some or all of the problems identified above.

SUMMARY OF THE DISCLOSURE

Described herein garments including integrated electronic sensors and methods of making and using them. In particular, the methods and apparatuses described herein may provide methods and apparatuses (systems, devices, etc.) for forming garments with wearable electronics that may be fabricated in a robust, efficient, and cost-effective manner. For example, described herein are strips of elastic electrical connectors that may be used to connect multiple electrical devices on a garment having integrated electrical devices (including sensors). These strips of elastic electrical connectors may be adhesively applied to a garment (or a fabric to forma garment) and may be comfortably worn while providing robust electrical connection.

For example, described herein are elastic electrical connector devices for incorporating into a garment to connect multiple electrical components in the garment. Such devices may include: an elongate strip of fabric substrate having a first side and a second side; a plurality of wires extending along a length of the first side of the elongate strip of fabric substrate in a sinusoidal or zig-zag pattern, wherein each of the wires is electrically insulated, and wherein the plurality of wires are attached to the first surface by a stitch at a peak and a trough of the sinusoidal or zig-zag pattern; and an adhesive coating the first side.

As used herein, a sinusoidal pattern is a curve that describes a repeating (or oscillating) pattern, and may broadly include zig-zag, saw-tooth, (e.g., triangular), smooth, or other repeating waves having a peak and a trough, where the peak and trough are connected by non-vertical paths (e.g., excluding purely square waveforms). Thus, in general the oscillating pattern of the wires in any of the apparatuses (e.g., devices, garments, etc.) described herein may be referred to as an oscillating pattern having a series of longitudinally repeating peaks and troughs, wherein each peak is followed by an adjacent trough and separated by a longitudinal distance (e.g., greater than 0.1 mm, 0.5 mm, 1 mm, etc.) and separated by a vertical distance (e.g., amplitude).

Any of these elastic electrical connector device for incorporating into a garment to connect multiple electrical components in the garment may include: an elongate strip of fabric substrate having a first side with a length; a bundle of wires that are twisted together extending along the length of the first side of the elongate strip of fabric substrate in a sinusoidal or zig-zag pattern, wherein each of the wires is electrically insulated with a thermoremovable insulator, and wherein the bundle of wires are attached to the first surface by a stitch at each peak and trough of the sinusoidal or zig-zag pattern wherein the length between peak and trough stitches is between about 1 mm and 15 mm; and an adhesive coating the first side.

The elastic electrical connector may be a generally thin strip (e.g., ribbon, band, etc.) that may be relatively thin and narrow. For example, the strip may have a maximum thickness of less than about 2 mm (e.g., less than about 1.9 mm, less than about 1.8 mm, less than about 1.7 mm, less than about 1.6 mm, less than about 1.5 mm, less than about 1.4 mm, less than about 1.3 mm, less than about 1.2 mm, less than about 1.1 mm, less than about 1.0 mm, etc.).

The elastic electrical connector may be any appropriate length and thickness. For example, the elastic electrical connector (the elongate strip of fabric substrate of the elastic electrical connector) may be between about 0.6 mm and about 3 cm wide, and greater than about 10 cm long. The length may extend for meters, including greater than 1 m, greater than 2 m, greater than 3 m, etc. the elastic electrical connector may be spooled up so that it may be cut to fit and conveniently used in a variety of fabrications.

The plurality of wires comprises a bundle of wires twisted together. In some variations, the plurality may be wires arranged in parallel. The plurality of wires generally includes between 2 and 20 (e.g., between 2 and 18, 2 and 17, 2 and 16, 2 and 15, 2 and 14, 2 and 13, 2 and 12, 2 and 11, 2 and 10, 2 and 9, 2 and 8, 2, etc.). In general, each of the wires is individually coded along its outer length, so that it may be distinguished from the other wires. For example, each wire may be a distinct color and/or pattern (e.g., printed on the outer visible surface of the wire. When the plurality is a bundle of wires, the wires are typically individually electrically insulated. Thus, the bundle is not encased or enclosed as a group, so that they can be individually separated out from the bundle, through pulled out of the stich or attachment holding them to the substrate fabric.

As mentioned, each wire is typically individually electrically insulated, and this electrical insulation may be configured as a thermoremovable insulator that can be removed by application of a relatively low heat, as applied during soldering. Thus, the wires may not need to be separately stripped or removed of the insulation. For example, the wires may be made of a copper wire that is electrically insulated with a polyurethane.

The wires are typically attached on one side of the substrate (fabric) in a sinusoidal pattern, or more specifically a zig-zag pattern. For example, the sinusoid or zig-zag pattern may have an amplitude (from peak to trough, measured in a direction normal to the zig-zag pattern) that is from about 0.2 mm to 20 mm (e.g., from 0.5 mm to about 15 mm, etc.). The distance between the peak and trough measured along the sinusoidal (e.g., zig-zag) pattern, e.g., a length between peak and trough stitches, may be between about 0.5 mm and about 20 mm (e.g., between about 1 mm and 15 mm, etc.).

The elastic electrical connector typically has a relaxed configuration (e.g., unstretched) and a stretched configuration. The garment may be stretched up to about 100% (2×) or more (e.g., 200%, 300%, etc.) of its relaxed configuration without breaking one of the connecting wires.

In some variations, it is helpful that the wires (e.g., bundle of wires) are held to the garment by one or more stitches at the peak and trough of the sinusoidal pattern, as through stitches around the wires that pass through the substrate. This configuration may allow the stitches to act as eyelets that the wires may slide, while still maintaining the shape of the sinusoid.

In any of the elastic electrical connectors described herein the adhesive coating may be a relatively thin adhesive coating. For example, the adhesive coating may comprise a hot melt film having a low melting point. The adhesive coating may have a thickness of between 10 and 200 micrometers thick (e.g., 20 and 190, 30 and 180, 40 and 170, 50 and 160, 60 and 150, etc., or any thickness between 10 and 200 micrometers. The actual thickness may depend on the material, though thinner coatings are preferred. The adhesive is configured to secure the elastic electrical connector to the garment that it will form a part of. Thus, any appropriate garment-compatible (and somewhat elastic and/or flexible) adhesive may be used. For example, the adhesive coating comprises a hot melt film having a melting point of between about 130° C. and 200° C.

In any of these variations, the substrate fabric may be formed of the same fabric as the garment to which the elongate strip of fabric substrate is to be attached, including a stretchable fabric substrate. For example, the elongate strip of fabric substrate may comprise a polyamide/elastane blend fabric (e.g., 74% polyamide, 26% elastane).

Any of these devices (elastic electrical connectors) may include a removable backing on the first side covering the adhesive. The back may be paper (e.g., waxed paper), plastic, or the like, and may be peeled off to expose the adhesive.

Also described herein are elastic electrical connector device for incorporating into a garment to connect multiple electrical components in the garment, the device comprising: an elongate strip of fabric substrate having a first side and a second side; a plurality of wires extending along a length of the first side of the elongate strip of fabric substrate in a sinusoidal or zig-zag pattern, wherein each of the wires is electrically insulated, and wherein the plurality of wires are attached to the first surface; and an adhesive coating the first side.

Method of making these elastic electrical connectors are also described herein. A method of forming an elastic electrical connector that may be applied to a garment to connect multiple electrical components of the garment may include: attaching an elongate bundle of wires to a first surface of an elongate strip of fabric in a sinusoidal or zig-zag pattern comprising alternating peaks and troughs, wherein the wires are each electrically insulated, and wherein the bundle is attached to the first surface by at least one stitch at each peak and trough of the sinusoidal or zig-zag pattern, wherein the length between peak and trough stitches is between about 1 mm and 15 mm; applying an adhesive coating the first side; and covering the adhesive coating with a removable backing.

Also described herein are garments made using the elastic electrical connectors described herein. For example, a garment may include: a first fabric; a plurality of electrical components on the first fabric; and at least one elastic electrical connector comprising: an elongate strip of a second fabric substrate having a first side; a plurality of wires extending along a length of the first side of the elongate strip of fabric substrate in a sinusoidal or zig-zag pattern, wherein each of the wires is electrically insulated, and wherein the plurality of wires are attached to the first surface by a stitch at a peak and a trough of the sinusoidal or zig-zag pattern, and an adhesive coating the first side; wherein the each electrical component is connected to one or more wire in the at least one electrical connector. In general, the electrical components described herein that may be connected by the elastic electrical connectors may include any appropriate electrical component, and in particular (but not limited to) a sensor.

A method of forming a garment may include: adhesively attaching one or more elastic electrical connector to a first fabric, each elastic electrical connector comprising: an elongate strip of a second fabric substrate having a first side; a plurality of wires extending along a length of the first side of the elongate strip of fabric substrate in a sinusoidal or zig-zag pattern, wherein each of the wires is electrically insulated, and wherein the plurality of wires are attached to the first surface by a stitch at a peak and a trough of the sinusoidal or zig-zag pattern, and an adhesive coating the first side; and attaching a plurality of electrical components to the first fabric, wherein each electrical component is connected to at least one wire of the one or more elastic electrical connector.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 10A is a graph showing test results illustrating the voltage through wires of a flexible (fabric) connector having four wires, over repeated cycles of stretching (up to 3000 cycles). FIG. 10B graphically illustrates an example of a connector having six wires. FIG. 10C illustrates an example of a connector having 8 connectors.

FIG. 13 illustrates on elongate strip of fabric configured as an elastic electrical connector.

FIG. 14 shows an enlarged view of the proximal end of the elastic electrical connector device of FIG. 13, showing the ends of six insulated wires forming the wire bundle arranged in a zig-zag pattern along the length of the elastic electrical connector.

FIG. 19A shows the front (wearer-facing) surface, while FIG. 19B shows the back surface that will be attached to the garment. The sensor may be connected to a connector (e.g., a SPIDON as described herein) and then applied to the garment.

FIG. 22 illustrates an assembled SMS connector and housing attached to a fabric (garment).

FIG. 23 shows a top of an SMS housing.

FIG. 24 shows a bottom of an SMS housing.

FIG. 25 shows another view of a top of an SMS housing including an epoxy resin for waterproofing.

FIG. 31A shows different patterns of stitches, having different pitches and widths (angles); FIG. 40B shows an example of five parallel conductive threads that may connect to five different sensors. FIG. 40C shows an example of a single conductive thread (wire).

FIG. 51 illustrates an IMU and jack such as those shown in FIGS. 49 and 50 connected to an elastic connector as described herein.

FIG. 54A is an exploded view of one example of an electrode that may be included in any of the apparatuses described herein, including in any of the strips of material including wiring. This electrode may be configured, e.g., as an EEG, EOG, etc., electrode. FIG. 54B shows an assembled view of the embossed electrode without the cover.

FIG. 55A is an example of a fabric cover for an electrode (e.g., an ECG electrode) having a grip pattern. FIG. 55B is another example of a cover for a longer ECG electrode.

In FIG. 57, two vertical (and parallel) strips of breath sensors are included.

FIGS. 58A-58I illustrate one method of making a breath sensor using a silicone conductive cord.

FIG. 59 is an example of a method of forming another variation of a breath sensor from a plurality of flat layers.

DETAILED DESCRIPTION

Figure 1A:
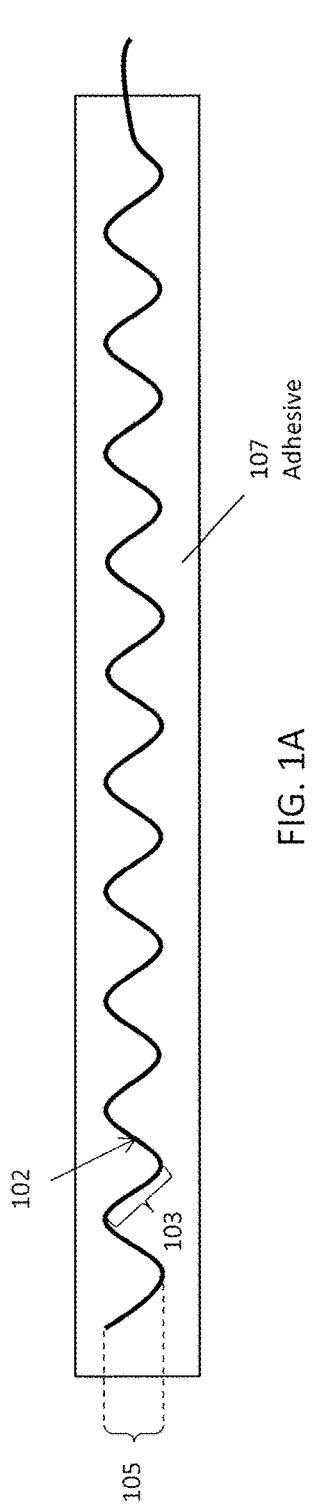
FIG. 1A is a schematic illustration of an elastic electrical connector device for incorporating into a garment to connect multiple electrical components in the garment, shown in a top view.

In general, descried herein are wearable electronic devices. Wearable electronics typically include garments that may be worn on a subject and include one (or more preferable, a plurality) of sensors that are configured to detect, process and relay biometric signals for monitoring the user; outputs (haptics, speakers, etc.) may also be included, and one or more processors may be included as well. A particular challenge for wearable electronics is sizing. Because the garments may be used by a variety of different body types, and because they may be comfortable for use through a variety of body movements, the garments must be configured to make robust and reliable contact with the subject's body in a predictable manner, even while being worn, stretched and otherwise manipulated by the wearer. In particular, described herein are methods and apparatuses (including devices, systems, garments, etc.) that form wearable electronics so that they may be easily fabricated and may make robust and reliable electrical contact with sensors on the garment, while positioning the sensors in a predefined location on the wearer's body.

For example, described herein are elastic electrical connector devices for incorporating into a garment to connect multiple electrical components in the garment, methods of making these elastic electrical connectors, garments including elastic electrical connectors and methods of making such garments.

An elastic electrical connector may be referred to herein as an elastic strip connector, a fabric strip connector, or the like. Generally, the elastic electrical connectors described herein may include a fabric substrate (e.g., cut or formed into an elongate strip of fabric substrate). This substrate may be elastic (e.g., it may be made of a stretchable fabric). A plurality of wires may be attached to one side of the fabric, and the plurality of wires may be attached in a sinusoidal (e.g., zig-zag) pattern along the length of the elastic electrical connector. For example, the elastic electrical connector may include a plurality of wires extending along a length of the first side of the elongate strip of fabric substrate in a sinusoidal or zig-zag pattern. The wires may be attached to the substrate by sewing or stitching. In some variations, the wires are attached by adhesive (instead of or in addition to stitching). For example, the plurality of wires may be attached to the first surface by one or more stitches at the peaks and troughs of the sinusoidal or zig-zag pattern.

The garments described herein may be worn by any appropriate user/subject/patient. As used herein the wearer may be referred to as a user, patient, or subject, or alternatively, "wearer," and may include human and non-human (e.g., animal) subjects.

In general, there may be spacing between the attachment points at the peak and troughs (e.g., between the stitches) holding the bundle of wires to the substrate in the sinusoidal or zig-zag pattern. This spacing may be greater than 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 20 mm, etc. (e.g., between about 1 mm and 15 mm); this spacing may be distance between durable attachment sites (e.g., stitches). The spacing between attachment points may along the length of the substrate may vary, or it may be constant. Leaving the bundle of wires (which may be twisted together) may make the wires easier to separate out for attachment to an electrical component as will be described below. Note that even in variations in which the wires are not referred to herein as attached, the wires of the elastic electrical connector may be considered as unattached, as the adhesive may not securely hold the wire(s) to the substrate between the peaks and troughs. In general, any of the variations described herein (unless otherwise specified) may include an adhesive on one or both sides of the elastic electrical connector, including the side to which the zig-zag/sinusoidal wires (wire bundle) is attached.

In some variations the adhesive may hold (or help hold) the plurality of wires or bundle of wires in the sinusoidal pattern as described. For example, the plurality of wires may be embedded within adhesive that holds (or helps hold) the wires in the sinusoidal (e.g., zig-zag, sawtooth, etc.) oscillating pattern yet allow individual wires to be removed from the adhesive and the substrate individually, e.g., by pulling, for cutting and attaching to an electrical device such as a sensor. In any of the variations including adhesive, the adhesive may help hold the plurality (e.g., bundle) of wires in the oscillating pattern along the substrate while still permitting individual wires to be removed from the side (e.g., back) of the substrate for attachment, leaving the other wires in the oscillating pattern. Thus, the adhesive strength (e.g., tensile or pull-off adhesive strength) of a wire held to the substrate (or within the substrate) may be relatively low, allowing it to be manually removed without damaging the individual wire or disrupting the oscillatory pattern of the other wires on the substrate.

Each of the wires of the elastic electrical connector may be electrically insulated. In particular, the insulation layer on the wire may be thermo-removable, so that just heating (e.g., by soldering, e.g., greater than 200 degrees C., greater than 250 degrees C., greater than 300 degrees C., greater than 350 degrees C., greater than 400 degrees C., etc.) may remove the insulation from the wire at the heated portion, leaving the rest of the wire(s) insulated.

Figure 1B:
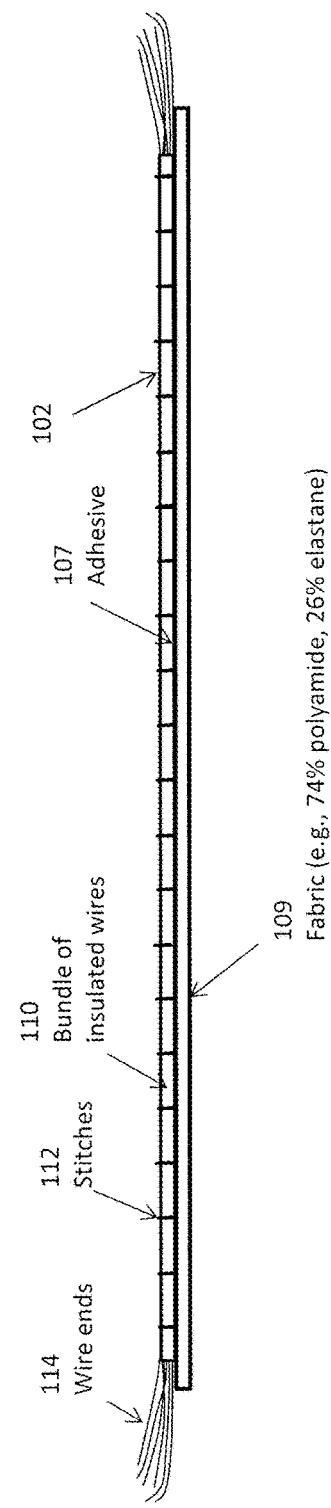
FIG. 1B is a side view of the electrical connector shown in FIG. 1A.

For example, FIG. 1 illustrates, schematically, one variation of an elastic electrical connector. In this example, the elastic electrical connector device includes a strip of elastic fabric 109, an adhesive 107, and a bundle of wires 102. Any number of wires (e.g., between 2 and 20, 2 and 19, 2 and 18, 2 and 17, 2 and 16, 2 and 15, 2 and 14, etc.) may be included in the connector device. In this example, the zig-zag/sinusoidal bundle of wires may have an amplitude 105 (from trough to peak) of between about 0.5 to 15 mm (or more, e.g., 17, 18, 19, 20, 21, 22, 23, 24, 25, etc., mm). The stitch length 103, or distance between trough and peak along the wire(s) may be between about 1 mm to 15 mm.

The electrical connectors described herein may allow deformation (elongation, twisting, curling, etc.) of the electrical connections. Shortly, this is achieved by embedding a bundle of electrical wire in a fabric sandwich held together by the thermo-adhesive. The thickness of the finished spidon may be important for wearable comfort. For example, the thickness applied may be between about 0.5 and 2 mm. (typically <2 mm).

Because of the arrangement of the zig-zag (sigmoidal) assembly may have material property advantages. For example, maximum elongation (which is dictated by the mechanical properties of the chosen substrate fabric) may increase. The geometry of the ZIG.ZAG pattern is optimized to ensure maximum elongation of the fabric in the long direction (Zig-zag direction) (i.e., the ZIG-ZAG is not the weak-link).

The amplitude and stitch-lengths of the patterns used to form the elastic electrical connector. For example, the device (e.g., elastic electrical connector) may be optimized to meet the above constraint and to support 3000 stress cycles, e.g., having a guaranteed elongation: of between about 80% to 400. The values for range of angles between the lines of wire extending between peak and trough of usually between 30 and 110 degrees.

The substrate used may be any appropriate substrate. For example the material used may be, e.g., Lycra, and other synthetic fibers. For example in some variations the fabric comprises a mixture of fabrics, such as a mixture of a synthetic (e.g., polyester) and another material (e.g. Lycra or elastin), e.g., around 25-40% of elastin or Lycra with the remainder being polyester. The fabric in some ways acts as a limiter, limiting the maximum stretch of connector to the maximum stretch of the fabric used, or less.

As mentioned, any appropriate glue (adhesive) may be applied to the back of the elastic electrical connector. For example, the adhesive may be applied to a thickness of between about 20 and 300 microns (e.g., between about 80-100 microns, between about 50-200 microns, between about 100-200 microns, etc.)

As will be described in more detail below, to connect a wire to an electrical component, the wire may be cut and removed from the bundle at the cut end so that it can be electrically connected. The wires may be coded (e.g., color/pattern coded), and the proper wire may be cut (e.g., with a scalpel or scissor) and then when soldered directly; the application of the solder (heat) may remove e.g., by evaporation, the insulation. In general, the wires in the bundle are not fused or enclosed together, but may be secured as a bungle only at the apexes (peaks and troughs) of the sinusoidal pattern, e.g., by a stitch. This may allow the wires to be individually separated and pulled out of the bundle (and out of the stitches holding the pattern, e.g., by pulling the cut end from the bundle, allowing them to be easily identified and attached to an electrical component, such as a sensor or PCB.

Figure 2:
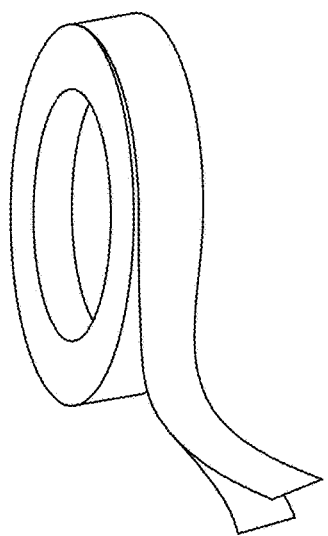
FIG. 2 illustrates a roll of elastic electrical connector such as the connector shown in FIG. 1A.

Overall, the strip of fabric forming the device may be cut into fabric strips of any length and width. E.g., strips may generally be between 3-4 cm widths (e.g., as thin as possible). Likewise, the length may be varied. In some examples (e.g., FIG. 2), a roll of elastic electrical connector may be made and cut to order during fabrication of the garments described herein.

This elastic electrical connectors may also be referred to as fabric ribbons or fabric ribbon connectors, and may include the conductive zig-zag (e.g., sinusoidal) enameled, twisted wires. The purpose of the elastic electrical connector is to deliver signals and electricity in every needed part of a garment. There are numerous advantages to this type of elastic electrical connector: every single wire/conductor can be easily connected to a sensor, an electrode or an electronic board without having to strip the wire's jacket, or remove the fabric protection or others. This is possible because the strand on enameled, twisted wires (composed from 2 to up to more than 8 wires) is sewed on the glued side of the ribbon and can be easily worked on (cut, stripped of protection, welded, attached, . . . ) before being thermally applied to the garment. Therefore only a single simple operation is needed in the production process: removing the cut wire's insulation so that it can be welded to electrodes, sensors or any electronic or electrical parts.

Moreover, this allows us to prepare the "harnesses" with all the required connections in advance, to test it and to then 'attach' it (the 'harness' or SPIDON assembly) to the garment in one single/efficient/low-cost operation much like is done in the car manufacturing for the electrical distribution. In contrast to other devices and methods for connecting electrical components on a wearable garment, the elastic electrical connectors described herein are relatively thin (e.g., less than 2 mm, less than 1.9 mm, less than 1.8 mm, less than 1.7 mm, less than 1.6 mm, less than 1.5 mm, etc.). In contrast, other connectors are too thick which may prevent the comfort needed in compression or tight clothes. Other connectors are also described as woven inside the ribbon, thus the connections can only be done at the beginning or at the end of the ribbons so many different ribbons are needed. Further, it may be very difficult and time consuming to cut the ribbon at the desired dimensions and strip out the wires without damaging them. In some cases the wires may not have insulation, thus they have to be sewed separately limiting the ribbon width to the number of wires, moreover the ribbon risks to generate short-circuit effects when in contact with sweat or rain.

The fabrication of the conductive ribbon as described herein may start with the coupling of a thermo adhesive film with the fabric: the two coupled materials pass then between two hot metal rollers that melt the glue onto the fabric side. A fabric reel normally has a dimension of 140 cm width and a length of about 70 m: after the glue coupling process, the reel can be cut in smaller reels sized to the desired width (FIG. 1). The ribbon reels come out with fabric on the external side and glue (protected with silicone-paper film) on the internal side.

Figure 3:
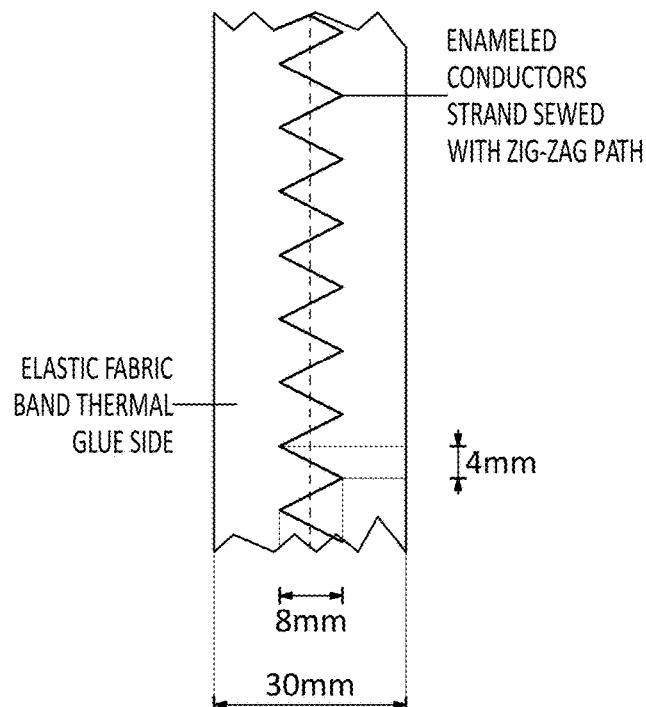
FIG. 3 is a schematic illustration of another example of an elastic electrical connector for use in connecting multiple electrical components to a garment.
Figure 4:
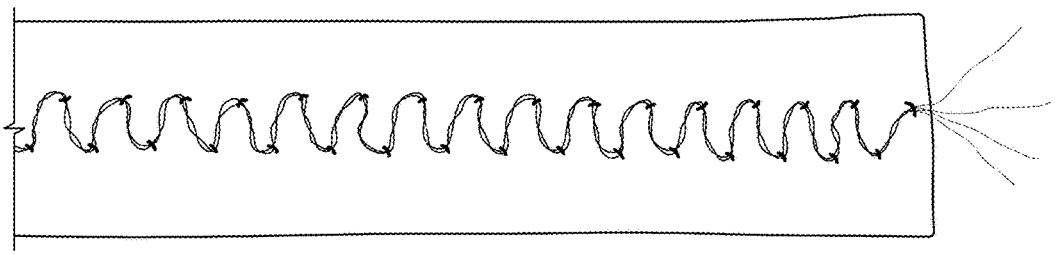
FIG. 4 shows one example of a bundle of insulated (enameled) wires of an elastic electrical connector connected on one side of a fabric material forming an elastic electrical connector.
Figure 5:
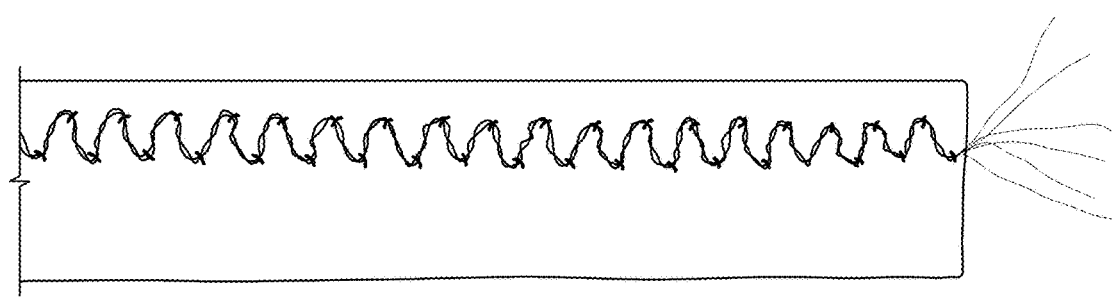
FIG. 5 is another example of a bundle of insulated (enameled) wires of an elastic electrical connector connected on one side of a fabric material forming an elastic electrical connector.
Figure 6:
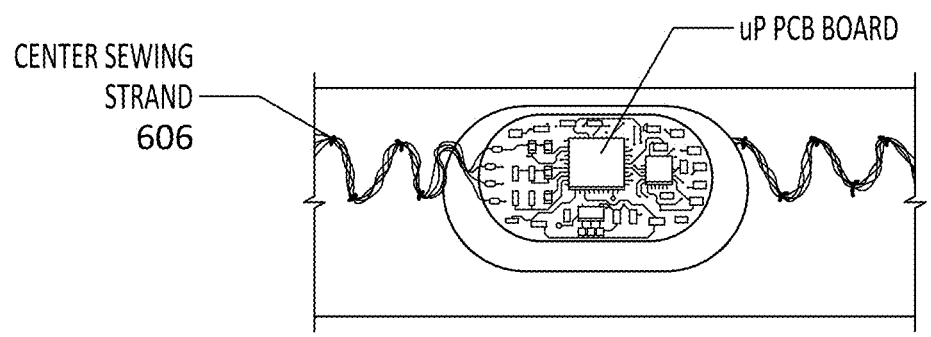
FIG. 6 illustrates the use an elastic electrical connector such as those described herein to electrically connect with an electrical component (e.g., a printed circuit board, or PCB, of a UART BUS).
Figure 7:
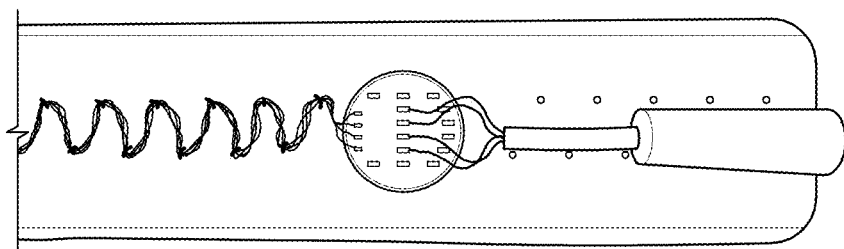
FIG. 7 illustrates the use an elastic electrical connector such as those described herein to electrically connect with another electrical component (e.g., an external connector).

Using a special custom designed sewing machine, the conductors strand is sewn over the glue side of the ribbon (FIG. 3) after the protection film is removed. The sewn ribbon has a standard length from 5 up to 8 meters depending on the size of the spool and the capacity of the sewing machine as well as on the number of wires inside the strand being used. Depending on the application, the strand can be sewn in the center of the ribbon (FIG. 4) or on one side (FIG. 5). The center sewing is normally used for UART BUS distribution where a local uP on board of a PCB (FIG. 6) or an external connection (FIG. 7) are needed. In FIG. 6, a separate thread 606 (shown as "center sewing strand" in FIG. 6) is used to sew the bundle of conductive and insulated wires onto the strip/ribbon of material. This strand is typically a thread of material (e.g., non-conductive, non-wire material) that may be cotton, polymeric (or any blend thereof) and may be stitched over the zig-zag pattern to secure the tip and bottom (the peaks/troughs) of the zig-zag pattern to the strip of substrate material. Stitching with a separate thread of material as shown has been found to allow the bundle of wires to (collectively or individually) slide against the strip of fabric which may avoid puckering or pulling when applied to the stretchable fabric (e.g., compression fabric, etc.), allowing more natural movement of the garment. Thus, the zig-zag pattern shown in FIGS. 6-9 is secured to the substrate material (strip or ribbon of substrate) using a separate thread the forms loops anchored through the substrate fabric strip/ribbon at the peaks and troughs. A continuous thread may be used to stitch the peaks, troughs or peaks and troughs.

Figure 8:
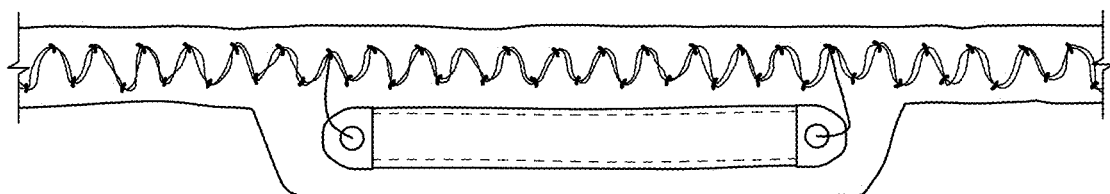
FIG. 8 illustrates the use an elastic electrical connector such as those described herein to electrically connect with an electrical component (e.g., a strain gauge).
Figure 9:
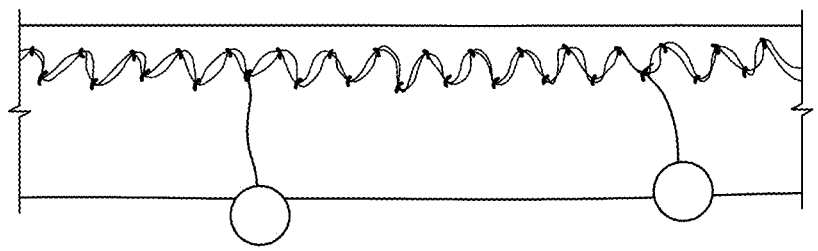
FIG. 9 illustrates the use an elastic electrical connector such as those described herein to electrically connect with an electrical component (e.g., electrodes).

The side sewing may be used for sensors (FIG. 8, showing a strain gauge) and electrodes (FIG. 9) connections in the copper adhesive pads in order to use the free space of the ribbon for cover and seal the contact area.

Figure 10A:
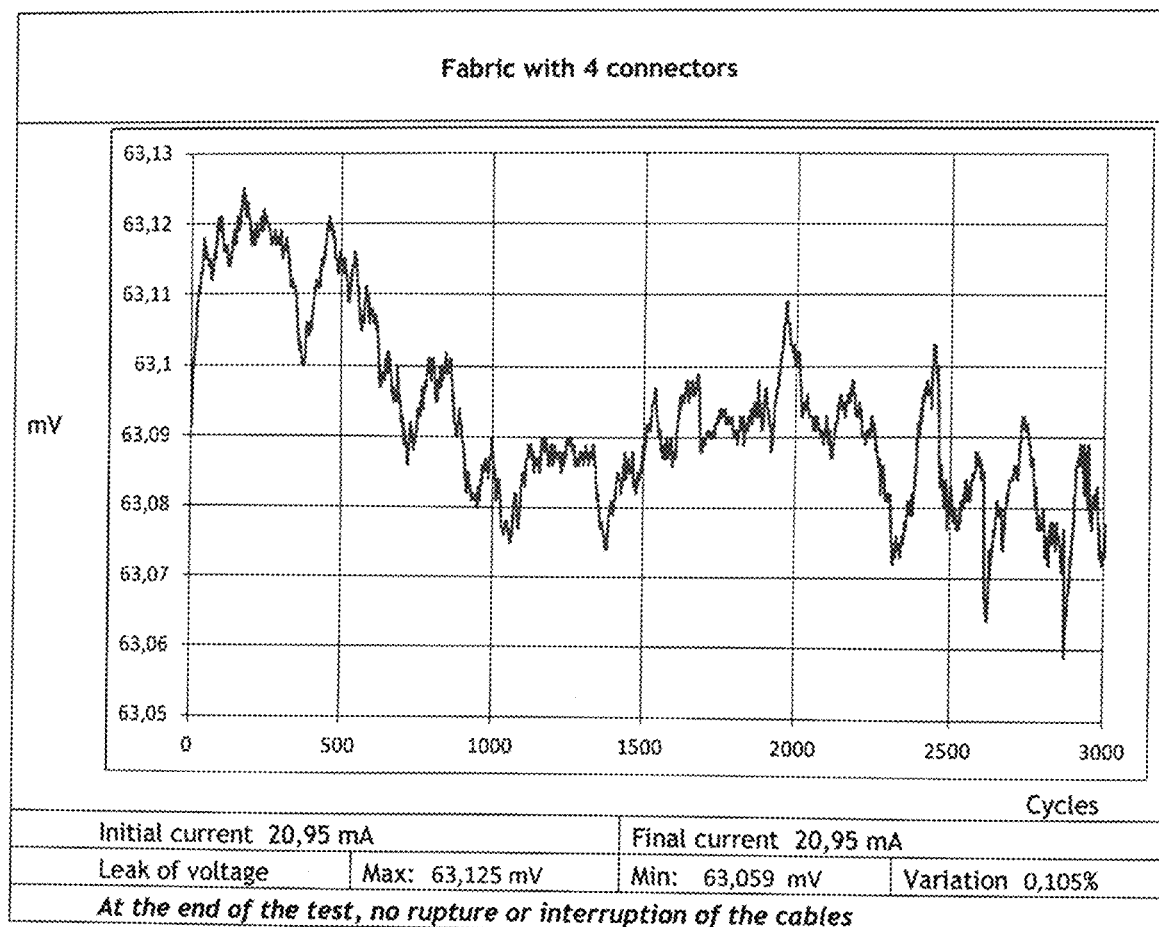
FIGS. 10A-10C illustrate data characterizing the electrical properties and behavior of one example of an elastic electrical connector as described herein.
Figure 10B:
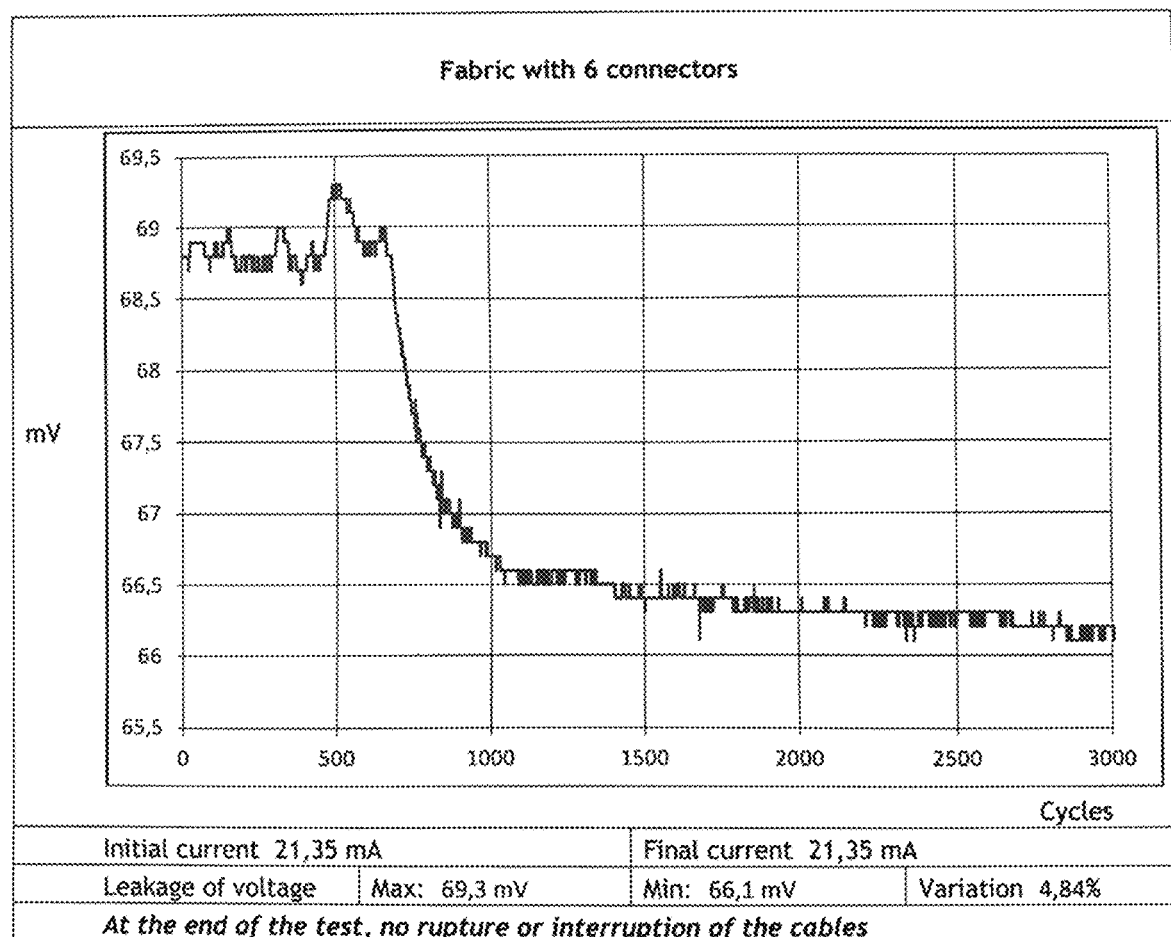
Figure 10C:
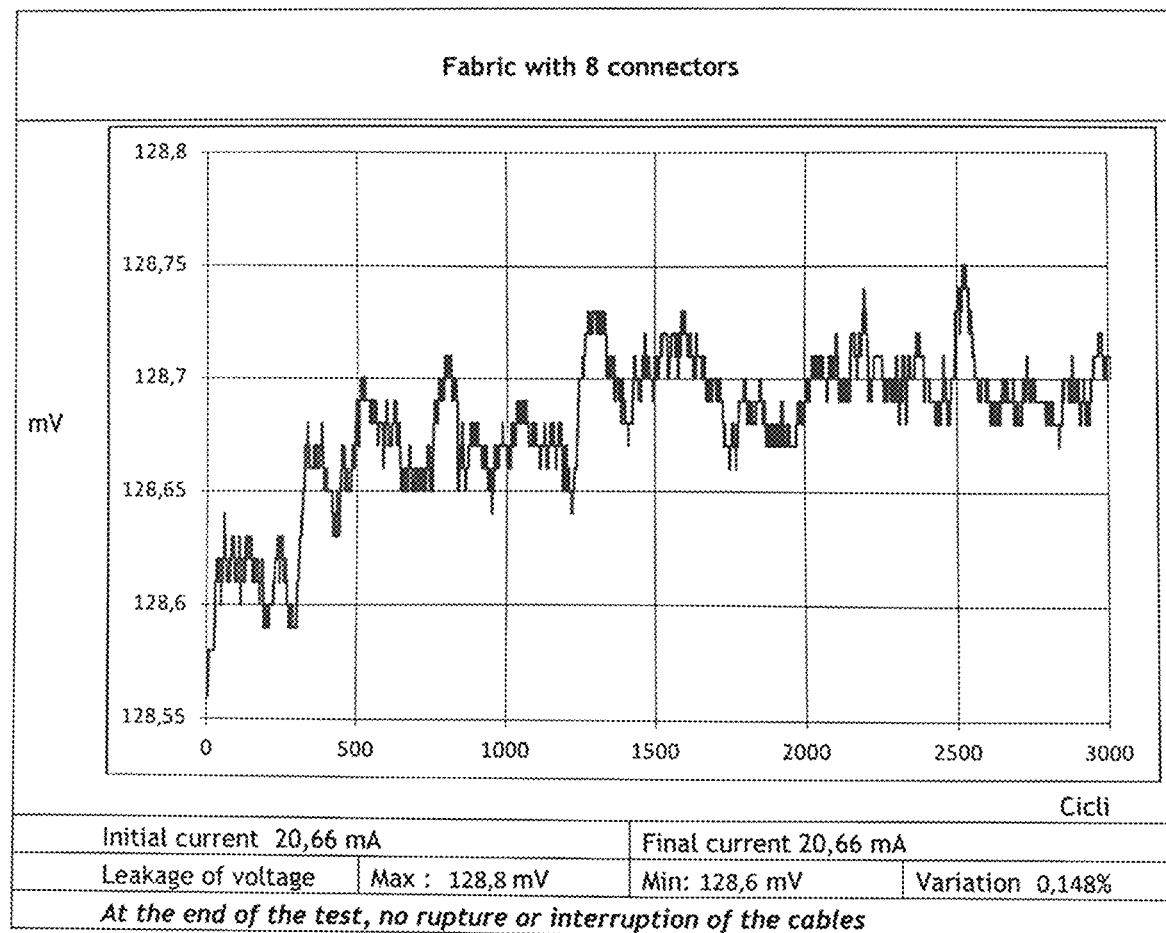

The use of an elastic electrical connector as a garment electrification method has been tested by an external certified laboratory with a cycling test bench machine doing a tensile strength with 20% of elongation to verify the electrical continuity of the conductors. Note that other (e.g., 30%, 40%, 50%, 60%, 70%, 80%, 90%, 100%, etc.) elongations have been successfully tested with similar results as well. FIGS. 10A-10C illustrate these results, which verify that these devices have a surprisingly high reliability and effectiveness.

Each single screen test has been applied by thermal transfer onto a piece of elastic fabric (same fabric material of the ribbon) with dimensions of 45×20 cm. One end of the sample was bound to the frame of the test device, while the other end was fixed to the pneumatic piston. The electric wires of the samples, connected in series each other's, have been connected to the source of direct current power supply through a current-limiting resistor. Potential voltage leak at the ends of the wire was monitored by means of a data logger. The tests have been conducted on three different screen test samples: one with 4 conductors, one with 6 conductors and one with 8 conductors.

TABLE 1

TEST PARAMETERS

| Distance between jaws | 270 mm |
| --- | --- |
| Elongation | 20% |
| Cycle frequency | 1 Hz |
| Number of cycles | 3000* |
| Voltage acquisition frequency | 1 Hz |

*Note:
the number of cycles have been calculated considering one 'dressing' and one 'undressing' per day, for a product life duration exceeding 4 years (as a comparison standard washing cycles are between 40 and 50 times).

Figure 11:
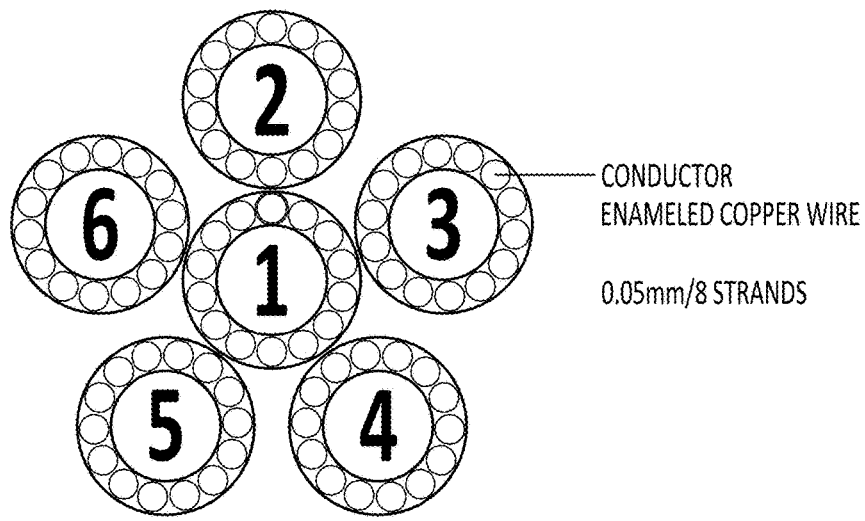
FIG. 11 is a schematic section through a bundle of six insulated (enameled) wires that may be used to form an elastic electrical connector.
Figure 12:
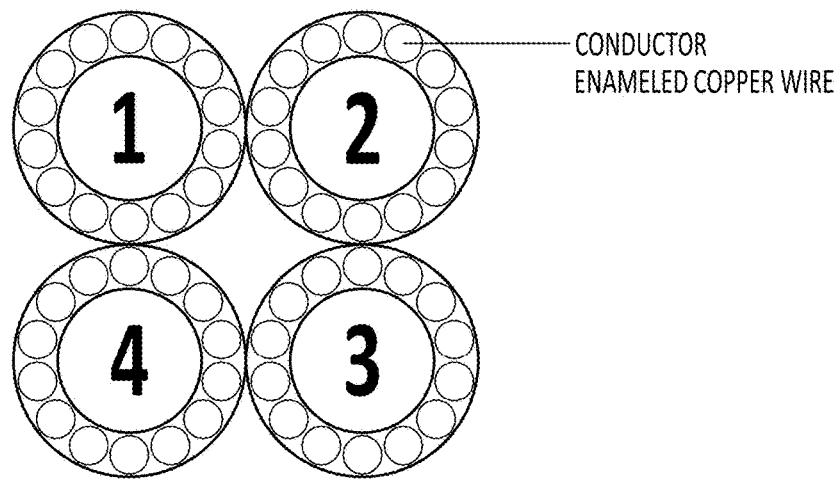
FIG. 12 is a schematic section through a bundle of four insulated (enameled) wires that may be used to form an elastic electrical connector.

FIGS. 11 and 12 schematically illustrate cross-sections through six and four strand wire bundles. The wires in this example are all enameled copper wires that are 0.05 mm/8 strands thickness. These wires may each be individually color and/or patterned coded, as indicated by the numeric keys to the right of each figure.

Figure 15A:
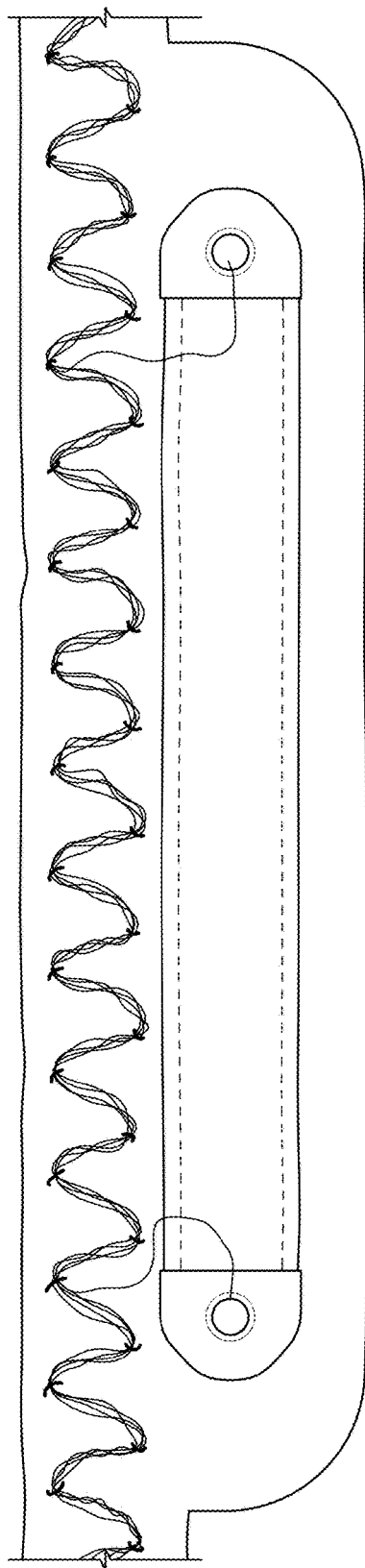
FIG. 15A is an enlarged view of a stretch sensor such as the one shown in FIG. 8, electrically connected to two of the wires of an elastic electrical connector.
Figure 16:
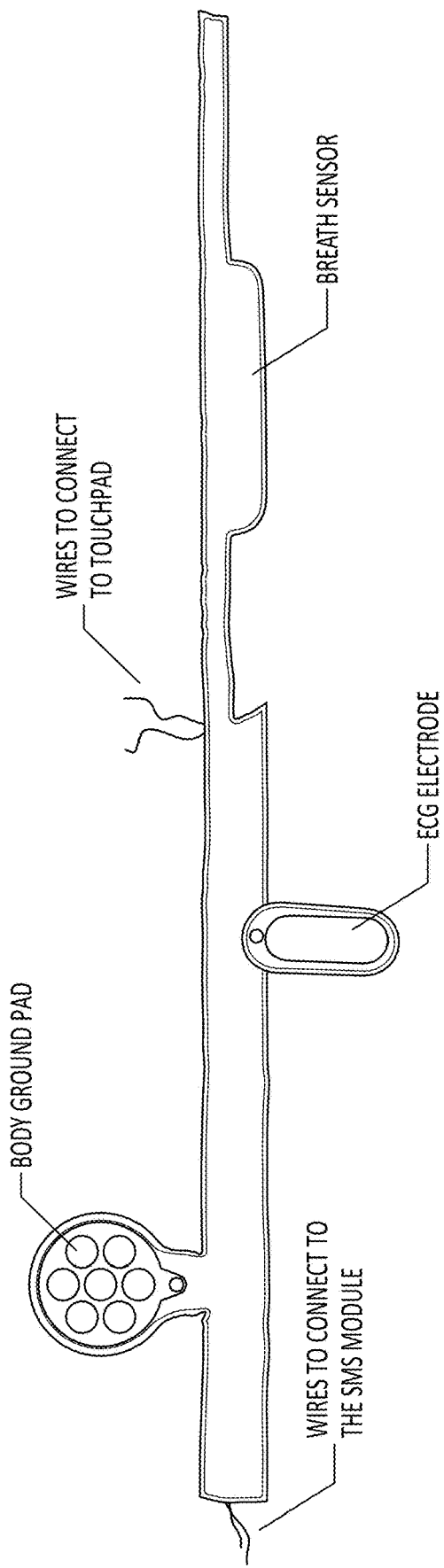
FIG. 16 is an example of an elastic electrical connector shown connected to multiple electrical components, including a body ground pad, ECG electrode, and breath sensor. Additional electrical components may also be added.
Figure 17C:
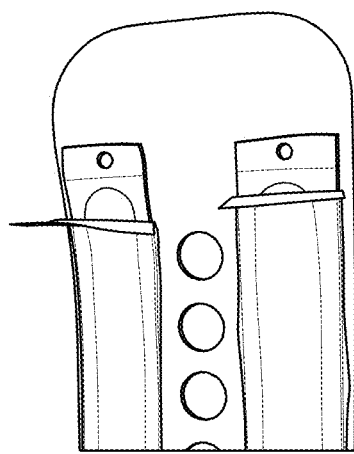
FIGS. 17A-17F illustrate assembly of an electrode sensor. These figures are showing the new electrode assembly (in this case is the EMG electrode). Take note that this new structure is common to all of our electrodes and basically it is made applying, by thermal process, the ink sensor on a fabric base (not elastic) with glue film (the same of the ribbon) on the other side. This "multilayer" gets holed, then the rivet is inserted in the hole.
Figure 17F:
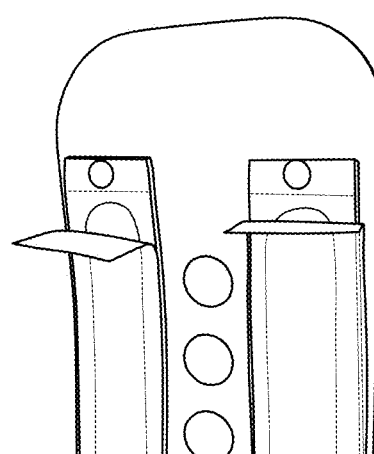
Figure 17B:
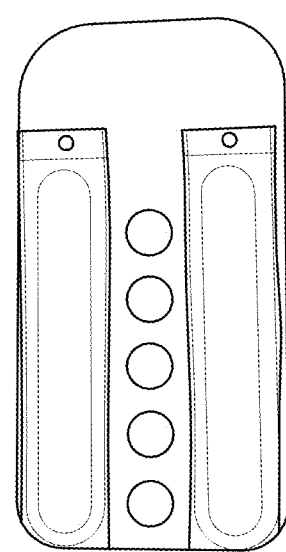
Figure 17E:
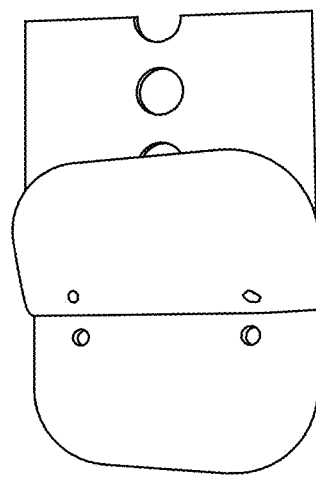
Figure 17A:
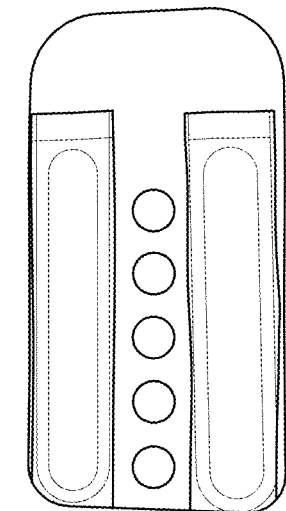
Figure 17D:
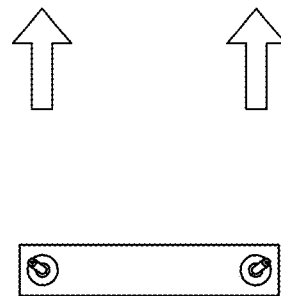
Figure 18:
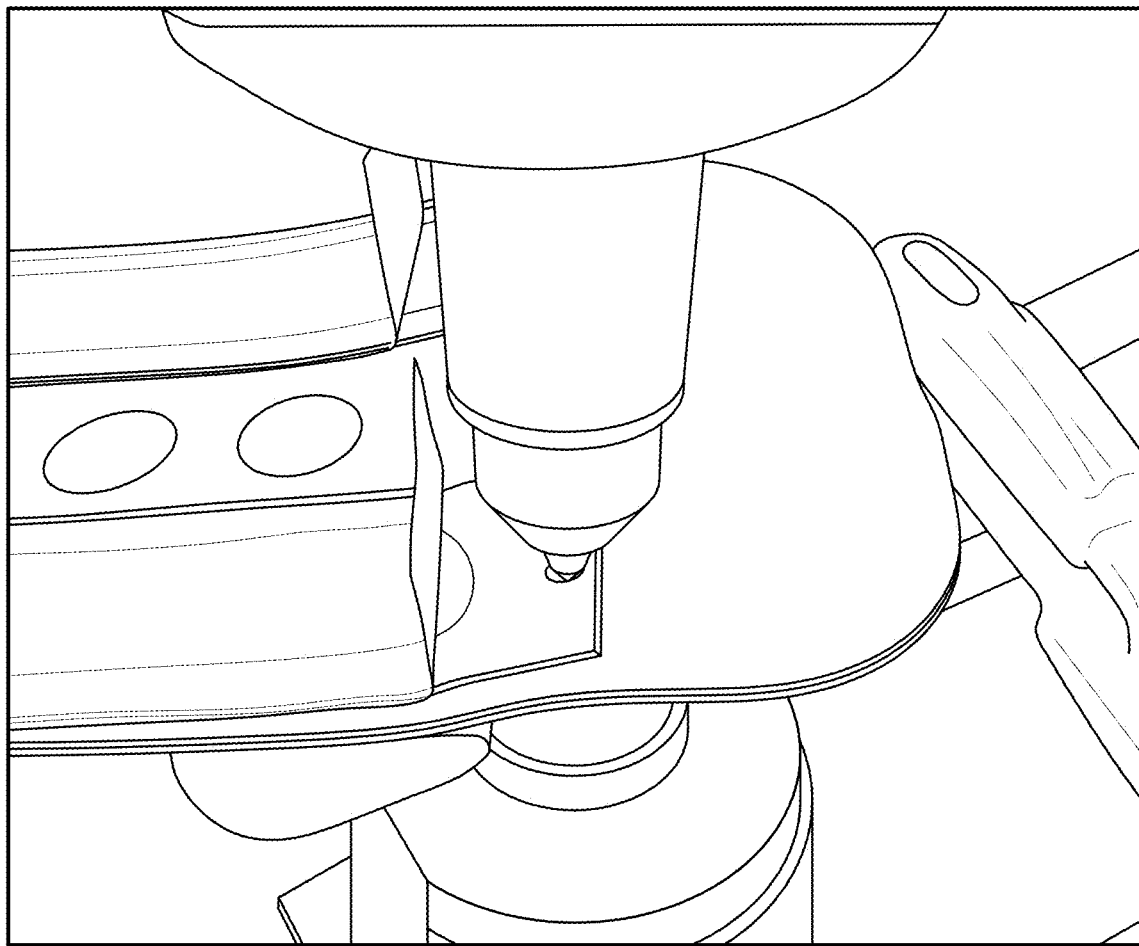
FIG. 18 illustrates machining of an electrode sensor by riveting a connector in contact with a conductive ink forming the sensor.
Figure 19B:
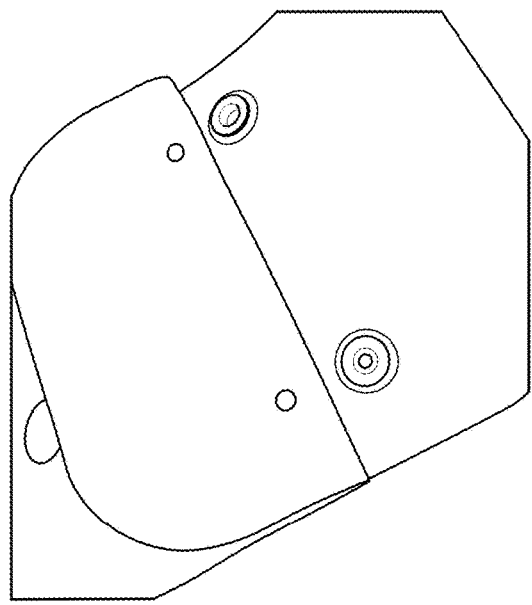
FIGS. 19A and 19B show an EMG electrode.
Figure 20:
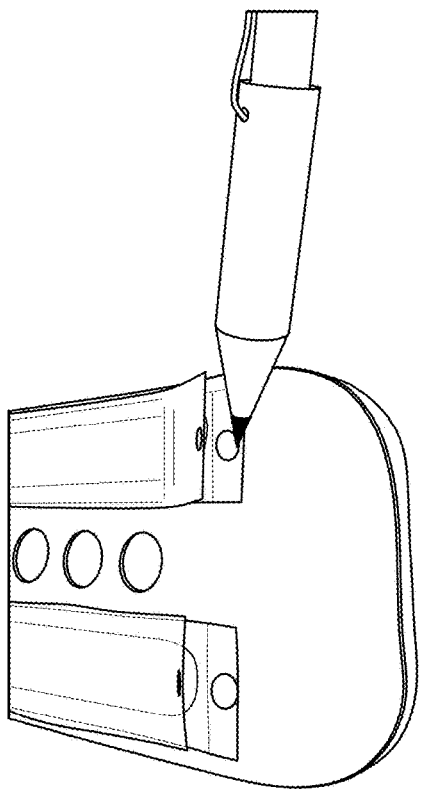
FIG. 20 illustrates soldering of an EMG electrode such as the ones shown in FIGS. 19A and 19B to an electrical connector device by connecting (soldering) at the cap of the attached rivet.
Figure 19A:
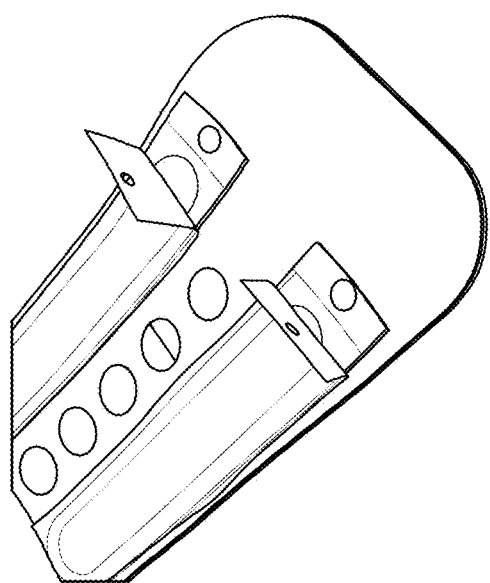

FIG. 13 illustrates an example of a length of elastic electrical connector, shown as long, relatively thin (e.g., between about 2 and 5 cm) and relatively flat (e.g., less than 2 mm). FIG. 14 shows an enlarged view of just the distal end, with the wires (six are shown) exposed. FIG. 15A is an enlarged view of a portion of an elastic electrical connector shown connected to a sensor, specifically a stretch sensor. In practice multiple electrical components (including sensors, PCBs, microphones, electrodes, speakers, etc.) may be connected by the elastic electrical connectors described herein. For example, FIG. 16 illustrates an elastic electrical connector showing multiple electrical components electrically connected to the wires of the elastic electrical connector.

Figure 15B:
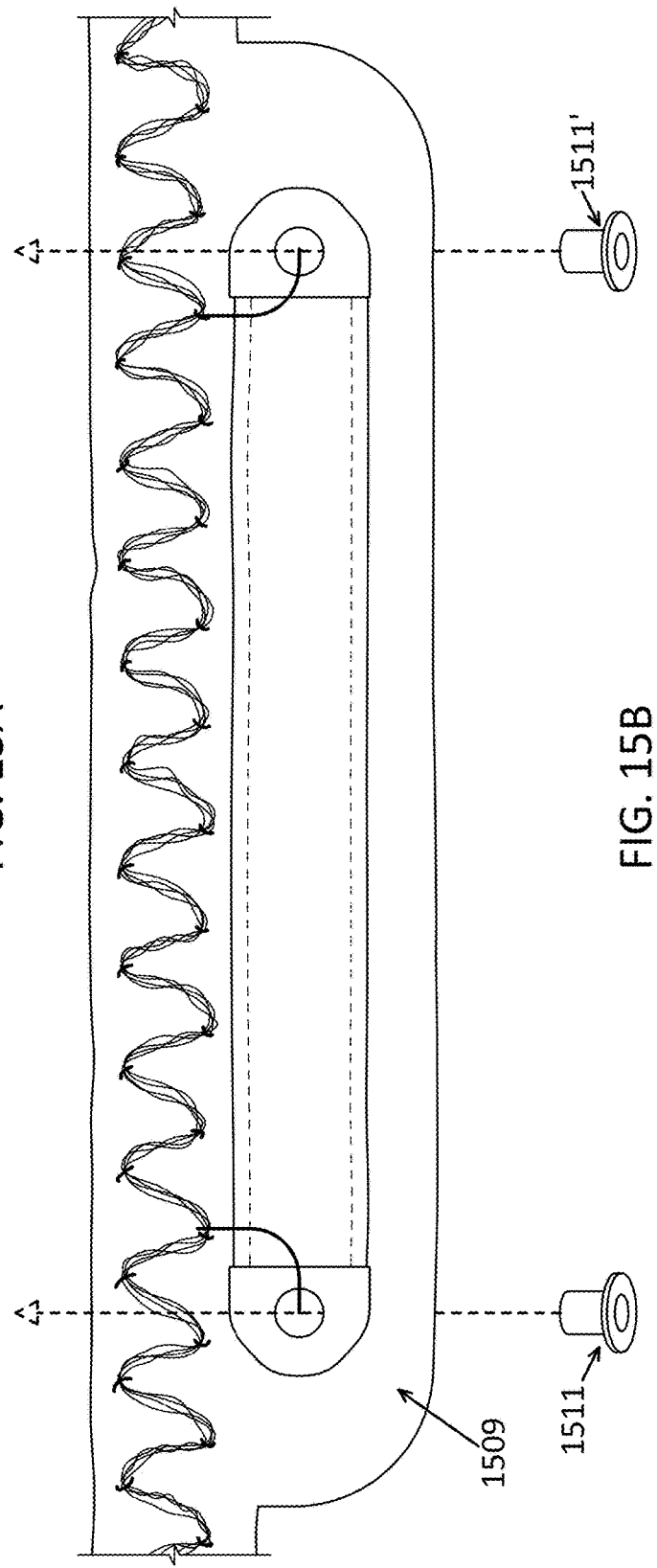
FIG. 15B shows another view (enlarged) of a region of a stretch sensor similar to the one shown in FIG. 15A with the inside exposed.

FIG. 15B illustrates one example of a method of assembling a strain gauge sensor as described herein, that operates based on stretch of an elastic impregnated with conductive particles. In FIG. 15B, the sensor is configured as a breath strain gauge sensor that is fixed directly to the ribbon band 1509 by two rivets 1511, 1511'.

Figure 15C:
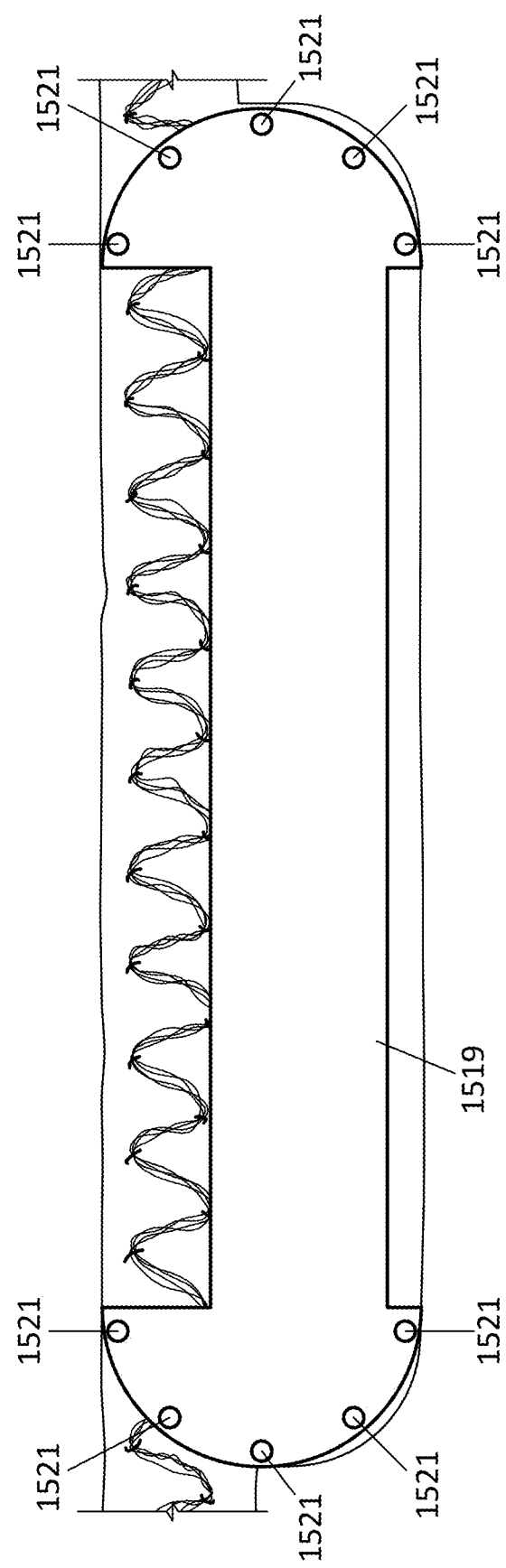
FIG. 15C shows the sensor of FIG. 15B with a cover attached.

In this example, the breath sensor (elastic) is placed, centered and attached to the middle of a fabric strip 1509 as shown. The sensor may be attached by keeping the sensor stable, marking two (or more) holes on the band (e.g., by an awl), punching through the band to form holes of approximately 2 mm diameter and fixing the sensor to the strip with two rivets 1511, 1511'. The rivets may be inserted from the back side of the strip, as shown. Once attached, the sensor may be covered with another layer, as shown in FIG. 15C. In this example, a fabric strip 1519 is attached by applying an adhesive around a perimeter region at one or more locations 1521 (or completely around the edge). This sensor configuration may increase the stability of the sensor, allowing it to work concurrently with the ribbon band forming the sub-assembly (spidon). The lower and upper strips of fabric (e.g., the lower strip forming the ribbon band and the covering strip) may form a pocket in which the elastic sensor may stretch and contract without interference.

FIGS. 17A-17F illustrate one method of making a sensor that may be connected to the elastic electrical connectors described herein.

As mentioned above, the connectors described herein may be part of a system including one or more flexible connectors (which may be referred to as a "spidon"), that may connect multiple electrical components, including connecting such components to a Sensor Management System (SMS), having male and/or female connectors with their components. The spidon may be configured as a harness with multiple intelligent strands (e.g., made of twisted enameled multi (2 to 20, 2 to 18, 2 to 16, 2 to 14, 2 to12, etc.) wires sewed against one side of a fabric strip in a sinusoidal (e.g., zig-zag) pattern, and may include isolating glue. The spidon may connect and therefore include electrodes, sensors, haptic actuators, touch-points and ICs such as microcontrollers and IMUs. A spidon may be designed for garment application where signals coming from multiple sensors, electrodes, touch points and haptic actuators placed in different parts of the garment/body have to be connected to microprocessors placed in different parts of the garment/body and to (an) external devices such as a Multi Media Module device (MMM). The SMS connector is part of the Spidon and may be positioned in the upper center of each shirt, which corresponds to the center between the wearer's shoulder blades, the place in the human body less sensitive to weight and to touch.

The SMS may be placed in each shirt rather than in the MMM. This solution increases the cost of the system: rather than buying an MMM with a SMS and use it with many shirts with no SMS, the user now has to buy a MMM without an SMS and use it with many shirts each one having an SMS. However this solution allows to increase the number of sensors, electrodes, touch points and haptic actuators in the garment without having to increase the size of the male and female connectors on the MMM. Potential users may not wear an SMS with more than 36 pins because its size would become too intrusive and uncomfortable.

By placing the SMS in the connector glued to the shirt, each sensor, electrode, touch point or haptic actuator may be directly connected to the SMS microprocessor through the already mentioned strands. The SMS microprocessor is then responsible for acquiring and processing each sensor, electrode, touch point or haptic actuator data and signals, and for sending those calculations to the MMM through a digital serial port that requires just two pins on the SMS connector.

It should be noted that in case the SMS would have been placed in the MMM rather than in shirt connector, all the sensors, electrodes, touch points or haptic actuators would have been connected to the MMM, thus dramatically increasing the number of pins on the connector and, as a result, increasing its overall size. In this case, a high number of sensors, electrodes, touch points or haptic actuators could be achieved only at the cost of a bigger connector size. On the contrary, the chosen solution ensures small connector dimensions and a high number of sensors, electrodes, touch points or haptic actuators (up to forty-four connections or more) at the same time.

In addition to the already described architecture, additional technology allows the system to increase the number of sensors, electrodes, touch points or haptic actuators without increasing the number of strands that need to be embedded into the garment and connected to the SMS connector. This may be achieved by using the intelligent dedicated strands that were already mentioned above. These intelligent strands which connect embed sensors, electrodes, touch points, haptic actuators and microprocessors that communicate with the SMS microprocessor in a similar way as the MMM and SMS are. Each bundle may include multiple strands or wires. For example, four twisted enameled wires may be used: two wires to carry signal (e.g., acting as a digital serial communication bus), and two for the power supply and ground.

Following a similar principle as the one described for the SMS, it is possible to consider additional 'modules', each containing one or more, each additional microcontroller, embedded into intelligent strands can be then connected to a high number of different sensors, electrodes, touch points and haptic actuators placed on the garment. These modules are connected to the SMS by the strands. The microcontroller, in fact, manages not only sensor conditioning, but also digital communication.

In addition to this first advantage, there are two other important features that should be noted. First, by using this overall system architecture, the number of wires that go around the garment is considerably reduced, because the sensors, electrodes, touch points or haptic actuators are not connected to the SMS but to the microcontrollers, and also because all the microcontrollers can share the same digital serial bus for communicating with the SMS microcontroller. This is possible because each microprocessor is identified by an address, thus it can be uniquely identified while communicating with the SMS. The fact that the number of wires is reduced by this solution, surely improves garment wearability and comfort for the final users. Wearability and comfort is important for wearable computers like ours that operate when in direct contact with a large portion of our skin (entire upper body/shirts, entire lower body/tights, hands/gloves, feet/socks, head/balaclava and more) contrary to computers, smart phones that are used while on desks, in hands or in pockets or intelligent watches or wrist bands that are worn on our wrists.

It should be also noted that the number of different microprocessors that can share the same digital serial bus is theoretically infinite or very high and limited primarily by the space on the garment and by the computational power of the SMS microcontroller that needs to manage all the microcontrollers placed around the garment (including the interrogation frequency, bandwidth, etc.).

Lastly, the combination of microcontrollers, sensors, electrodes, touch points or haptic actuators connected to it, allows to create a sort of "smart sensorized node" that can be managed independently from the SMS and can help to distribute the data processing and to relieve the SMS microcontroller processing load.

Figure 21:
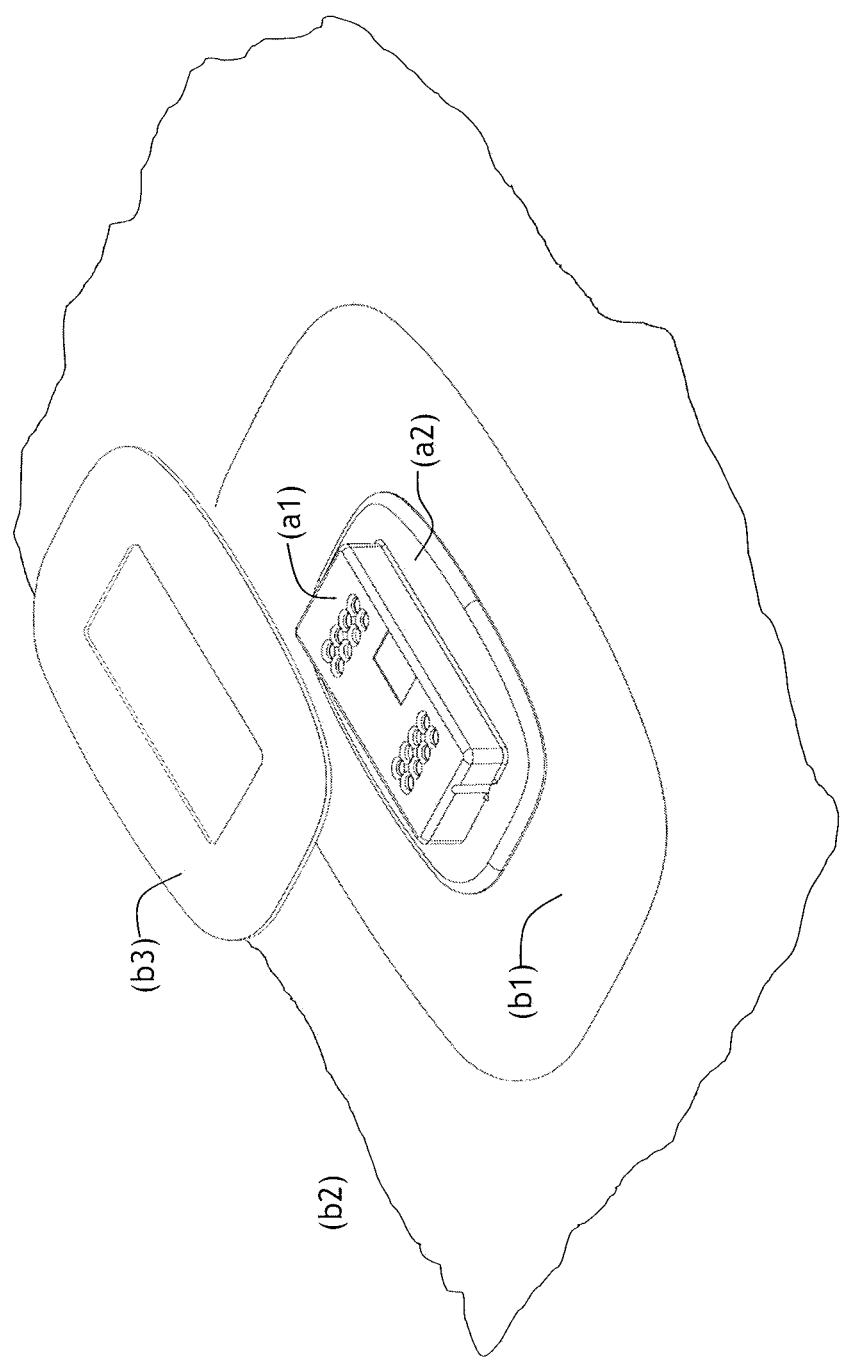
FIG. 21 shows one example of a sensor management system (SMS), including a housing, connected to a fabric (e.g., garment), to which an elastic electrical connector may also be connected.

Referring to FIG. 21, the connector body (a1) is made off polycarbonate plastic material with an overall thickness of 2 mm in order to guarantee shock protection. At the base there is a flat flange (a2) which allows a good stability on the soft plastic layer support (b1) which is hot-melted to the garment fabric (b2). One additional purpose of this flange is to fix the connector to the first plastic layer through an additional layer (b3) which is hot-melted to the flange in order to 'sandwich' the connector to further stabilize it. The final assembling is shown in FIG. 22.

In FIG. 23, the SMS connector has four magnets (a3) placed at the four corners cylindrical seat (a4) that allows to lock easily and to stabilize the external device to be connected. This connector has a 68 IP grade to be completely waterproof to endure regular washing (it is an 'intelligent' garment thus needs to be regularly cleaned after use), thus the magnets are positioned at the back side of the surface in order to avoid possible oxidation and rust deposit.

In FIG. 24, despite the matching position between the external device and the SMS connector is constrained, on both sides right and left, is present a semi-cylindrical slot (a5), designed to avoid unwanted reversed connections.

The connector may also be made waterproof, e.g., or at least water/moisture resistant, as shown in FIG. 25. The female contacts receptacle has been designed to avoid any water access to the inner parts. After the female contacts (a6) insertion in the corresponding pinhole, the back side of the connector is filled with epoxy resin (b4) in order to seal completely any interstice.

Figure 26:
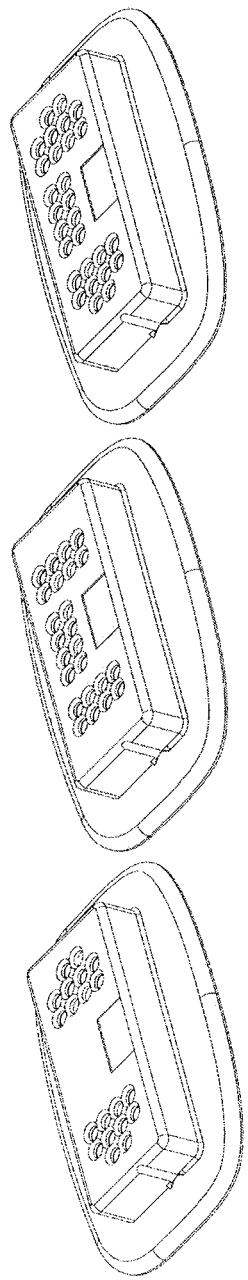
FIG. 26 illustrates different housing configurations (e.g., left 20 poles, middle 24 poles, and right 28 poles) for an SMS housing.

One basic pins configuration is shown in FIG. 24 with 12 poles, but it could also be configured with 16, 20, 24 and 28 poles as shown in the variations of FIG. 26 (showing, 20, 24 and 28, respectively).

Figures 27A, 27B:
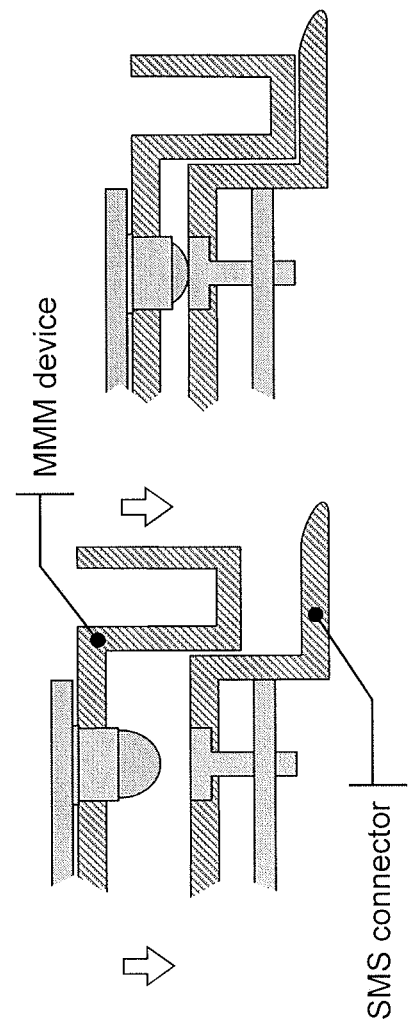
FIG. 27A illustrates a multimedia module device (MMM device) mating with an SMS connector, show in partial cross-section.
FIG. 27B shows the MMM device and SMS connector fully mated.

FIG. 27 illustrates the electrical connections between the SMS (Sensor Manager System) connector and the external Multimedia Module device (MMM) are through female contacts (a6) and pogo pins (b5) that thanks to the internal spring ensure stable and reliable electrical contacts even under extreme shocks and vibrations.

FIGS. 28-31 illustrate an SMS. The SMS shell shown contains a printed circuit board assembly (PCBA) (FIG. 28), directly soldered to the female contacts and acting as a central unit able to acquire and process data and signals from sensors, electrodes, touch points or haptic actuators embedded into the garment and transmit them to the MMM.

The SMS main component is a microcontroller. As already mentioned, the main purpose of this microcontroller is to manage the acquisition of data and signals coming from sensors (e.g. ECG electrodes, EMGs, string gauges, skin conductance, IMUs, etc.), electrodes, touch points or haptic actuators. The same component is also involved into a first phase of data processing (e.g. digital filters) and into the communication of these calculations to the Multimedia Module through a serial digital line.

Figure 29:
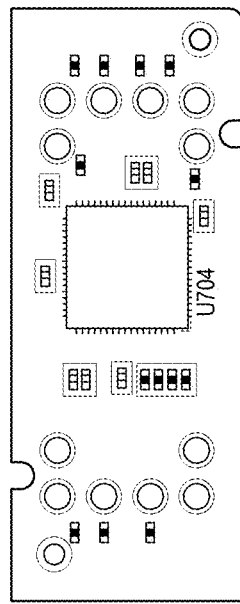
FIG. 29 shows a component layer of an SMS microcontroller.
Figure 31:
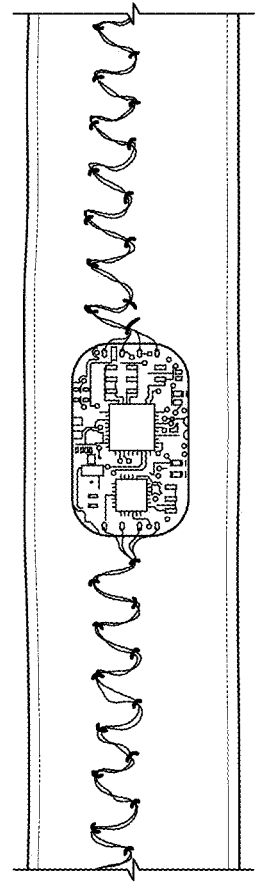
FIG. 31 is another illustration, similar to that shown in FIG. 6, of an SMS connected to an elastic electrical connector as described herein.
Figure 28:
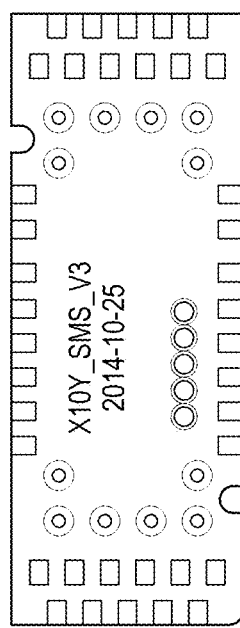
FIG. 28 shows a solder layer of an SMS microcontroller.
Figure 30A:
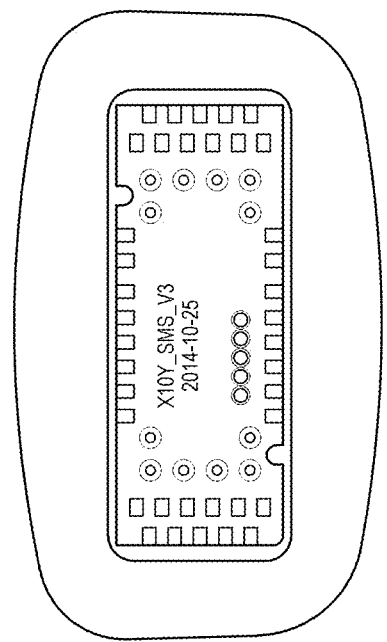
FIG. 30A shows the SMS microcontroller of FIGS. 28 and 29 housed within an SMS housing.

In one example, shown in FIG. 29, twelve pins (female contacts) ensure the electrical connection. These pins are used for having the digital communication, the power supply coming from the Multimedia Module battery (regulated +3.3V and protected VBAT) and other hardware features (e.g. sensing of the connection between Multimedia Module and SMS). In FIG. 30A, the SMS PCBA solder layer has been designed to allow several connections to various types of sensors, electrodes, touch points or haptic actuators distributed throughout the garments to cover the body specific parts (arms, hands, legs, feet, shoulders, head, thorax, back, abdomen, etc.) through a special harness made with elastic ribbon to which is sewed a strand of 2 to 12 (or more) enameled conductors/wires. The strand (bundle of wires) is sewn at the peak and trough of the zig-zag pattern, with each side in this example measuring from a minimum of 2 mm to a maximum of 4 cm and with angles between 1° and 179° in order to allow the ribbon to stretch from 10% to 500% of its length. The ribbon band is made with the same fabric utilized to make the part of the garment (sleeve, shoulder, etc.) where it is applied. Since stretchable fabrics stretch in various directions (from 1 to 6 or more) the ribbon is applied following the exact stretching direction of the part where it is applied. This process ensures that the ribbon has the same elongation and the same return as the fabric where it is applied to improve functionality (conductivity and data collection) and comfort in wearing the garment. It also improves the looks of the garment (seamless stretching and return of the garment when body is in motion). The elastic ribbon is glued to the stretchable fabric through an adhesive film especially formulated for fabric applications, this adhesive is on the same wiring layer and it is used for hot fixing to the garment's elastic tissue in order to block and keep the zig-zag strand shape after hot application. The zig-zag shape has been optimized to assure the wires elongation during donning and usage avoiding the mechanical stress of the copper conductive material.

Figure 30B:
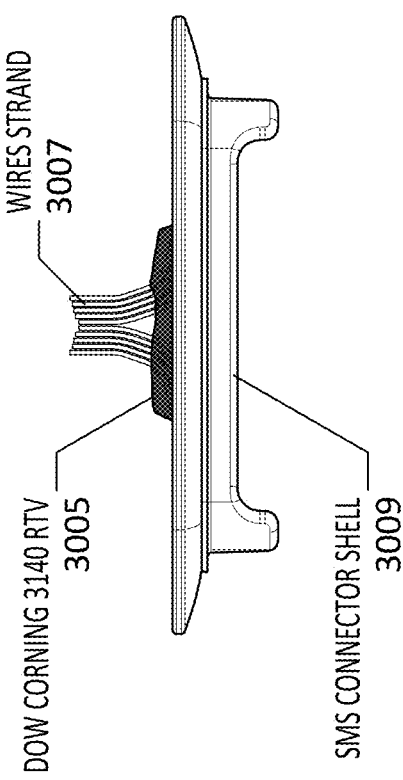
FIG. 30B shows another example of a housing for an SMS microcontroller.

FIG. 30B is another example of an SMS housing that may be used to secure a controller (SMS controller) that is configured to allow it to securely housing the controller and allow it to interface with a plurality of inputs, e.g., from flexible ribbon connectors, without pulling the wires out of the controller. In FIG. 30B, the SMS connector housing (shell 3009) allows the SMS circuitry (controller, not visible in FIG. 30B) to rest snugly within the housing so that a seal may be provided over the connectors between the wires 3907 and the circuitry. In FIG. 30B, the cover is not shown over the SMS housing; before the back cover is attached, the SMS may be coated with a region of epoxy resin. A sealant 3005 such as a ring of Down Corning silicone may be placed all around the wires strands collected in the center of the PCB. This silicone 3005 crown may allow the wires exit gently from the SMS connector shell, retained in position, and may also provide some degree of water resistance to the connections.

In any of the connectors described herein in which the insulated wires are sewn onto the substrate, a separate thread material (e.g., cotton, polyester, blend, etc.) may be used to sew the bundle of wires against the substrate (fabric) at the appropriate regions. A single loop of thread, or multiple loops of thread may be used to hold the wires in place. The thread may pass around the bundle of wires one or more times, and through the substrate one or more times. The stitches securing the wires to the substrate may be separated by a spacing distance (e.g., see FIG. 1, element 103).

The wired elastic ribbons connect different sensors types as: IMUs, EMGs, electrodes, touch points, ink sensors by conductive washers connections (e.g., FIG. 31), haptic actuators, PCBA (FIG. 10) and any kind of electrical connections.

In case of PCBA incorporation, this must be previously covered by epoxy resin to prevent any water, sweat or any kind of liquid penetration inside the electronic circuit. The coverage has a smooth and rounded shape in order to have a good touch feeling and an attractive appearance from the external side of the garment.

The conductive washers may be used for connect the copper wire, soldered on it, to the ink sensors and are made by silver-chloride thin steel film in order to have a strong bending resistance and good protection against rust and oxidation, maintaining optimal conductivity values. The coupling between the washer and the ink surface is made thanks a special conductive adhesive named z-axis (manufactured by 3M) that allows transmission of electrical signals between the two different material surfaces.

Figure 32:
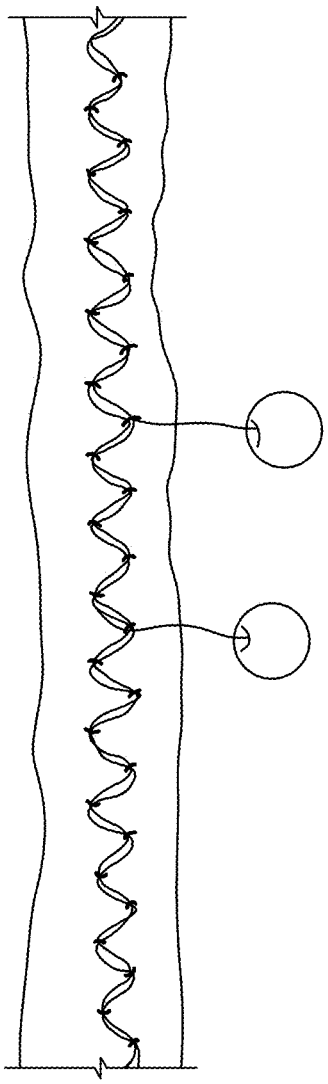
FIG. 32 illustrates another example of electrodes connected to an elastic electrical connector, similar to that shown in FIG. 9.

With this system, it is possible have also input/output electrical connections, like connectors or external modules in every parts of the garments thanks to the "splitter PCB" (SPP) that allows the connection of the thin enameled conductor to standard harnesses. As per the PCBA, the SPP must be protected by epoxy resin coverage after cabling. FIG. 32 illustrates a connector electrically connected to a pair of electrodes.

Figure 33:
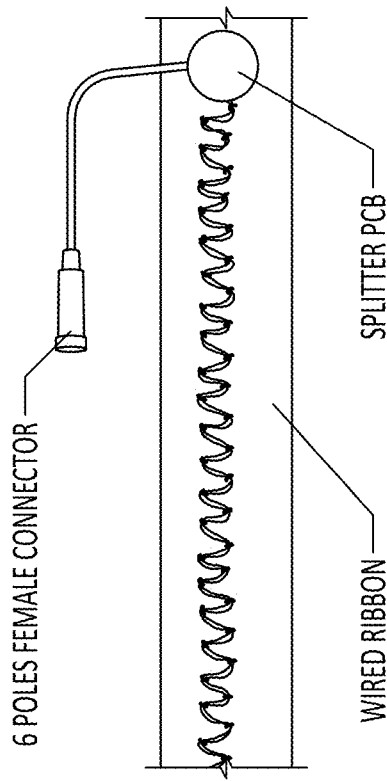
FIG. 33 illustrates an elastic electrical connector connected to a six-pole female connector and a splitter PCB.
Figure 34:
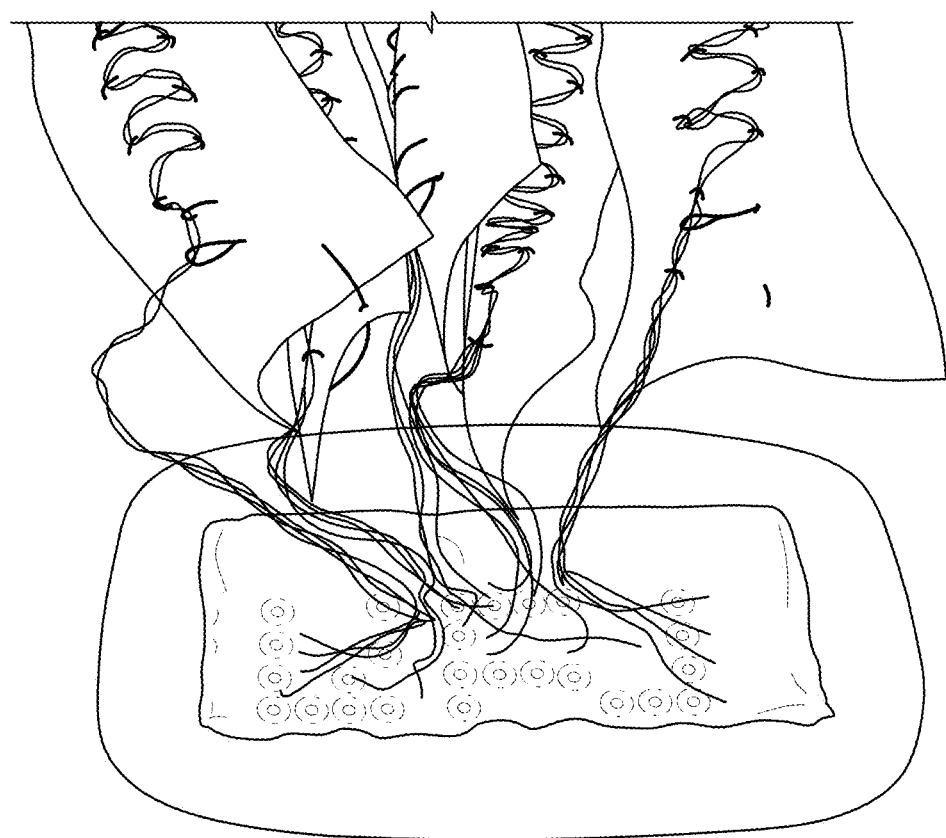
FIG. 34 shows four elastic electrical connectors, each electrically connected to the SMS connector.

All the wired ribbons terminations are soldered to the SMS PCBA pads on the Solder layer and, after test, are incorporated by epoxy resin inside the SMS connector shell (FIG. 33) in order to completely prevent water penetration. A Spidon subsystem (e.g., FIG. 34, FIG. 35) may then be ready to be coupled with the garment. First of all the SMS connector may be inserted through a slot present on the high back side of the shirt and mechanical fixed to the garment as described above (e.g., FIG. 21), then following the draw projected by a laser projector, the various wired strips may be positioned to the right place of the internal garment surface and using a hydraulic press for thermo printing, fixed to the tissue.

Figure 35A:
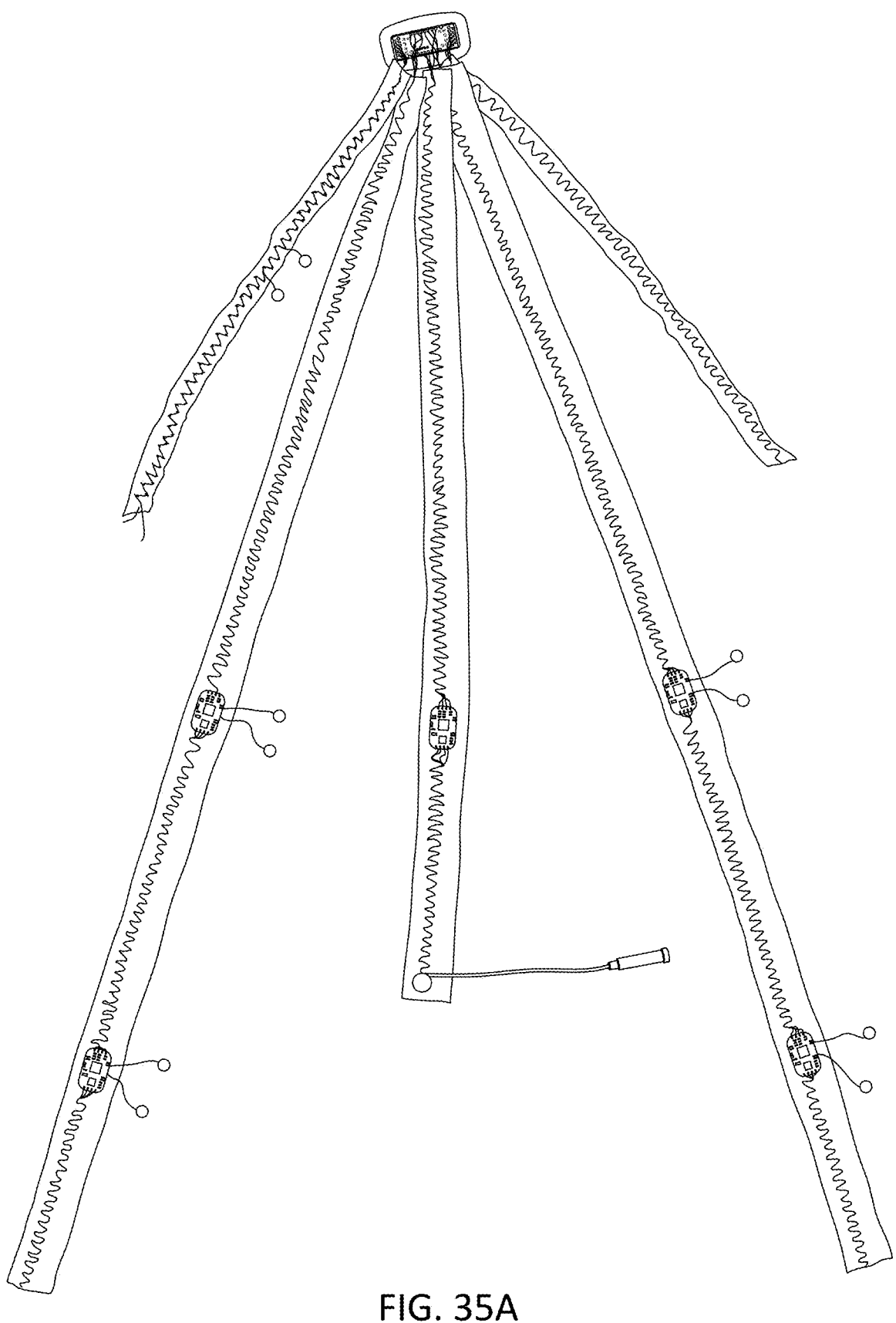
FIG. 35A illustrates a system or subsystem (referred to herein as a 'spydon system' or spydon subsystem) including multiple (e.g., 5) elastic electrical connectors that each contain a plurality of conductive wires connected or connectable distally to multiple different electrical components (e.g., sensors) and connected at a proximal end to an SMS connector; this entire network may be adhesively and/or otherwise transferred and connected to a fabric to form a wearable garment.
Figure 35B:
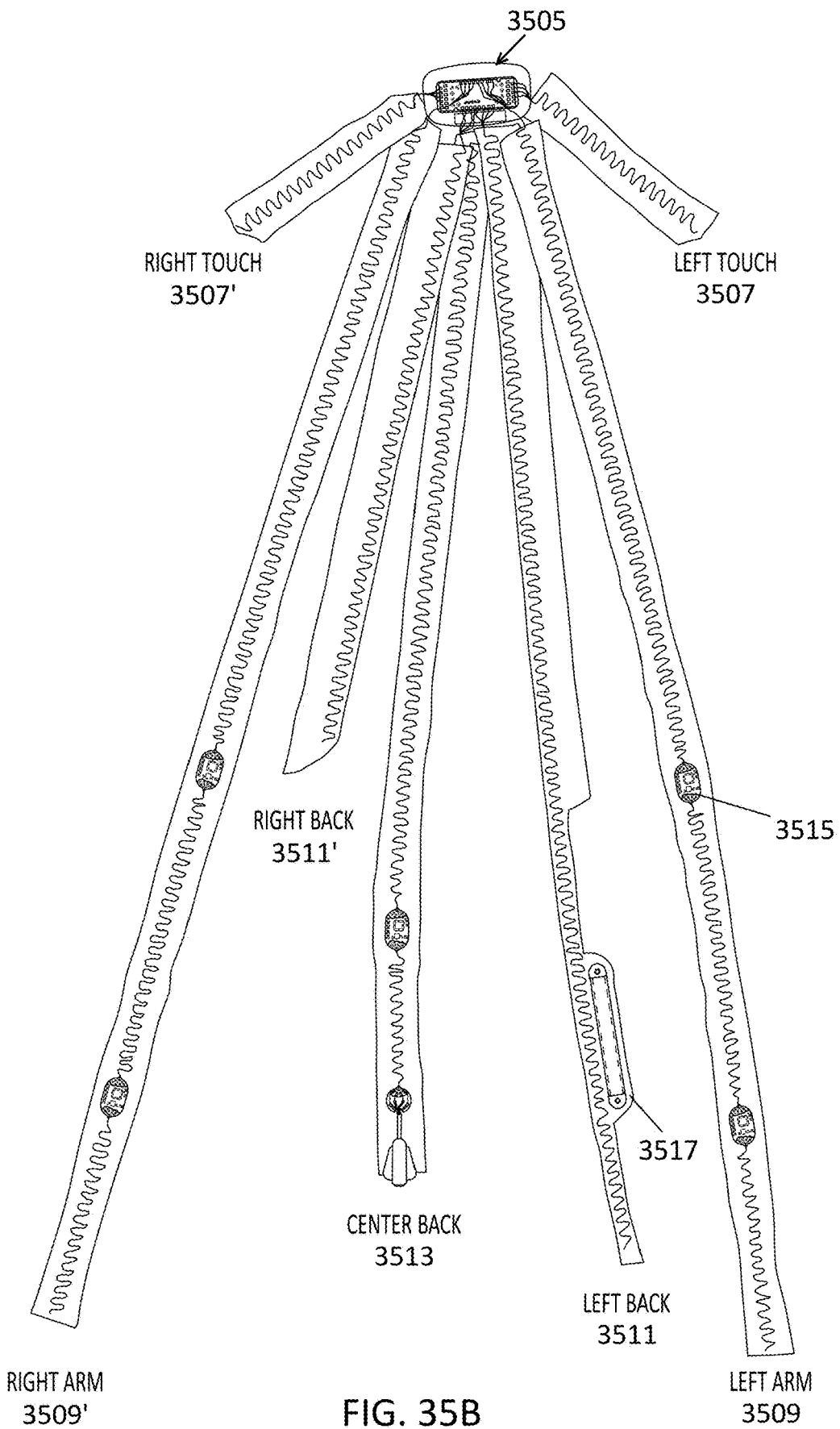
FIG. 35B is another example of a system (or subsystem) having multiple elastic electrical connectors each containing a plurality of conductive wires connected or connectable to multiple different electrical components (e.g., sensors) and connected at a proximal end to an SMS connector, similar to that shown in FIG. 35A.
Figure 37:
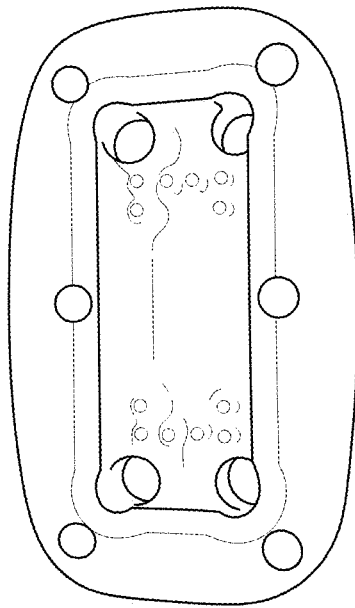
FIGS. 36-39 illustrate an alternative variation of an SMS (FIG. 38) and housing (FIGS. 36, 37 and 39) for the SMS circuitry.
Figure 39:
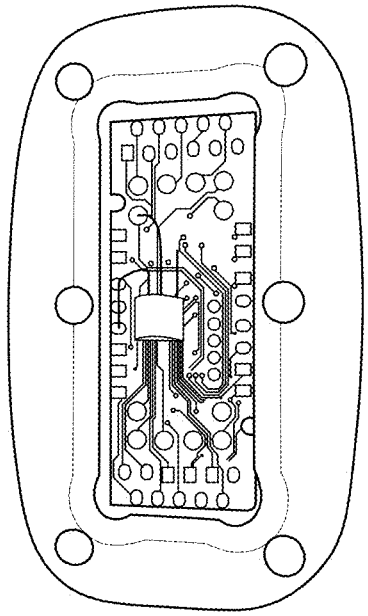
Figure 36:
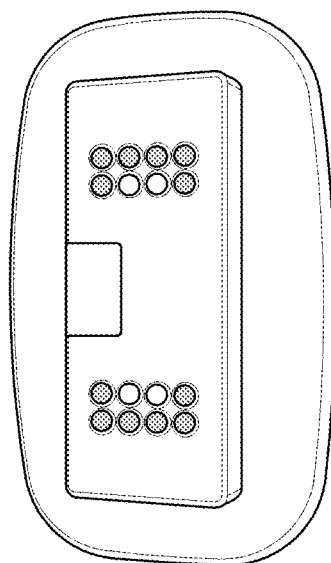
Figure 38:
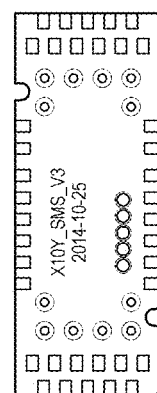

FIG. 35B illustrates another example of a subsystem including a plurality of elastic electrical connectors that each include a plurality of wires arranged and attached as described herein (e.g., including a plurality of wires extending along a length of a first side of an elongate strip of fabric substrate in a sinusoidal or zig-zag pattern, wherein each of the wires is electrically insulated, and wherein the plurality of wires are attached to the first surface by a stitch at a peak and a trough of the sinusoidal or zig-zag pattern). In this example the subsystem includes seven branches (strips) that all connect at one end (a proximal end) to an SMS controller 3505 (held in an SMS housing). Each branch may include one or more sensors 3517 and/or IMUs 3515 (which may, e.g., process data from the one or more sensors and prepare it for transmission to and by the SMU 3505). The strips forming the subsystem may then be attached or otherwise integrated into a garment (sewn, glued, embedded, layered, attached, etc.), such as a shirt, e.g., a t-shirt having long or short sleeves, including but not limited to compression garments. In FIG. 35B, the subsystem includes connectors for a left 3507 touch sensor, a right touch sensor 3507', a left arm 3509, a right arm 3509', a left back 3511, a right back 3511' and a center back region 3513. The different connectors may have different lengths and may connect to different components, as illustrated.

Other examples of SMS and SMS connectors are shown in FIGS. 36-39.

Figure 40A:
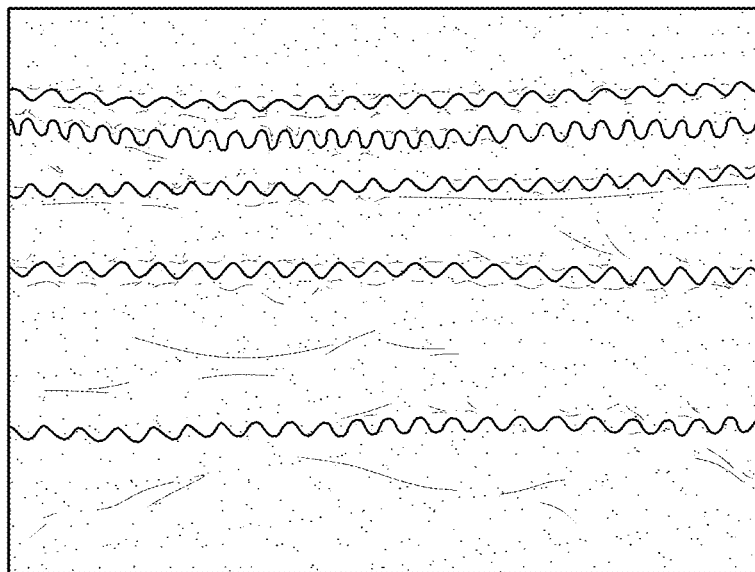
FIGS. 40A-40C illustrate examples of conductive thread sewn into a substrate (e.g., fabric)
Figure 40B:
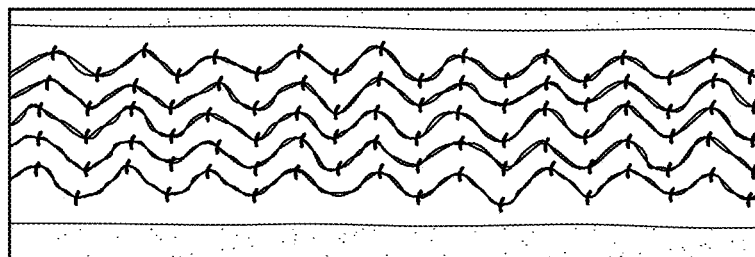
Figure 40C:
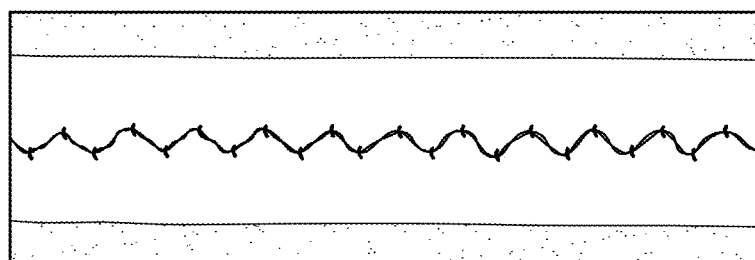

FIGS. 40A-40C illustrate other examples of flexible connectors having a wires attached in a sinusoidal or zig-zag pattern. In these example, one or a bundle of fibers is attached (including sewn into the fabric, rather than using an additional thread to sew the wires onto the substrate as described above in FIGS. 1-39). Thus, these embodiments may not have all of the advantages, including ease of removing and connecting a wire, as described above.

In some variations it may be useful to use conductive threads or other high-conductivity connectors, such as those shown in FIG. 40A-40C. In this example, the conductive thread is stitched onto the garment in a wavy (e.g., zig-zag, sigmoidal, etc.) pattern that allows some stretching in the net direction of the stitching. As described above, respiration (sensors) traces may be formed of stretchable conductive ink patterns to take advantage of the change in conductivity with the change in resistivity with stretching of the conductive ink pattern. In this example, the sewn pattern of threads includes an approximately 35-40 degree zig-zag pattern allowed the stitch to elongate slightly with the fabric. In some example, the conductive thread is a metallic conductive thread. The angle formed at each turning point (in the wavy pattern) and the width of the pattern may depend upon the textile used. In general, the higher the stretchability of the textile, the smaller the angle. The number of threads may vary; in general, any number of threads may be used depending, for example, on the number of sensors and their pins that need to be connected. The threads are typically sewn directly on the garment. The electrical insulation of the thread may be obtained by an external coating on the thread (e.g. silicone, polyester, cotton, etc.) and/or by a layer of insulating adhesive, as described above. The thread connectors may also be used as part of a transfer as described above. For example, a conductive thread may be sewn on a band made on the same fabric of the garment and then transferred by a thermal process to the garment, e.g., using a layer of adhesive.

One or more conductive threads may be applied directly to a fabric (such as a compression garment) or to a transfer (e.g., patch of fabric or other material that is then attached to the garment). Conductive threads may be insulated (e.g., enameled) before being sewn. In some variations the conductive thread may be grouped prior to sewing onto a fabric or other substrate. For example, a plurality (e.g., 2, 3, 4, 5, etc.) of threads may be insulated and wound together, then stitched into a substrate, such as the compression fabric. For example, in one variation, an apparatus includes a garment having an IMU and two EMGs with inputs fed into circuitry (e.g., microchip) on the apparatus, including on a sensor module/manager. The components may be operated on the same electronic 'line', where the line is a a plurality of electrically conductive threads that are combined together for stitching through the substrate. In one example, two microchips can be operated by the same 'line' made of 4 wires, where each wire is electrically isolated from each other. In stitching a material, the stitch may be formed of two sets of wires; one on top of the substrate and one beneath the substrate, as is understood from mechanical sewing devices; in some variations a stitch formed of conductive thread may include an upper conductive thread (or group of conductive threads) and a lower conductive thread (or group of conductive threads), where the upper conductive thread(s) is primarily on the upper surface and the lower conductive thread(s) are primarily on the lower surface (but one or either may pass through the substrate to engage with the other).

For example, a conductive thread may include a very fine (e.g., 0.7 millimeters gauge/thickness) 'wire' made of 4 twisted and enameled (thus electrically isolated from each other) wires covered with a binding solution (that is silicon or water based) or protected by a jacket, having a total diameter of about 0.9 millimeters. A conductive wire may be sewn in a wavy (e.g., zig-zag) pattern, such as a pattern having 45 to 90 degrees angles between the legs of the zig-zag, directly on a fabric or substrate. In some example, the pattern is formed on a substrate of material (e.g., fabric) and attached to the garment. For example, the substrate may be a 1 cm to 3 cm self-adhesive strip of fabric.

Figure 41:
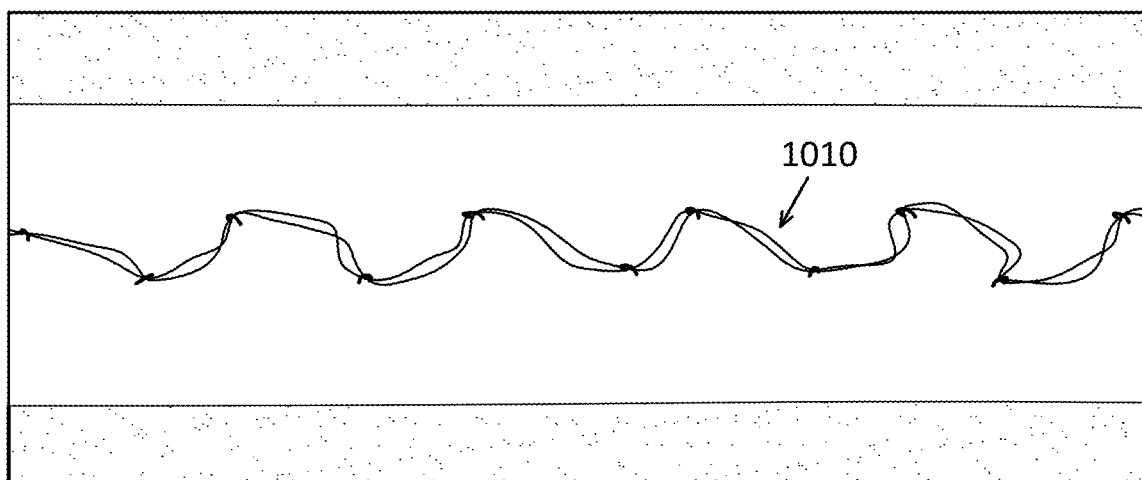
FIG. 41 illustrates one example of a wired ribbon (an elastic electrical connector) that may be used to connect a stretchable fabric.

FIGS. 41-48 illustrate the connection and formation of one type of sensor to an elastic electrical connector as described above. In this example, a stretch sensor may be formed by impregnating an elastic material with conductive particles, allowing it to dry and then coupling contacts at the ends, to form terminals. Once the terminals are attached, the elastic material may be coupled to a wire connector, such as the pre-prepared wire ribbon material shown in FIG. 41. In FIG. 41, a wire ribbon material is sewn into a strip of fabric with a pair of twisted wires 1010 (though more than two wires may be used), shown as twisted, enameled (insulated) wires. The wires are sewn into the strip of fabric (e.g., compression fabric) in a zig-zag pattern and the fabric strip may include a fabric adhesive or may be configured for thermally applying to another fabric (e.g., garment), so that the conductive connectors can be applied directly to the fabric without having to sew directly onto the fabric, and providing a covering for the wires. The fabric onto which the wires are sewn is typically the same material to which they are to be applied (e.g., a compression garment fabric). In some variations one side of the fabric onto which the zig-zag pattern of insulated wires is sewn, which may be referred to as an applicator fabric, include or is treated for use with a fabric adhesive (including thermally active adhesive). In practice, long lengths of wire may be prepared ahead of time and cut to need for application to a garment. Note that in general, a wire ribbon material may be used as an electrical connector connecting one or more sensors to other portions of the garments described herein, including a data module, and/or an SMS component. This wire ribbon material may be referred to herein as a wire ribbon material or as a stitched zig-zag connector. This material may be advantageously prepared in long lengths and cut to the desired length for securing (e.g., adhesively securing) the garment and/or sensor.

Figure 42:
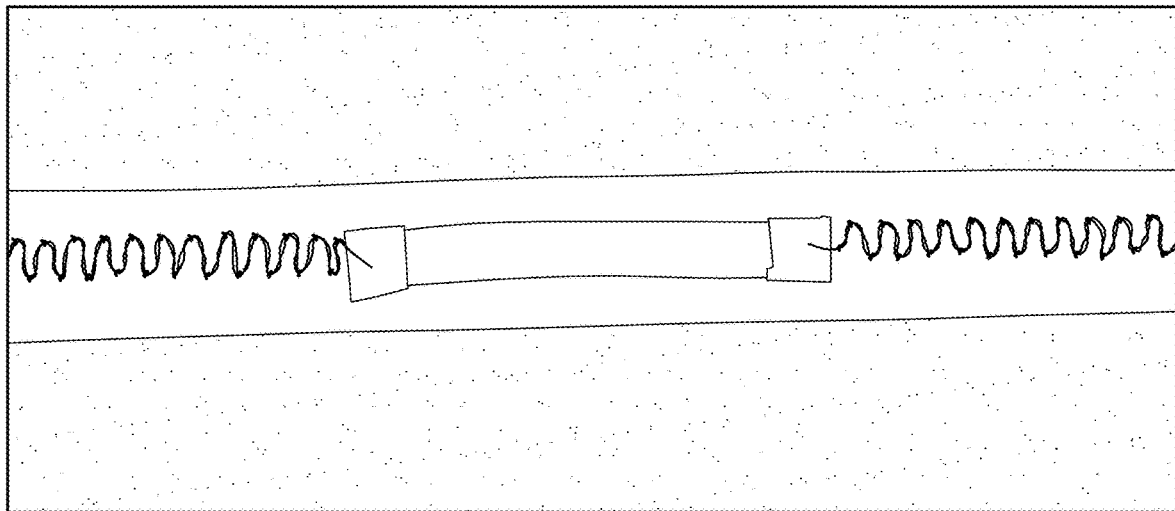
FIG. 42 illustrates the attachment of a conductive elastic ribbon formed as shown in above, to a stretch sensor using two wires from the elastic electrical connector.
Figure 43:
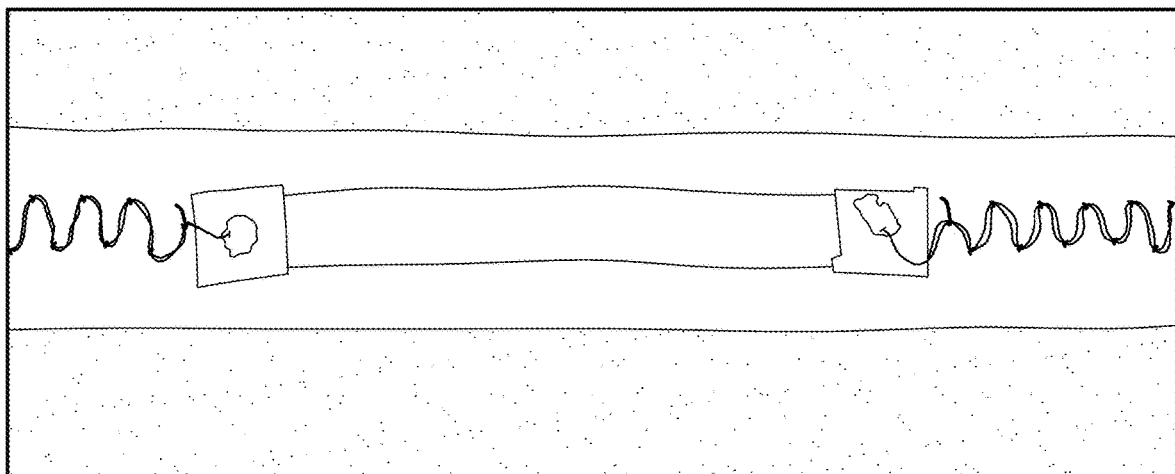
FIGS. 43, 44 and 45 illustrate one method of making a sealed conductive ribbon (elastic electrical connector) including a stretch sensor coupled to an elastic electrical connector.

For example, in FIG. 42, the conductive elastic ribbon is place on a thermo adhesive glued surface of the wired ribbon in a region that does not include wire, and connected to the conductive wire ends. For example, as shown in FIG. 43, the conductors (wires) are soldered to the copper terminals.

Figure 44:
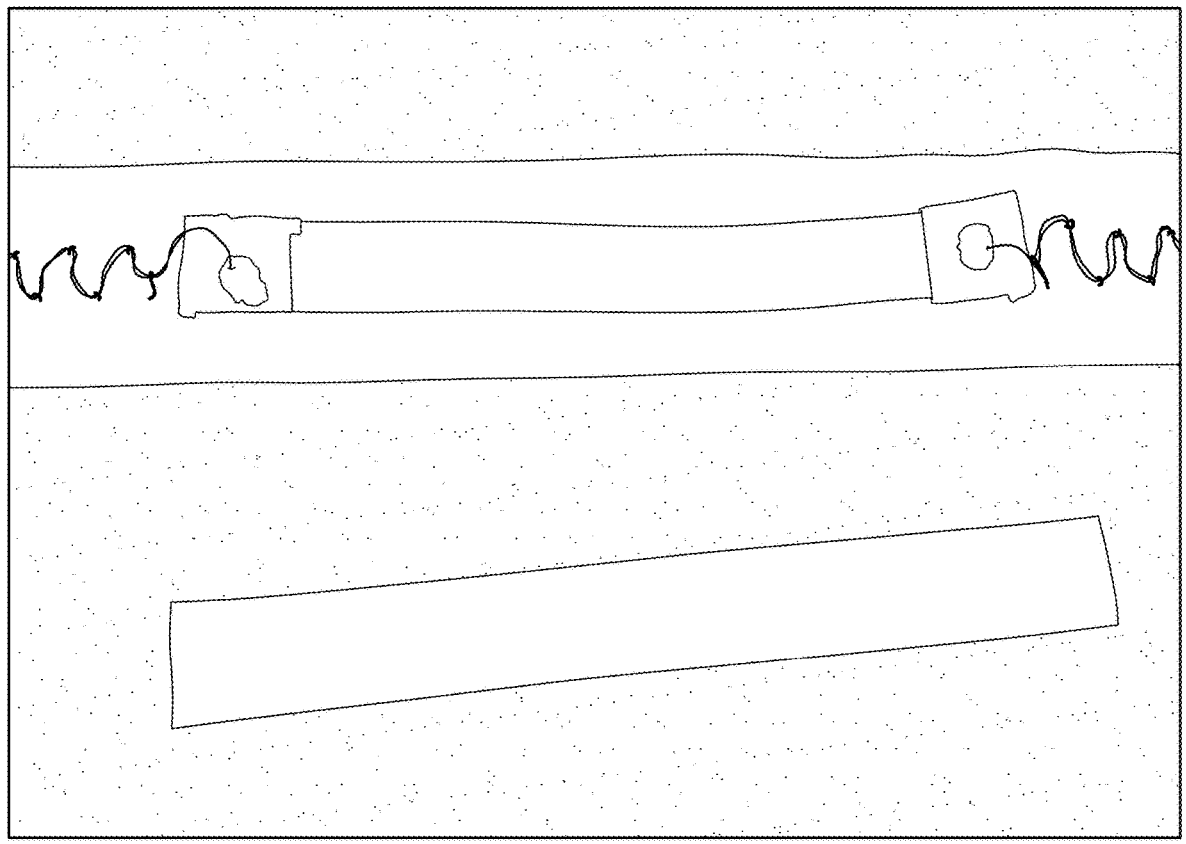
Figure 45:
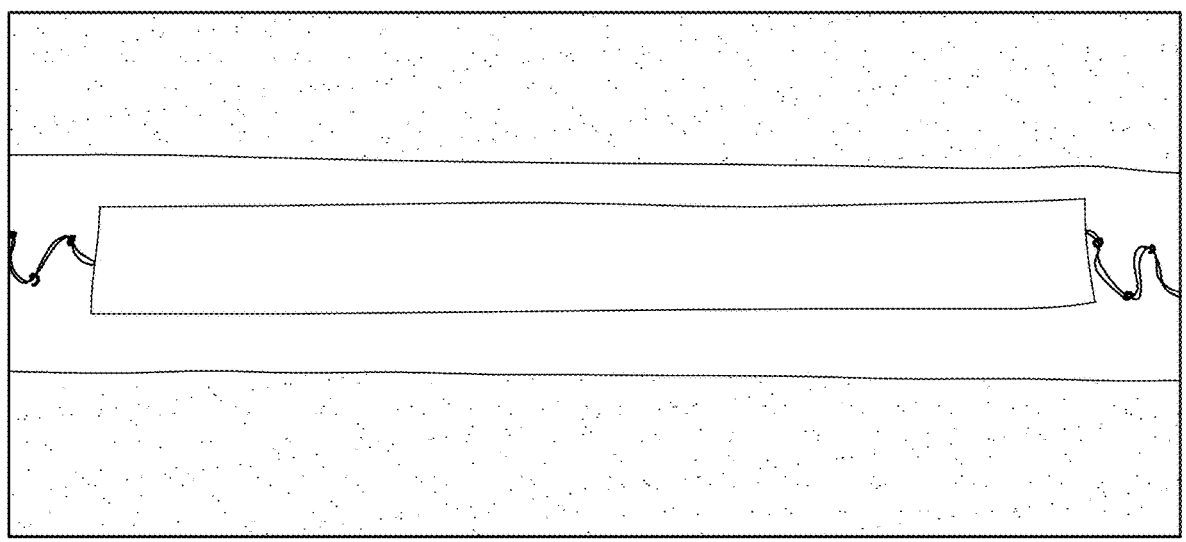
Figure 46:
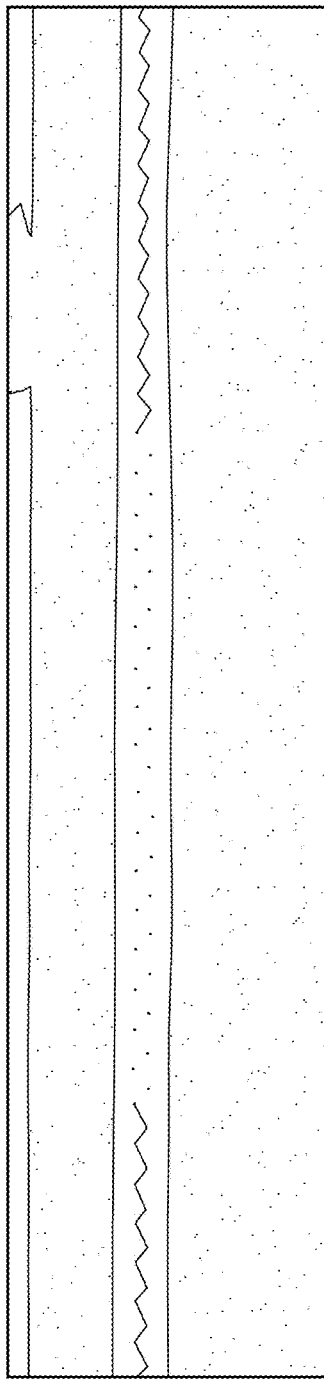
FIGS. 46-48 show examples of elastic electrical connector that may be adhesively attached to a garment to connect multiple electrical components.
Figure 47:
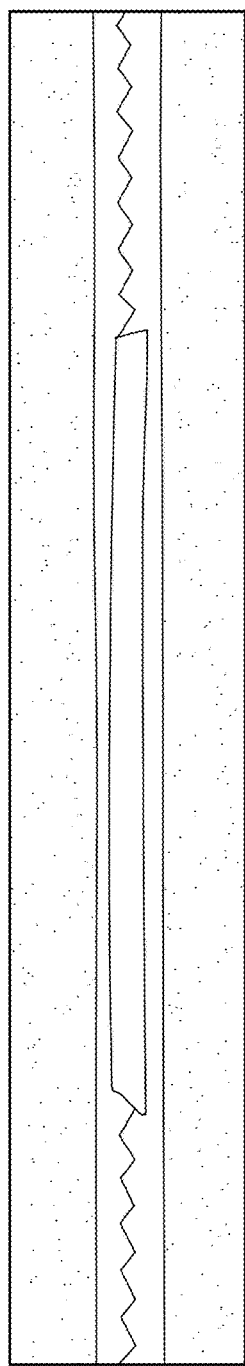
Figure 48:
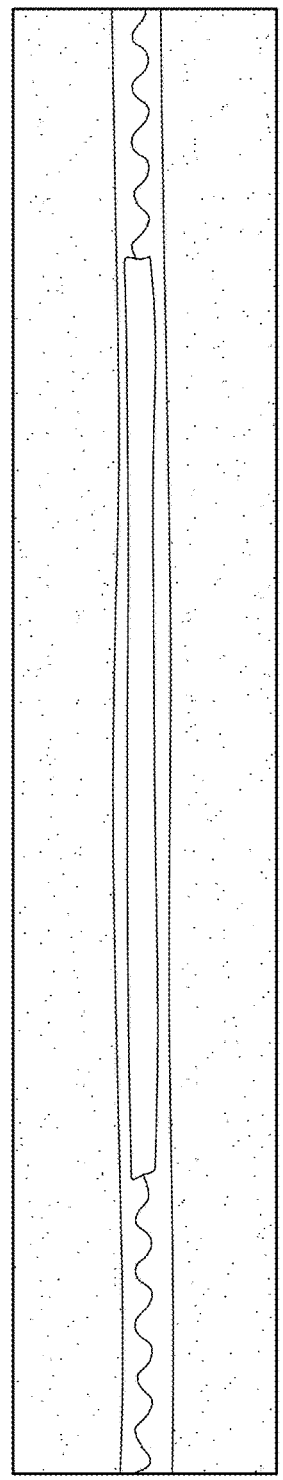

Once applied to the conductive wires, the elastic ribbon may be enclosed within a fabric (e.g., an insulating fabric, which may be the same as the fabric to which it's being applied). In some variations the elastic ribbon may be enclosed in an insulator material and/or coated with an insulator. In FIGS. 44 and 45 the external side of the conductive elastic ribbon (including the contacts) is sealed with an adhesive tissue ribbon to a width of approximately 33 mm). The tissue (covering) ribbon may be fixed over the elastic ribbon by, e.g., thermo press (when using a thermally activated adhesive) as shown in FIG. 45.

Thereafter, the resulting ribbon including the conductive elastic material and zig-zag wires may be attached to a garment, such as a compression garment.

Figure 49:
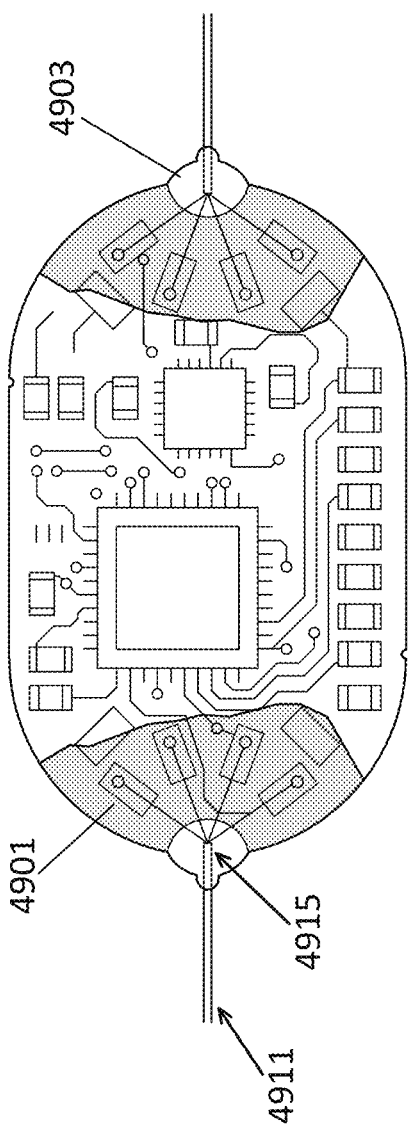
FIG. 49 illustrates one example of a sensor (e.g., inertial measurement unit or IMU) that may be attached to an elastic connector for a wearable apparatus (garment). In this example, the IMU is attached by multiple wires (eight attachments, four per side, are shown).

FIG. 49 is an example of a sensor that may be integrated into an elastic connector as described herein. In this example, the sensor is an IMU, although any sensor may be used. Multiple IMUs may be attached to the subsystem (as shown in FIGS. 35A and 35B), which may provide body movement and/or positional information when the garment is worn. For example a sensor may be on or part of a printed circuity board such as the IMU shown in FIG. 49 (or an EMG sensor or conditioning circuitry). Attachment between a flexible, stretchable fabric and a somewhat more rigid PCB may typically result in a poor connection which may vary in resistance as the wire(s) is/are bent during normal movement/wear of the garment. In FIG. 49, the PADs 4901 onto which the insulated wires of the connector are attached are arranged in a fanned, semi-circular arrangement, so that the wires may remain bundled 4911 until they reach the center of the semi-round seating region (e.g., remain gathered together), as shown, then individual wires spread out and are attached to the contacts (PADS 4911). Similar connections may be made on both ends of the circuitry. In some variations wires that are not connected to the circuit (e.g., sensor) may be separated before reaching the fan-out region at the vertex 4915 of the semi-circular PAD arrangement, and may pass on the strip, around the sensor/circuitry (not shown).

Figure 50:
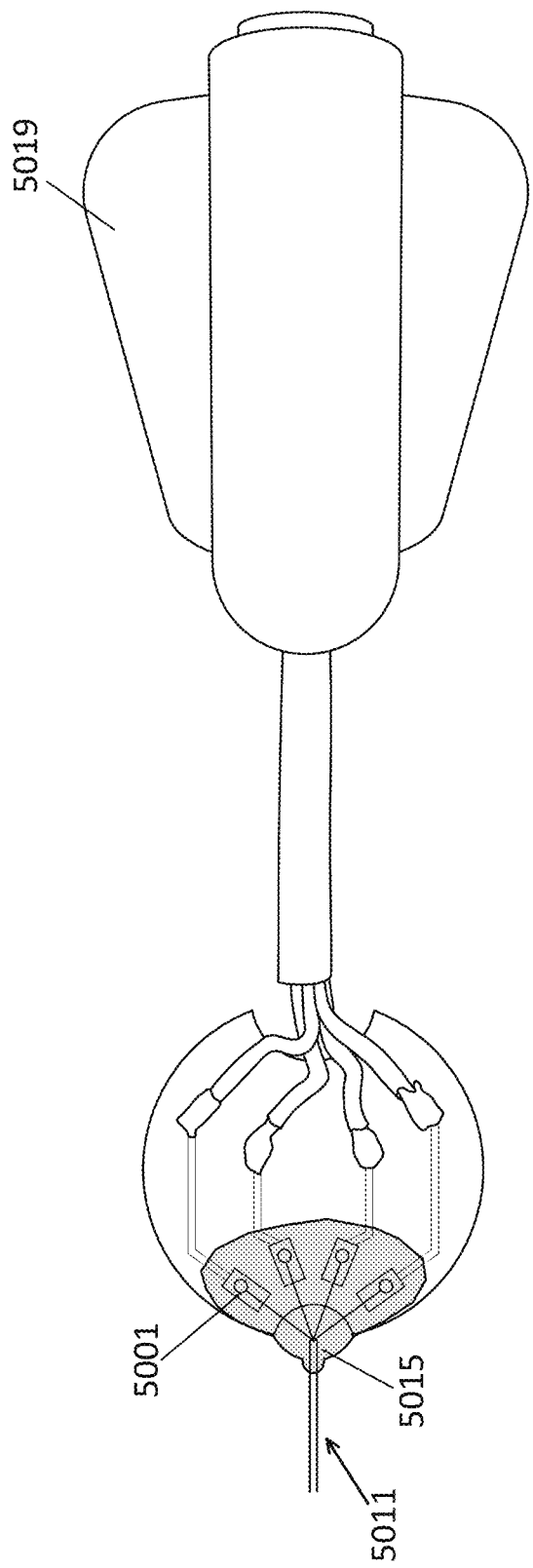
FIG. 50 shows an exemplary connection of a PCB (printed circuit board) and a jack (e.g., female jack connector) to an elastic connector.

FIG. 50 is another example of a circuitry (PCB) that may be connected in a similar fashion to the flexible/stretchable fabric connector strip. In FIG. 50, a female plug 5019 may be connected to the strip. The female jack connector in this example includes two added wings that may improve the Jack connector stability and the fixing to the ribbon. In this example, the insulated wires from the connector strip remain bundled 5011 until they reach a central vertex region 5015, where they then fan out to contact the PAD contacts arranged in a semi-circle that fans out around a common vertex 5015. By connecting the wires of the flexible fabric strip to the more rigid substrate and contacts of a sensor or other PCB (e.g., the connector 5019 shown in FIG. 50) in this manner, stress may be distributed in a way that prevents resistance changes and disconnection of the wires.

It may also be beneficial to coat the contact region (including the vertex 4915, 5015 and PAD contacts 4909, 5009) with a polymer, such as a silicone. For example, in both FIGS. 49 and 50, a Dow Corning silicone has been placed in the circular seat wire connector regions, keeping the wires in suspension so that they may exit gently from the PCB as a cable boot. The silicone may be accurately and easily applied because of the semi-circular arrangement, and may help insulate and protect from water as well.

In FIG. 51, the sensor (e.g., IMU 5103) and circuitry (processor 5105 with connector 5107) such as those shown in FIGS. 49 and 50 are shown connected to a flexible fabric connector, as illustrated above. In this example, the fabric (e.g., compression or stretchable fabric) 5101 is formed as a strip and has an adhesive on one or both sides (e.g., on the visible side shown in FIG. 51). As just described, both the sensor and the connector, via the circuitry 5105, are attached to some of the wires coupled to the fabric in a zig-zag pattern, as shown.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Additional Examples

The methods and apparatuses described herein may be configured for use with or as part of a wearable electronics garment that includes a plurality of sensors. One improvement described herein is the use of a strip of fabric, configured as a framework that includes wiring and sensors preformed and connected thereon. The framework may be made attached into a garment, and allows flexibility in construction, testing and finishing. As described above, the framework includes strips or ribbons of substrate, which may be the same or a different material from the rest of the garment to which it is attached. These ribbons may include wire bundles that are then connected to the sensors and/or outputs on the strips and attached to the garment. Rolls of the wired ribbon (with flexibly and slideably attached zig-zag wire bundles) may be formed and variable lengths later cut and used to form a variety of garments having different shapes and sizes.

Figure 52A:
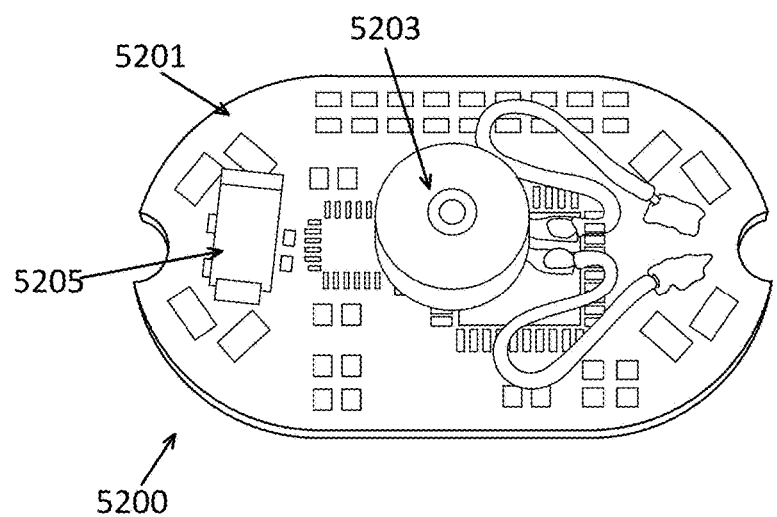
FIG. 52A shows another example of a haptic actuator attached to a substrate (e.g., in this example, PCB) that may be integrated into a garment, as shown in FIG. 52B.
Figure 52B:
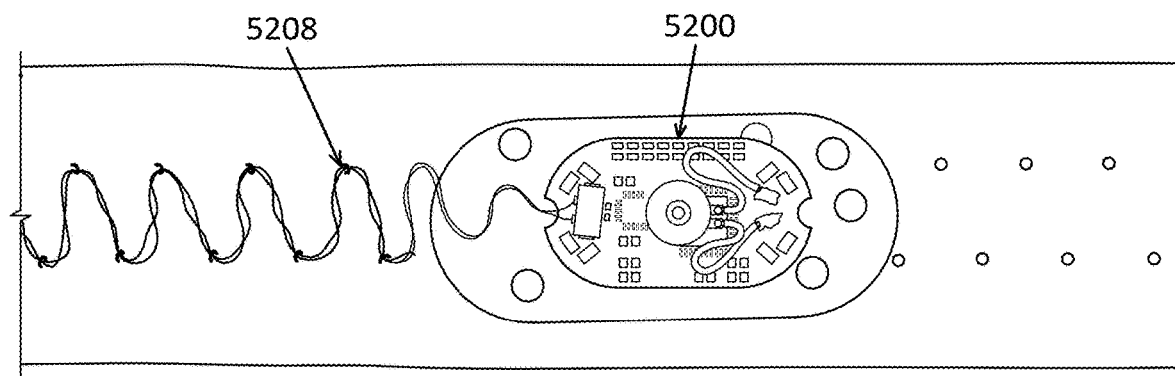
In FIG. 52B the haptic actuator and substrate at attached to a strip of wired fabric, as described above; this strip, including the sensor (haptic sensor) may be integrated into the garment as part of the pre-wired strip of material.

In addition, the ribbons including the flexible and slideable bundles of insulated wires may also have one or more sensors and/or outputs (e.g., electrodes, haptics, accelerometers, temperature sensors, speakers, capacitive touch sensors, etc.) formed on the strip of material or attached to an adjacent strip of material. For was illustrated above in FIGS. 6-9, 16 and 31-32, 35A-35B, 42-45 and 51. FIGS. 52A-52B illustrate another example, showing a haptic actuator that may be included. In FIG. 52A, the haptic actuator 5203 is shown on a substrate (e.g., PCB, which may include a protective coating such as a transparent resin coating) 5201, and is assembled on the substrate with component circuitry, such as a filter diode 5205 and control circuity. As show in FIG. 52B, the haptic actuator assembly on the substrate 5200 may be connected to the ribbon or strip including the electrical connectors arranged in a zig-zag pattern 5208 as previously described. Thus any of the ribbons described herein may be formed with one or more sensors and/or outputs connected to the conductive wires arranged on the ribbon. These may then be joined into the framework when assembling the device, such, for example, the framework ("spidon") shown in FIG. 53.

Figure 53:
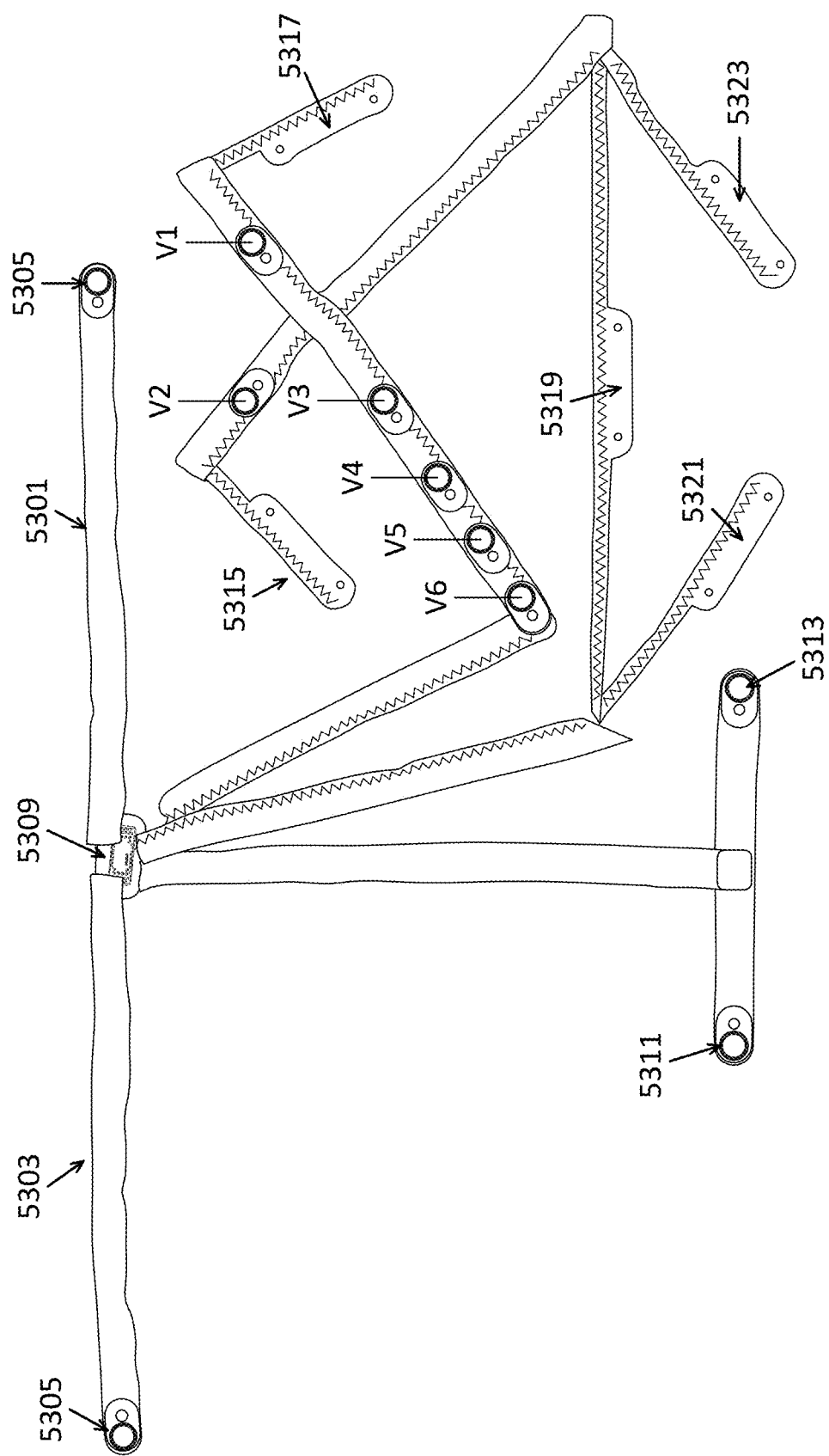
FIG. 53 is an example of a wiring and sensor framework/subsystem (spydon subsystem) including multiple elastic electrical connectors that each contain a plurality of conductive wires connected or connectable to multiple different electrical components (e.g., sensors). The subsystem forms a branching framework of strips that are connected to a controller/processor (e.g., via an SMS connector) and may be flexibly and readily integrated into a variety of differently sized and configured garments. The branches network of connected sensors may be adhesively and/or otherwise transferred to the fabric to form a wearable garment.

FIG. 53 shows an example similar to that shown and described in FIGS. 35A-356B, discussed above. In FIG. 53, the framework is formed by cutting strips of connector ribbon to which one or more sensors have been coupled to a desired length and arranging them in the framework to be attached to the garment. In this example, the framework includes lengths of ribbon to which bundles of insulated wire are attached as discussed above, and conned to t electrodes or other sensors. For example, left 5301 and right 5303 arm strips of ribbon each have an electrode 5305, 5305' on either end. Each strip may ultimately electrically connect to an SMS unit 5309 for processing/storage/transmission of data from the sensors and/or outputs. Other branches of the framework formed by the connected ribbons include right 5311 and left 5313 leg electrodes as well as left 5315 and right 5317 thorax breath sensors that are configured to be attached across the front of the garment. An abdominal breath sensor 5319 as well as left 5321 and right 5323 abdominal breath sensors may also be included to detect respiration. In FIG. 53 the chest strips also include a plurality of ECG electrodes (V1-V6) arranged to detect ECG at or near standard ECG electrode placement positions.

Any of the electrodes for contacting the wearer's body described herein may be configured as an assembly of electrodes. For example, FIG. 54A-54B illustrate an embossed electrode configured for EEG, EOG, EMG and/or ECG. In FIG. 54A the electrode assembly is shown in an exploded view including an electrode cover 5401, a conductive ink 5403, an electrode support 5405, a compressible contact support 5407 (shown here as a sponge foam for increased contact to skin and therefore conductance). And an electrical limiter (e.g., insulator) 5409. FIG. 54B shows an example of a partially assembled electrode 5411, without a cover.

Any appropriate covers may be used. The electrode cover may be particularly helpful to keep the electrode in contact with the wearer's skin. For example, FIGS. 55A and 55B illustrate electrode covers that are configured to include a grip pattern on the surface. In this example, the electrode covers are formed of a fabric material onto which a pattern of micro protrusions (e.g., balls, spheres, etc.) of a high-grip material such as silicone or polyurethane material has been applied by an extrusion or print process. These micro balls may help assure a good adhesion of the electrode to the skin in order to have a stable biometric signal. This pattern may also allow the sweat to drain from the skin surface (e.g., a pattern having gaps, rows, columns, etc.) as shown. The gaps may be spaced to be >0.1 mm (e.g., 0.1 mm or more, 0.2 mm or more, 0.3 mm or more, 0.5 mm or more 1 mm or more, etc.) apart. In FIG. 55A, the fabric support 5501 is a soft fabric support with an adhesive on (or may be applied onto) one side. The cover includes a window 5503. As mentioned, the plurality of grip protrusions 5505 may be attached or formed onto the skin-facing surface. FIG. 55B shows a similar variation with a larger window or opening for the electrode.

Figure 56B:
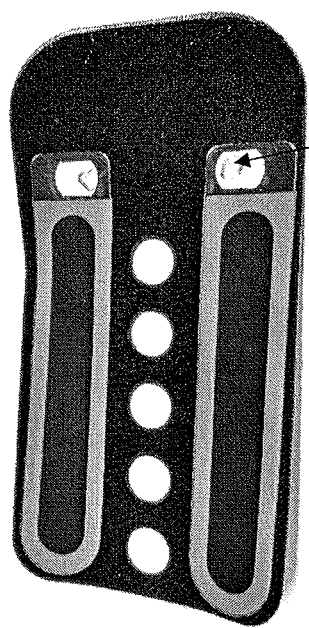
FIGS. 56A-56C illustrate a method of electrically connecting an array of electrodes.
Figure 56C:
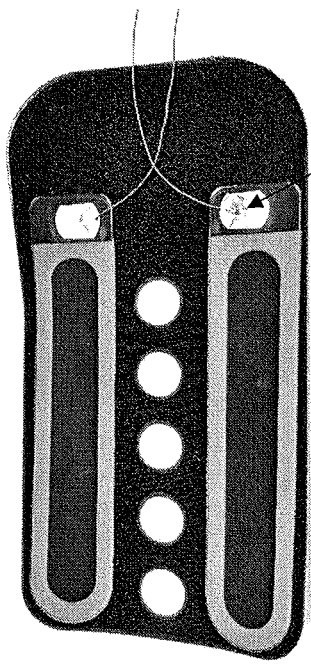
Figure 56A:
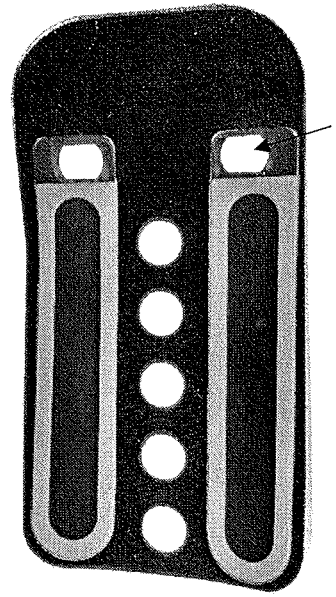

As mentioned, sensors, such as electrodes, may be attached to the electrical connectors on the strips/ribbons of material and used to form the framework for attaching to the garment. FIGS. 56A-56C illustrate one method of attaching a set of electrodes, similar to that shown in FIGS. 17A-20, above. In FIG. 56A, the conductive metal pads 5601 may be stuck onto the ink aps of the electrodes, as shown. These conductive metal pads may then be tinned 5603 (as shown in FIG. 56B) and a de-insulated end of the wires may be soldered 5605 to the conductive metal pads, as shown in FIG. 56C.

Figure 57:
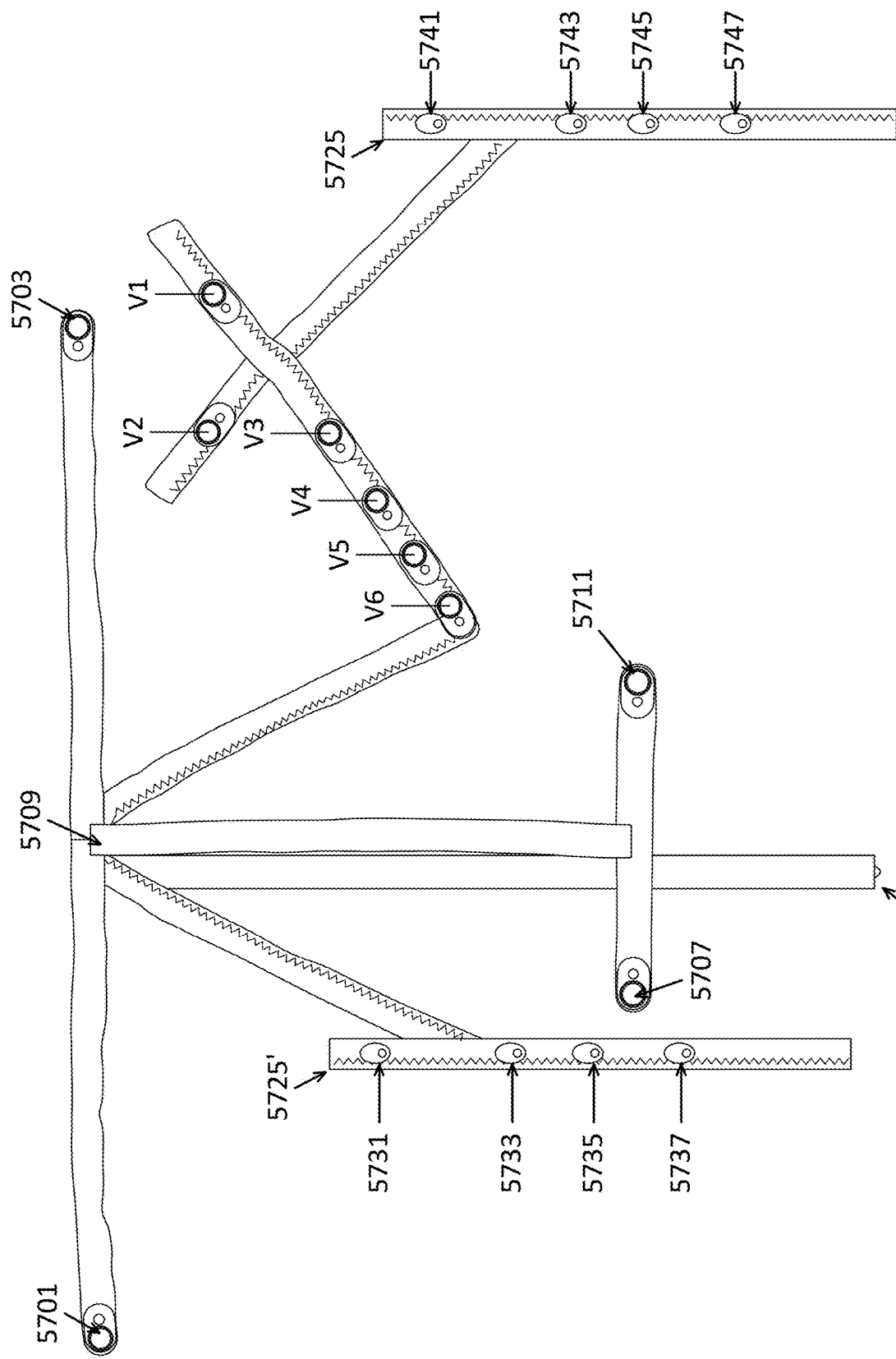
FIG. 57 is an example of a wiring and sensor framework/subsystem (spydon subsystem) including multiple elastic electrical connectors that each contain a plurality of conductive wires connected or connectable to multiple different electrical components (e.g., sensors). The subsystem forms a branching framework of strips that are connected to a controller/processor (e.g., via an SMS connector) and may be flexibly and readily integrated into a variety of differently sized and configured garments. The branches network of connected sensors may be adhesively and/or otherwise transferred to the fabric to form a wearable garment.

FIG. 57 is another, somewhat alternative, versions of the framework for forming a garment having a plurality of sensors similar to what is shown in FIG. 53. In FIG. 57, an alternative respiratory sensor is used, formed of a conductive cord, as will be described in greater detail below in reference to FIGS. 58A-58I. In this example, the apparatus includes the right 5701 and left 5703 arm electrodes and SMS 5709, as well as the right 5707 and left 5711 leg electrode (which may connect the lower back or upper buttock region when worn in the garment). Similar ECG electrodes (V1-V6) are shown. A plug 5721 (e.g., 5 pole female plug) may also be included. The respiratory sensors in this example, include ends that are connected by two parallel strips 5725, 5725' with ends at the level of the thorax, xiphoid, abdominal upper region, and abdominal lower region. The conductive cord, which is an elastic conductive cord, may be attached at either ends (e.g., between these parallel vertical strips 5725, 5725'). For example, the signal ends of the thorax 5731, xiphoid 5733, upper abdominal region 5735 and lower abdominal region 5737 are on the right side 5725' strip, while the ground end terminals of the thorax 5741, xiphoid 5743, upper abdominal region 5745 and lower abdominal region 5747 are on the left side strip 5725. As shown in FIG. 58A-58I the conductive cord may be connected between the signal and ground ends.

Figure 58H:
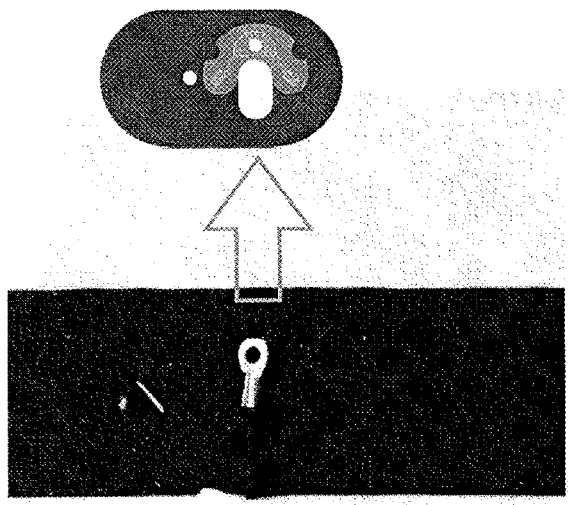
Figure 58I:
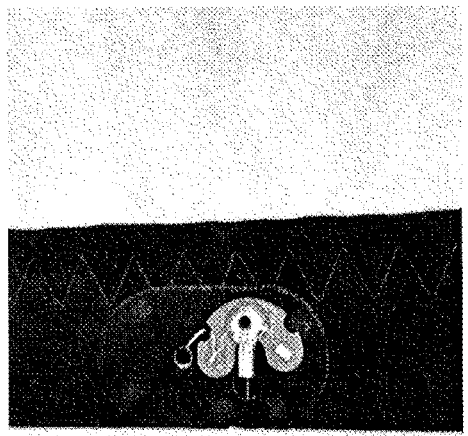
Figure 58G:
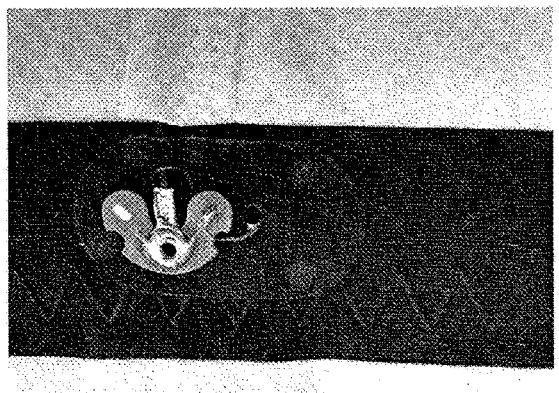

In FIG. 58A, a length of electrically conductive cord 5801 (e.g., a cord or tube formed of a conductive silicone rubber that includes an outer insulator) is shown. A connector (e.g., ring terminal) may be placed on either rend of the length. The length x may be cut to a predetermined length based on the size of the garment, and the terminals 5803 attached to either end (e.g., by crimping, etc.). The conductive cord may then be coupled to a support 5809 (with or without a rigid or semi-rigid substrate 5811, as shown in FIGS. 58C (and side view 58D) and 58E (and side view 58F). A connector 5813 (e.g. rivet) may be used to connect the conductive cord ends to the limiter support (substrate 5809). The other end may be pulled through a channel (e.g., a fabric channel that is attached or to be attached to the garment. The attachment end may then be coupled to the framework (e.g., FIG. 57) and an electrical contact made through the connector. See, FIG. 58G. The opposite end may then be connected to a support substrate and connector, as shown in FIG. 58H, and attached to the opposite strip (e.g., 5725' in FIG. 57), as shown in FIG. 58I. The connections may be sealed (and insulated). A fabric cover (sensor cover) may also be applied over the ends.

In operation, the electrically conductive cord may provide a stretch sensor that changes an electrical property (e.g., resistance) with stretch within a relatively linear range that provides a sufficient measure of respiration based on the stretching and relaxation of the cord during breathing while wearing the garment. The electrically conductive cord may include conductive carbon fibers.

Figure 60A:
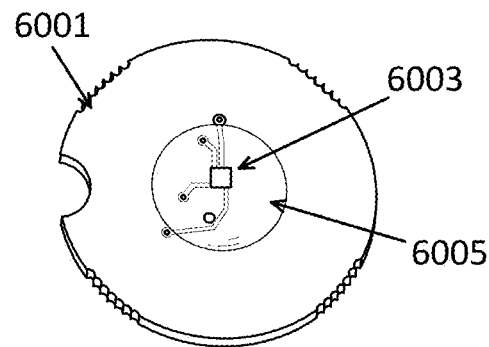
FIG. 60A is an example of a temperature sensor that may be included in any of the garments described herein.
Figure 60B:
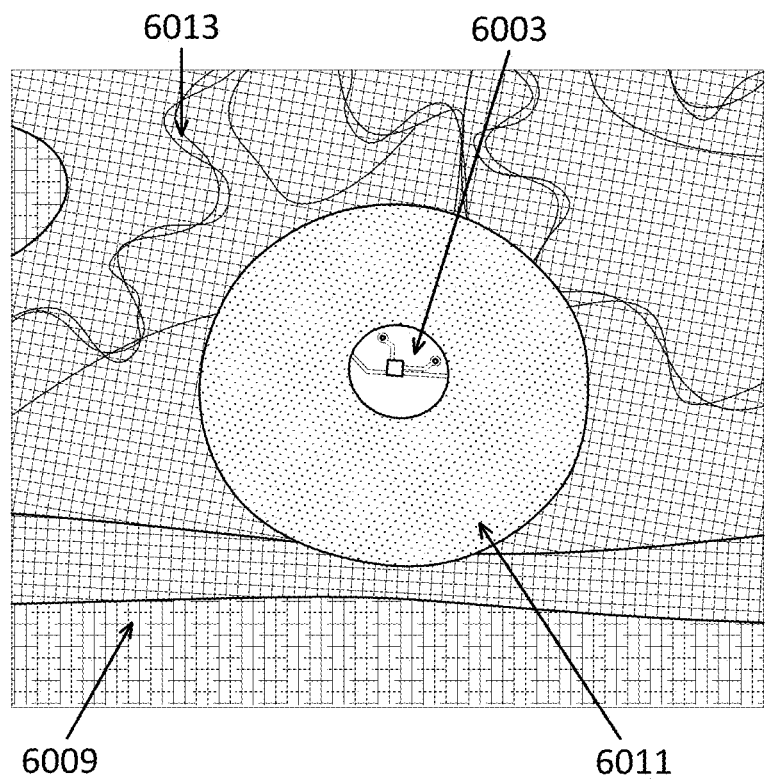
FIG. 60B is an example of the temperature sensor of FIG. 60A integrated into a garment.

FIGS. 60A-60B illustrate another example of a type of sensor, shown as a temperature sensor, that may be used. In this example, the temperature sensor is assembled on a rigid or semi-rigid support 6001 (e.g., PCB) and includes a temperature sensor 6003 (e.g., PCBA) and a transparent sealing cover 6005. In FIG. 6B the sensor is show integrated into a garment. For example, the sensor may be attached directly to the garment or to the strip/ribbon with the electrical connectors, as described above. In FIG. 60B, the sensor 6003 is connected to a transparent glue film support 6009 to which ultralight zig-zag bands of connectors 6013 have been attached as well, and a fabric ring protector cover 6011 is attached over the sensor.

Figure 61:
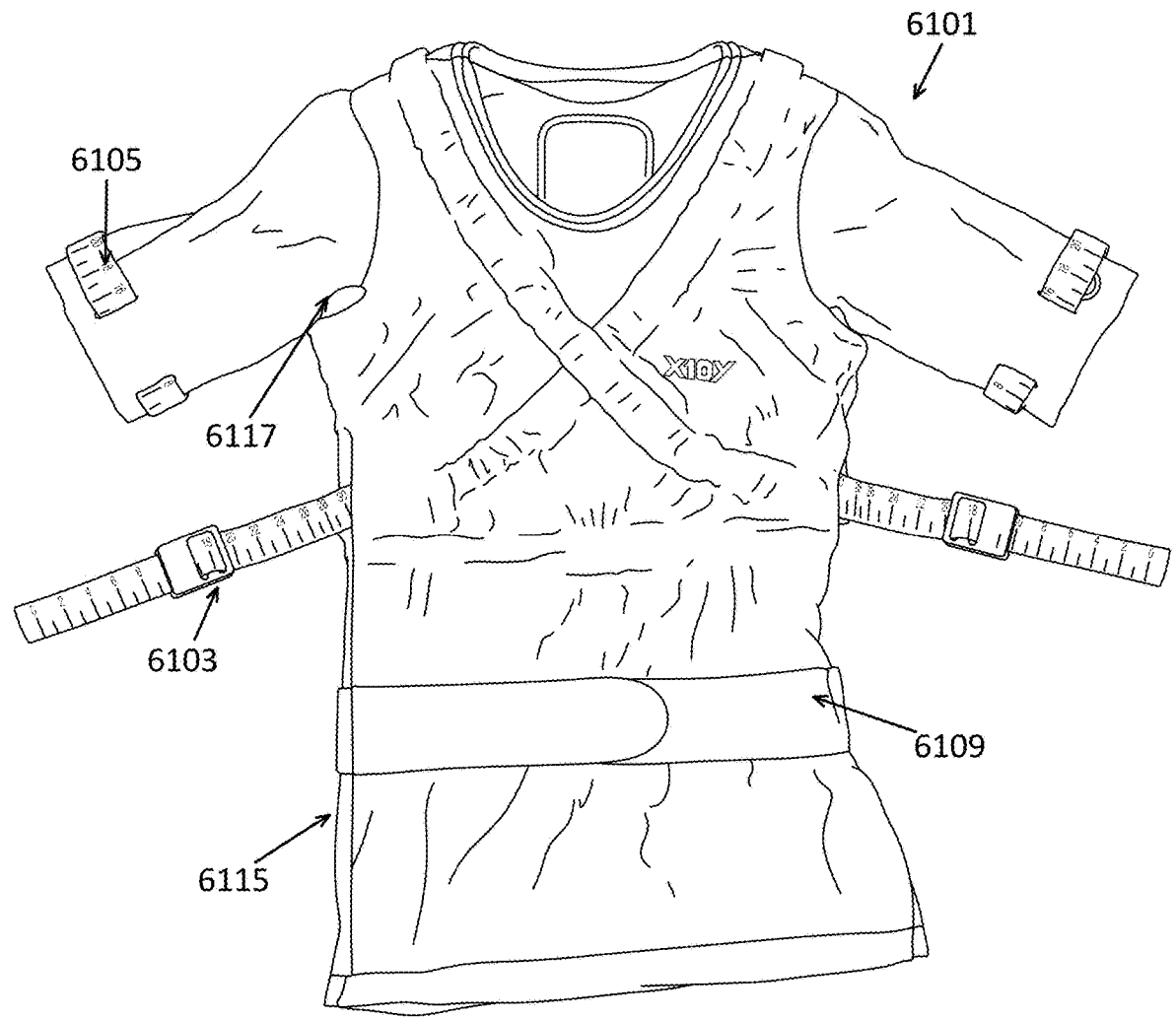
FIG. 61 is an example of a finished garment including the sensors described herein.

FIG. 61 shows an example of a finished garment 6101 that includes a framework of ribbons with conductive wires attached in a zig-zag pattern and sensors has been applied to a base fabric 6103 that is a compression material. The final garment also includes calibrated sets of straps 6103, 6105 for tightening halter-like framework to the patient's body, allowing snug contact with the skin, as well as a belt 6109. A side zipper 6115 may be used to put the garment on/off. The armpit regions are shown without fabric (opening 6117), to avoid getting perspiration on the garment, reducing the need to wash it, although it generally is washable.

Balaclava

Figure 62B:
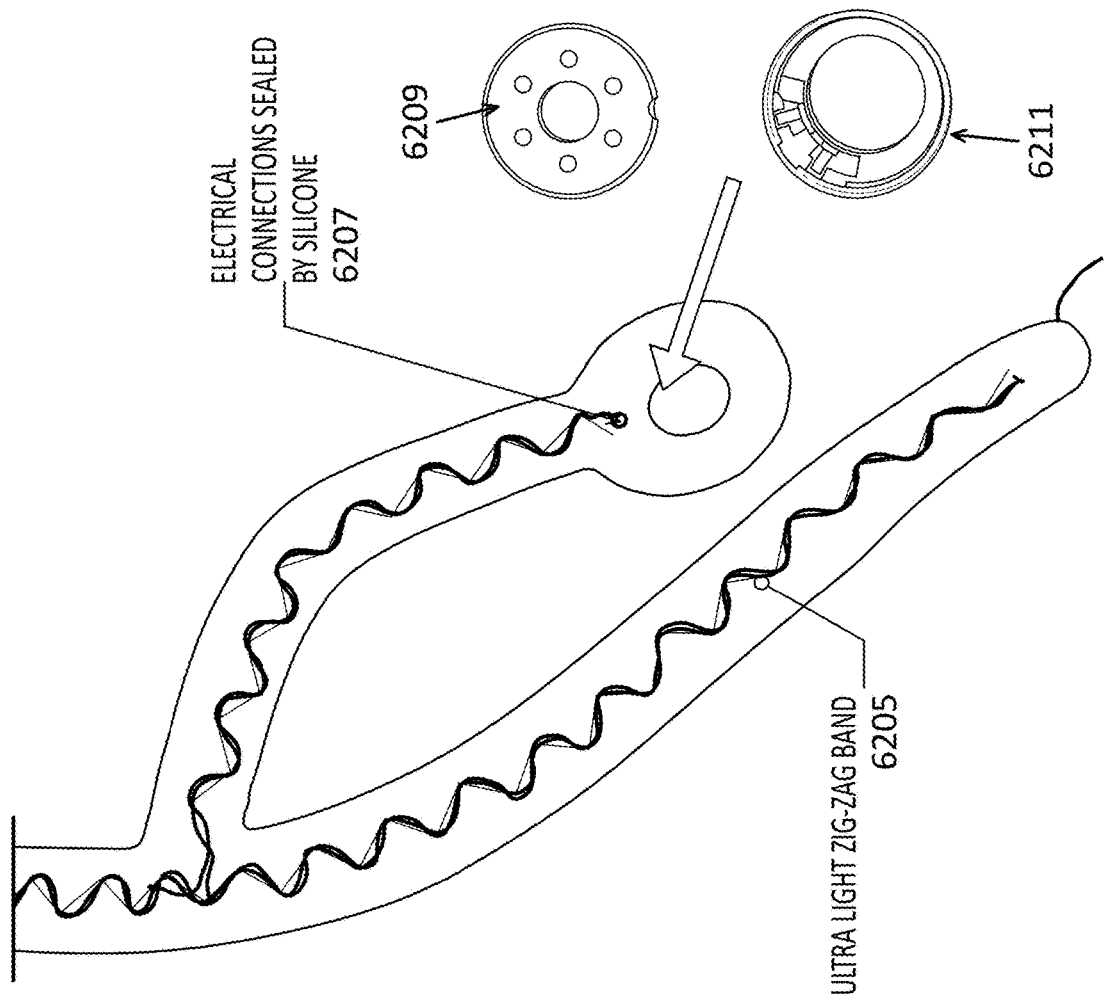
FIG. 62B is an enlarged view of a portion of the framework of FIG. 62A, showing the attachment site for the speaker and the zig-zag pattern of electrical connectors.
Figure 62A:
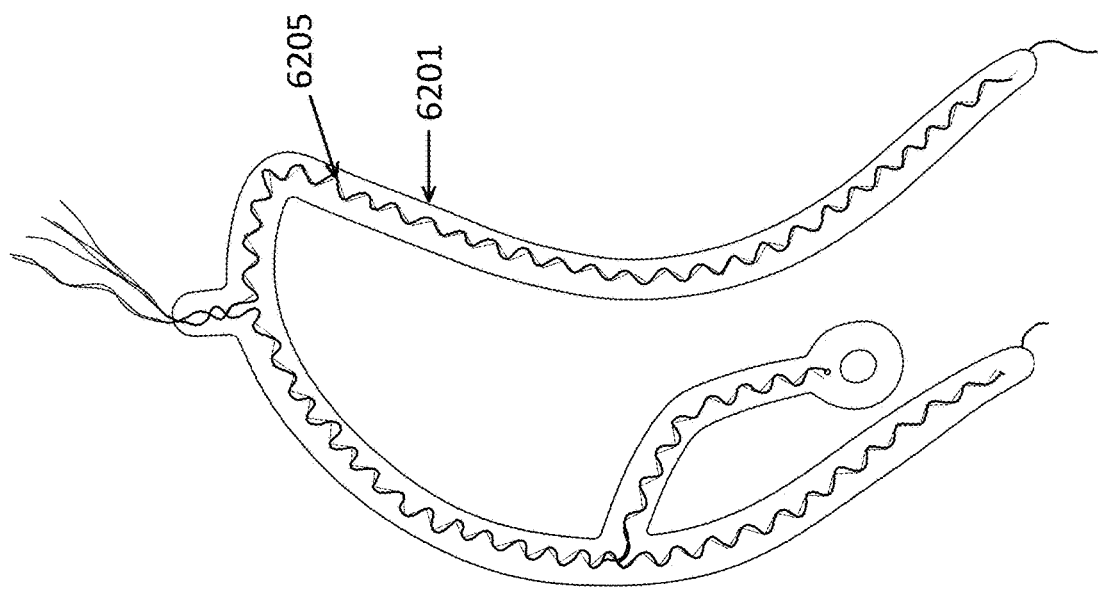
FIG. 62A shows one example of a portion of a wiring and sensor framework for a balaclava garment that may be worn on a user's head.

FIGS. 62A-69D illustrate one example of a garment with a plurality of sensors that may be worn by a patient. This garment is configured as a balaclava to be worn on the patient's head, and may include a variety of different sensor and/or outputs, including a speaker over or near the user's ear(s). The same principles described above, including the ribbons formed with bundles of insulated electrically conductive wires arranged in a zig-zag pattern may be used, and the ribbon may have a smaller width. FIGS. 62A and 62B illustrate an example of a framework ("spidon") for a balaclava garment. In this example, to increase the wearing comfort of the Balaclava harness/framework, a conductor distribution system including the zig-zag wire bundles is used; however these wires may be sewn directly on the fabric band. For example, the wires 6205 may individually or as a bundle be sewn first on a thin glue transparent ribbon and then applied to the fabric band on the glue side. The fabric band shown 6203 has been cut with a custom shape, both for left and right side, in order to avoid sharp bends. A speaker 6209, 6211 may be attached (in FIG. 62B, both the front 6211 and back 6209 views of a speaker to be attached to the electrical connections 6207 are shown).

In general, the balaclava apparatus may be part of a garment adapted for use when sleeping. Sleep has a critic impact on human health. Getting a good night's sleep is essential to feeling vigorous the following day. The challenge is to define what a "good" sleep is. Biometric signals can be exploited to infer indices of clinical relevance which describe the structure of the sleep, highlighting different phases, patterns, transient events and possible pathological conditions.

Figures 63A, 63B, 63C:
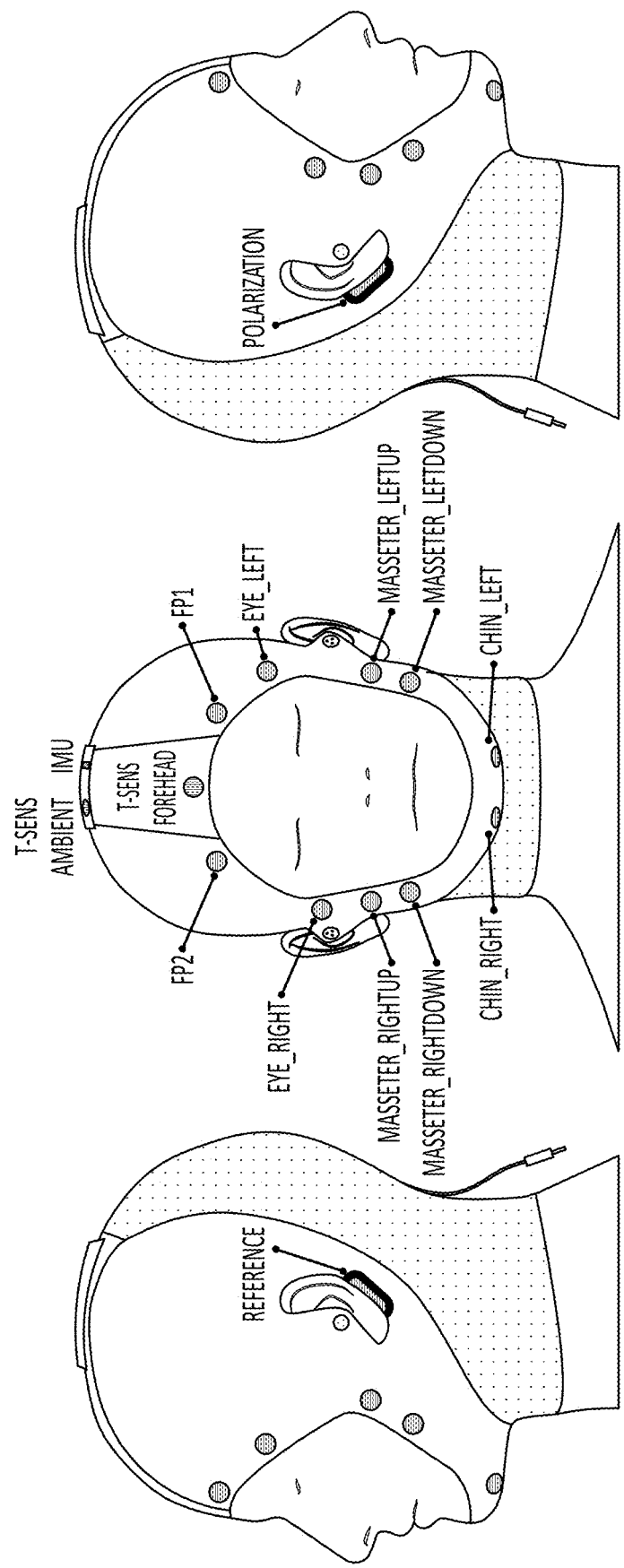
FIGS. 63A-63C illustrate left, front and right side views, respectively of a balaclava including a plurality of sensors that may be worn separately or as part of a system of garments including sensors.

The balaclava apparatus shown in FIGS. 63A-63C is a wearable device able that acquires biometric signals from the user's head, as well as ambient parameters, through a set of embedded dry electrodes and sensors. The acquired signals may include: EEG(2): two frontal channels, Fp1-M1 and Fp2-M1; EOG(2): left eye and right eye; EMG(3): chin, left masseter and right masseter; Head's position/motion; Frontal temperature; and ambient temperature.

The apparatus may be connected to additional garments measuring other body parameters, and may be a complementary tool for polysomnographic monitoring and sleep studies: the acquired signals are useful to implement a sleep report and to infer nocturnal unconscious behaviors. An additional feature of the apparatus is the possibility of providing relaxing, acoustic stimuli to the user or to stream music as a sleep aid, by exploiting a pair of embedded earbuds.

Figure 64B:
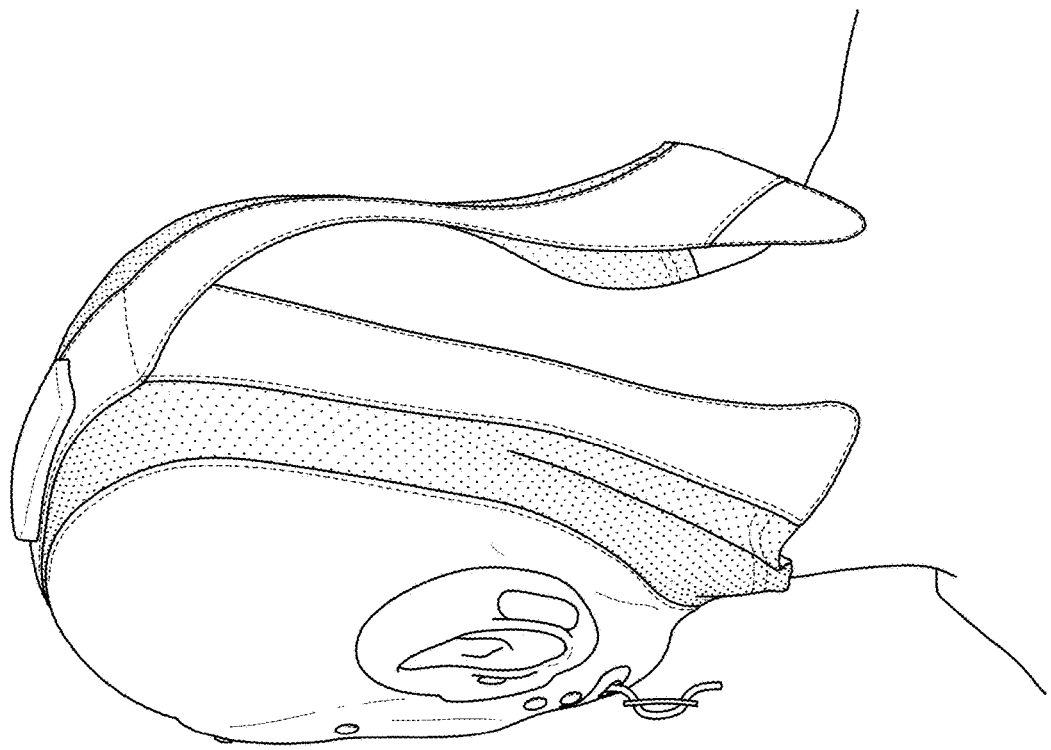
FIGS. 64A and 64B illustrate front perspective and rear perspective views, respectively, of a balaclava to be worn on a subject's head similar to that shown in FIG. 63A-63B.
Figure 64A:
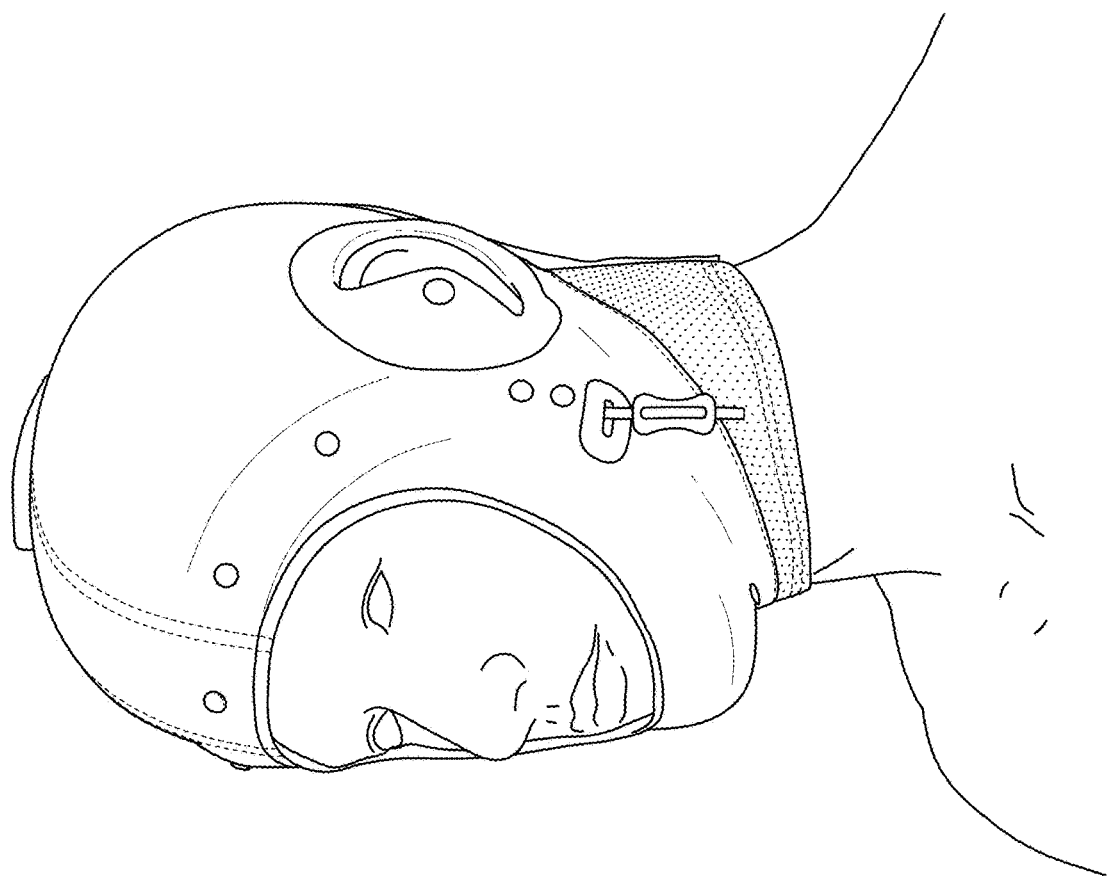

Target users may be subjects with either diagnosed or suspected sleep disorders, subjects who need a sleep aid or subjects who want to "quantify themselves" even in complete, unconscious conditions. FIGS. 64A-64B show front and rear perspective views of the apparatus worn on a user. The garment is configured as a fitting cap which completely covers the user's head except for eyes, nose, mouth and the back of the head. The cap has an opening on the nape with an adjustable fastening mechanism. This element allows for easy wear ability: the user wears the Balaclava by inserting their face into the large opening on the back, then gently fits the fabric over the face and head, finally fastening the mechanism on the nape according to his particular neck size.

Figure 65B:
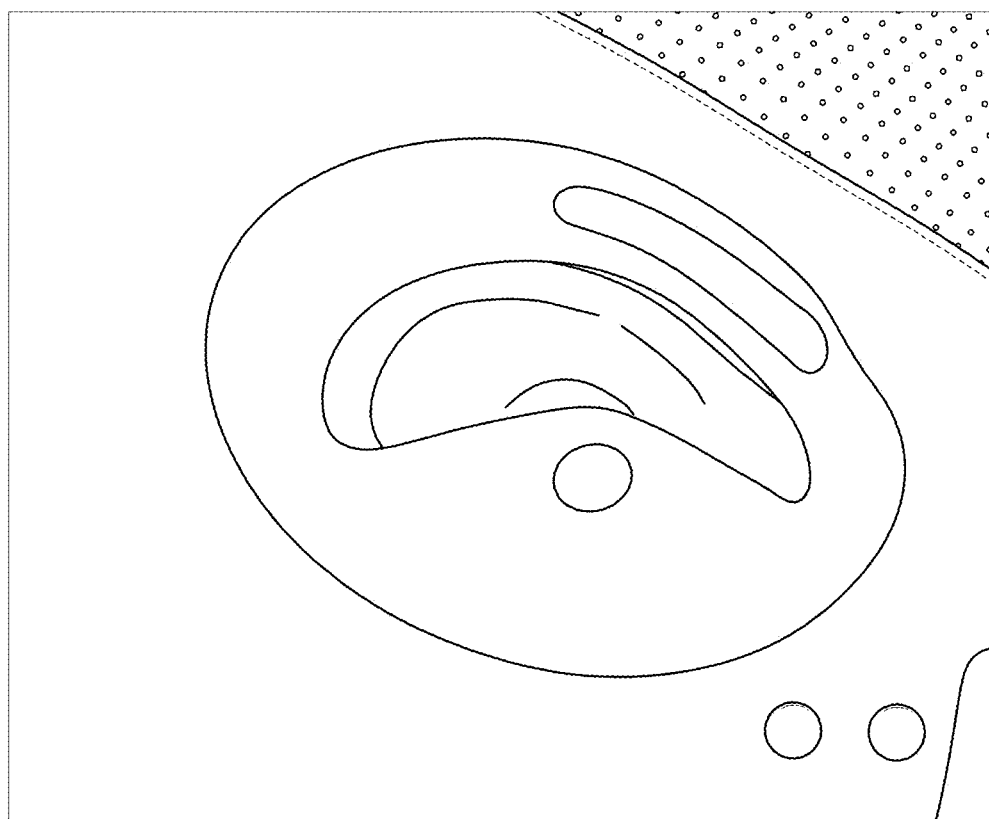
FIGS. 65A and 65B show rear and left size views, respectively, of the balaclava device of FIGS. 63A-64B.
Figure 65A:
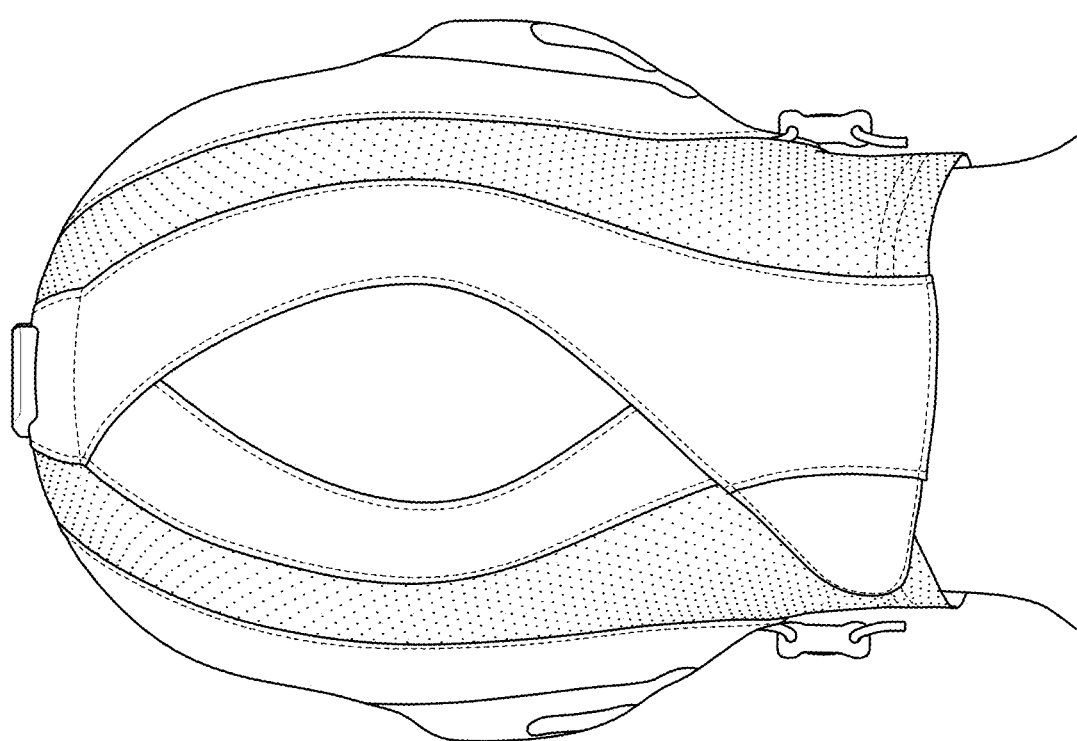
Figure 66B:
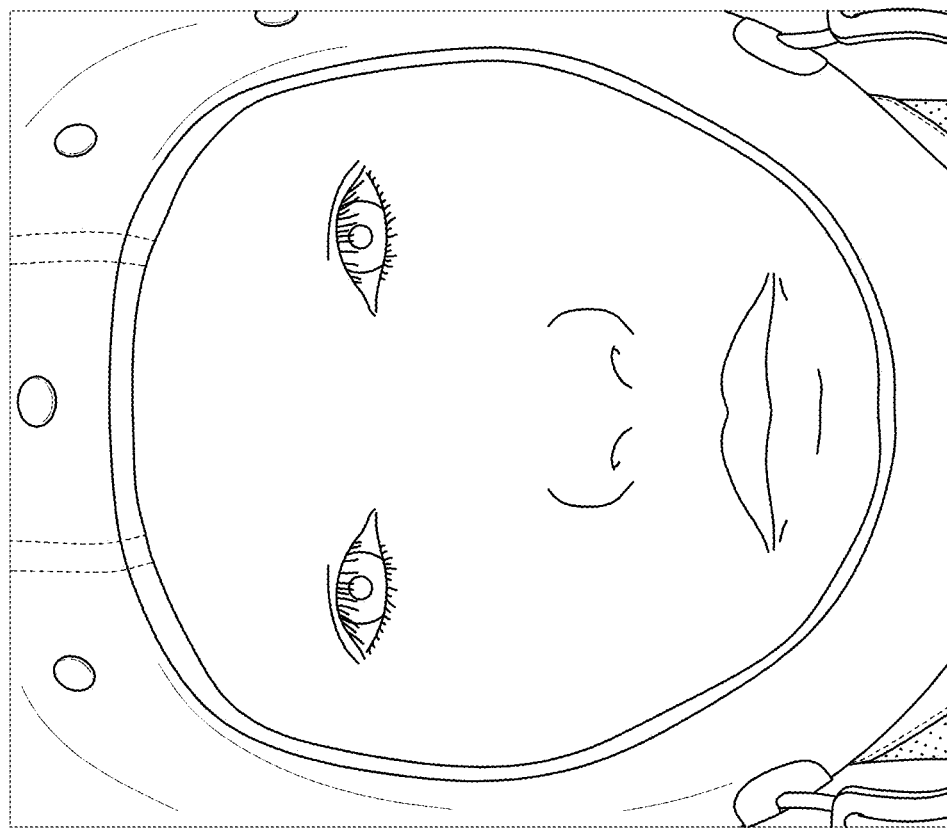
FIGS. 66A and 66B show right and front views, respectively, of the balaclava device of FIGS. 63A-65B.
Figure 66A:
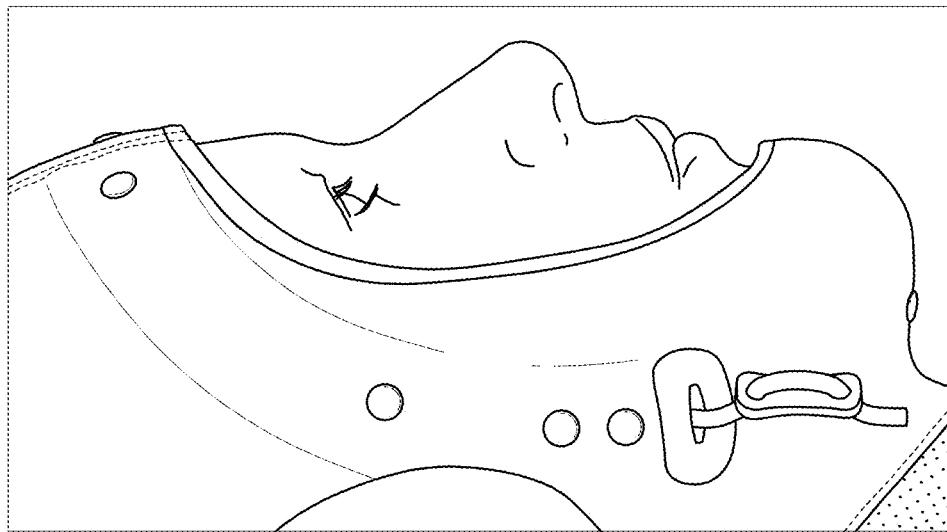

As shown in FIG. 65A, the fastened garment may include an opening at the crown of the head for users with long hair. Openings over the ears (shown in FIG. 65B) may be used for the positioning of the mastoid electrodes just behind the ears, in the correct mastoid area. Moreover, ear cuts may be configured so that the embedded earbuds lean over the ears comfortably. In the examples shown in FIGS. 64A-66B, an elastic band runs over the face outline, hidden in a thermal welded fabric channel. Adjustable mechanisms allow for the user to tighten the elastic band to improve the adherence of the electrodes to the skin. A thermal welded fabric my contour the face opening to improve skin comfort, as shown in FIG. 66B.

On the top of the garment, a light-plastic case may be attached to the fabric with a thermal, welded patch. The case may hold electronics board and it has inlets for the passage of the cables.

A breathable fabric insert, present on both the sides, improves the user's comfort to allow skin transpiration. The garment may be available in different sizes and it is completely washable, even with the embedded electronics.

Figure 67A:
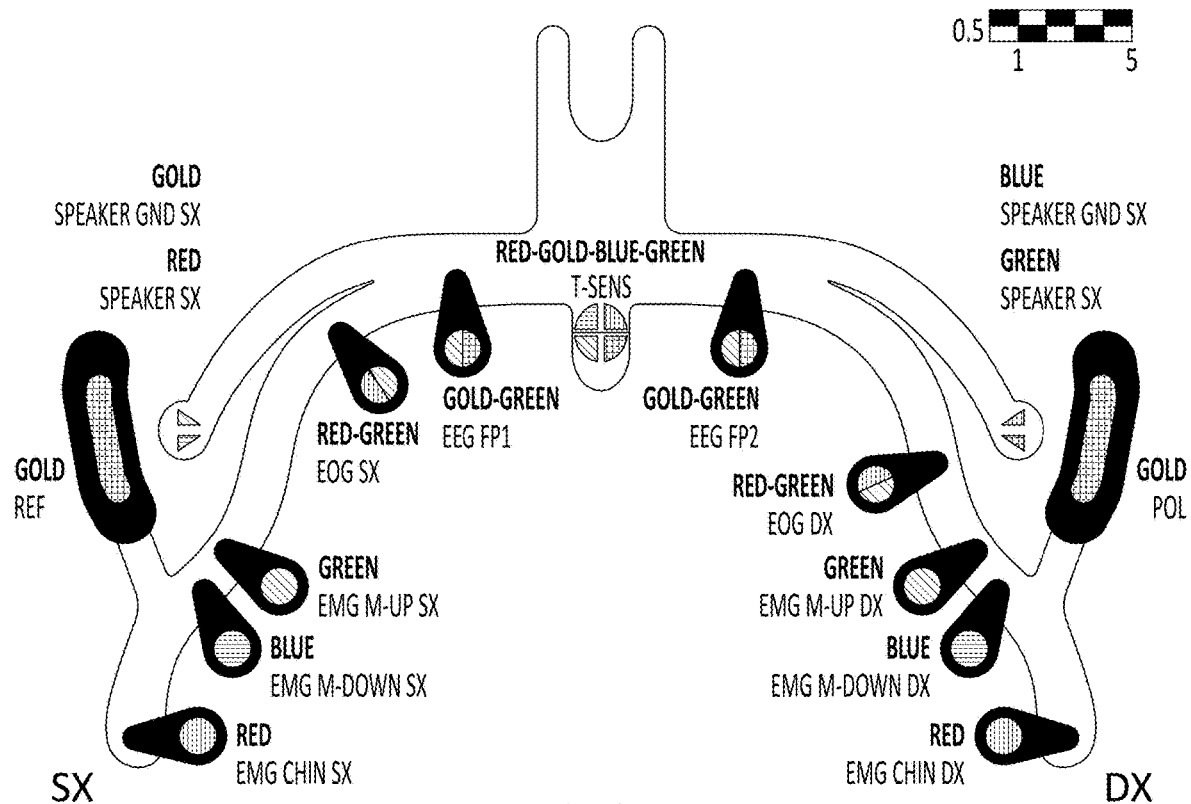
FIG. 67A shows a schematic of the wiring and sensor framework similar to that shown in FIG. 62A-62B.
Figure 67B:
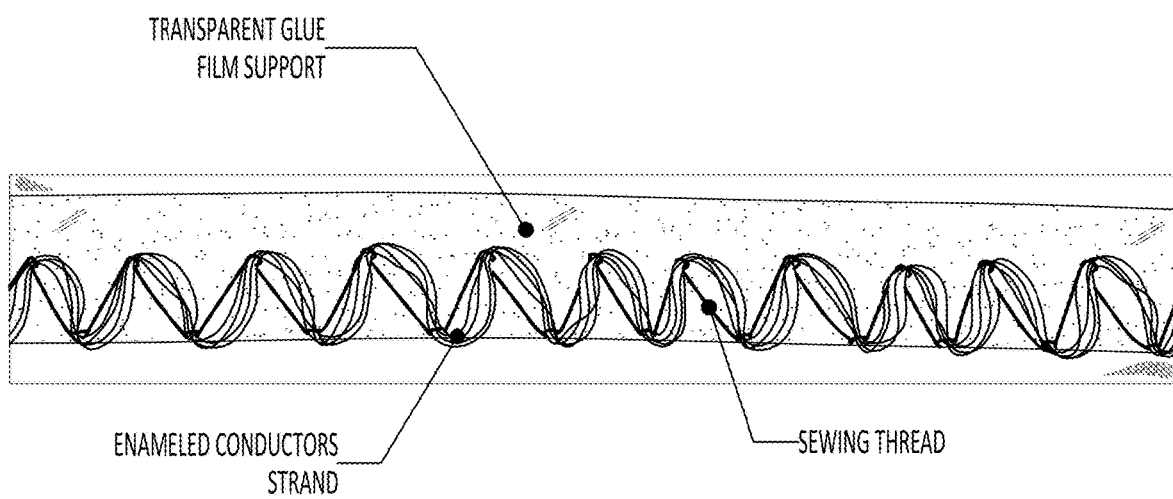
FIG. 67B illustrates a strip of electrical connector adhesive that may be used to form the balaclava devices described herein in which a bundle of insulated wires is sewn (using a sewing thread, as shown) onto a flexible strip of transparent glue film support.

FIG. 67A illustrates one possible layout of a balaclava apparatus, including various sensors/electrodes (labeled by color, red, gold, blue, green) that may be used. In FIG. 67B, an example of a ribbon connector including a zig-zag pattern of insulated wires that are stitched into the transparent glue film support are shown. In this example, the ribbon is a narrow support band (approximately 15 mm instead of 30 mm shown in examples above), and it includes only a glue film instead of glue and fabric. This configuration is simple to bend horizontally for angled paths needed.

Figure 68:
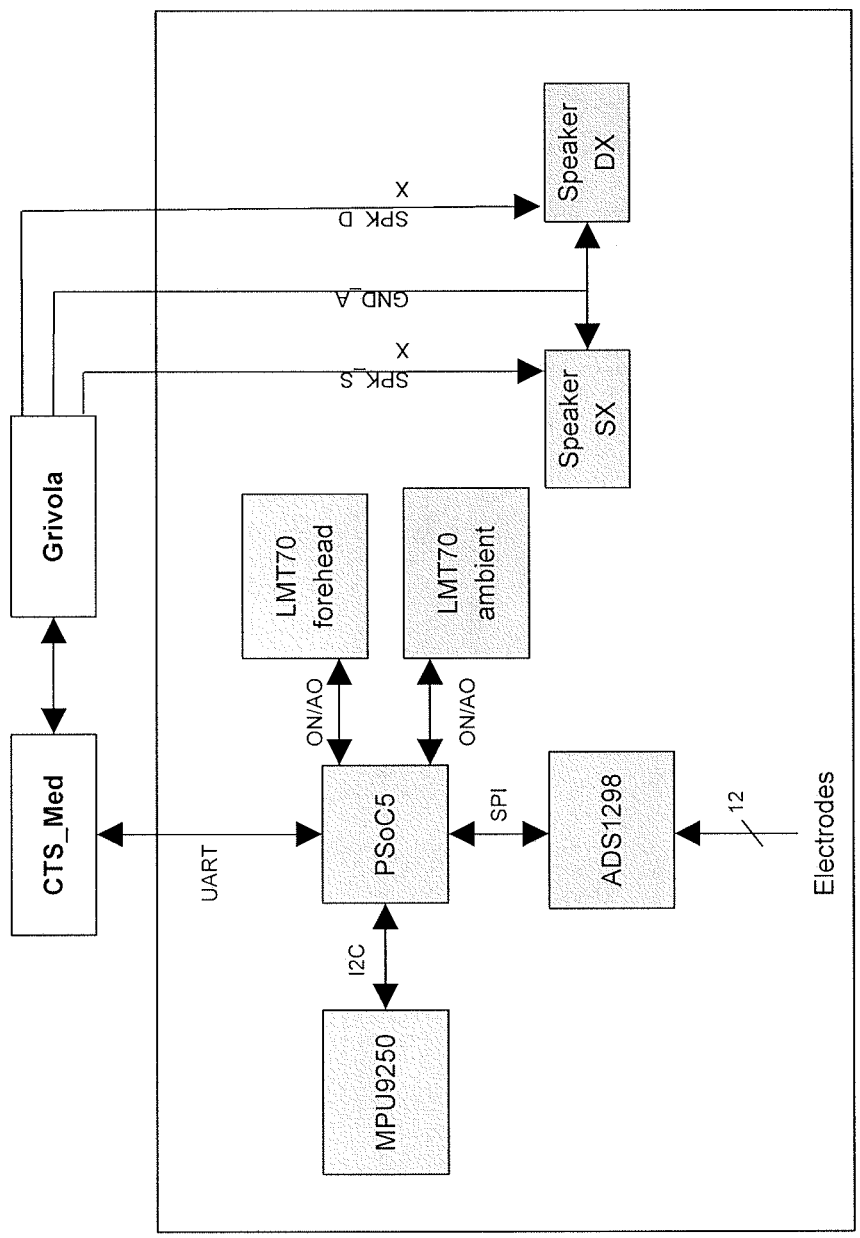
FIG. 68 is a schematic diagram of the components that may be included in a balaclava device such as the ones shown in FIGS. 63A-67B.

In general, the balaclava apparatus may include a set of dry electrodes and sensors for the acquisition of biometric signals, electronics for sensors management, a pair of earbuds and anti-shock circuitry to manage sound experience, a 5-poles jacketed cable to connect the device to L.I.F.E. CTS-Med: biometric data streaming, and a 4-poles jacketed cable to connect the device to Grivola: audio streaming. FIG. 68 illustrates one example of a qualitative schema involving the hardware components. In this example, the PSoC5 (Cypress) is a microcontroller which manages sensors sampling and data transfer to Master device (Grivola). The ADS1298 (Texas Instruments) is an analog-front-end for the digitalization of the analog signals from electrodes. MPU9250 (TDK) is an IMU. The LMT70 forehead (Texas Instruments) is a sensor for user's forehead temperature monitoring. The LMT70 ambient (Texas Instruments) is a sensor for ambient temperature monitoring. The Speaker SX, speaker DX are earbuds. The electronic board may be held into a soft-plastic case on the top of the garment. Cables from the "Ultra light Zig-Zag Band" (e.g., FIGS. 62A-62B and 67B), which wire the electrodes, may be soldered on board pads as well as both the 4-poles and the 5-poles jacketed cables; Potting cover is spread on the board in order to provide mechanical protection and waterproof properties. Firmware may be used to implement sensors sampling and data transfer to the Master device (Grivola) on data-request messages. In some variations a smartphone App (applications software) may provide a user interface for the management of polysomnographic monitoring and audio streaming. A web App may include a set of algorithms for off-line signal processing which yields polysomnographic indices.

Figure 69A:
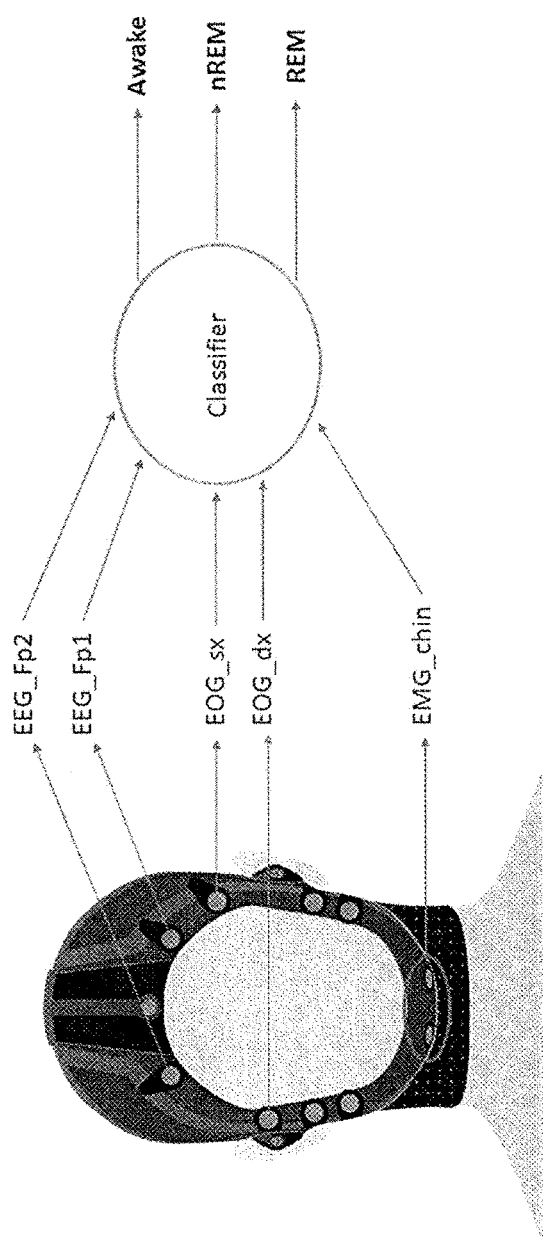
FIG. 69A illustrates a balaclava configured to acquire and relay biometric signals from a user that may be used for monitoring sleep (e.g., sleep staging). The balaclava may be configured to detect EEG and/or EMG, as illustrated and may include a processor configured as a classifier to detect awake/nREM sleep/REM sleep, etc. (alternatively, the processor may be separate from the device and data transmitted to the remote processor).
Figure 69B:
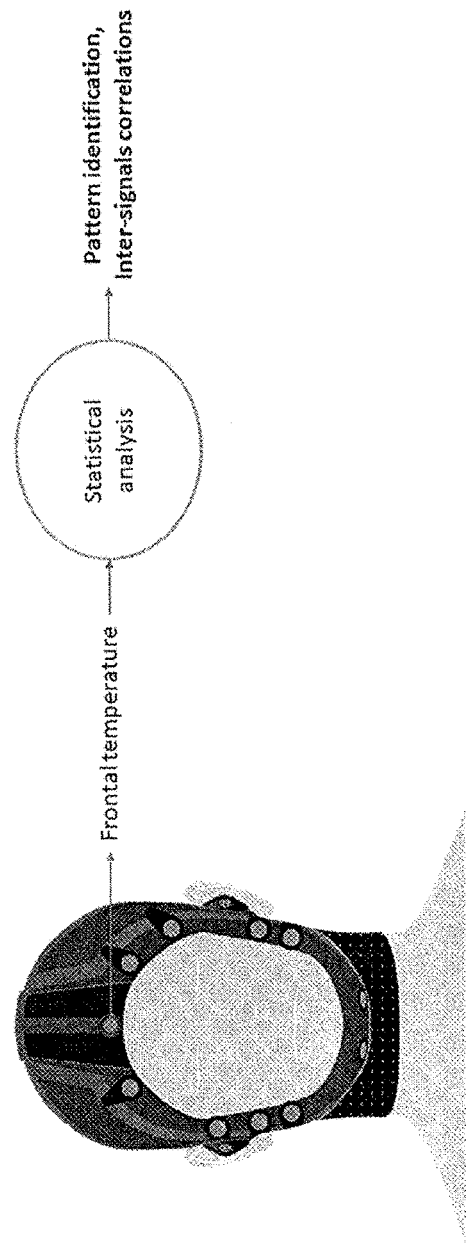
FIG. 69B illustrates a balaclava configured to acquire and relay biometric signals from a user that may be used for monitoring mandibular muscle activity supports the diagnosis of bruxism. Thus, this balaclava is configured to monitor jaw movement (e.g., during sleep) and/or detect bruxism.
Figure 69C:
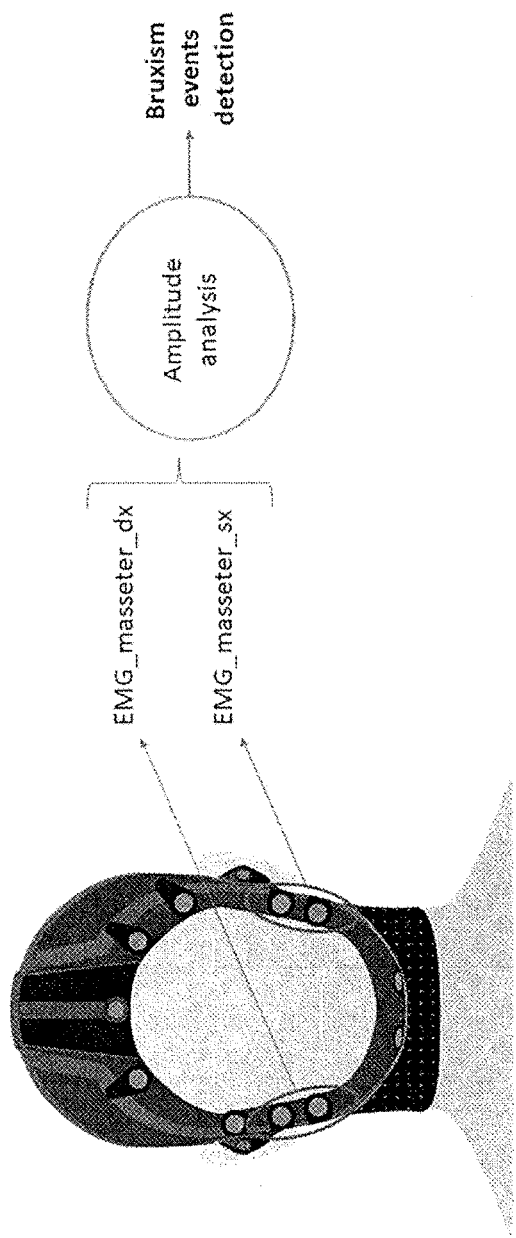
FIG. 69C illustrates a balaclava configured to acquire and relay biometric signals from a user that may be used for monitoring facial/head temperature as well as the bedroom's ambient temperature, which may be helpful for monitoring sleep.
Figure 69D:
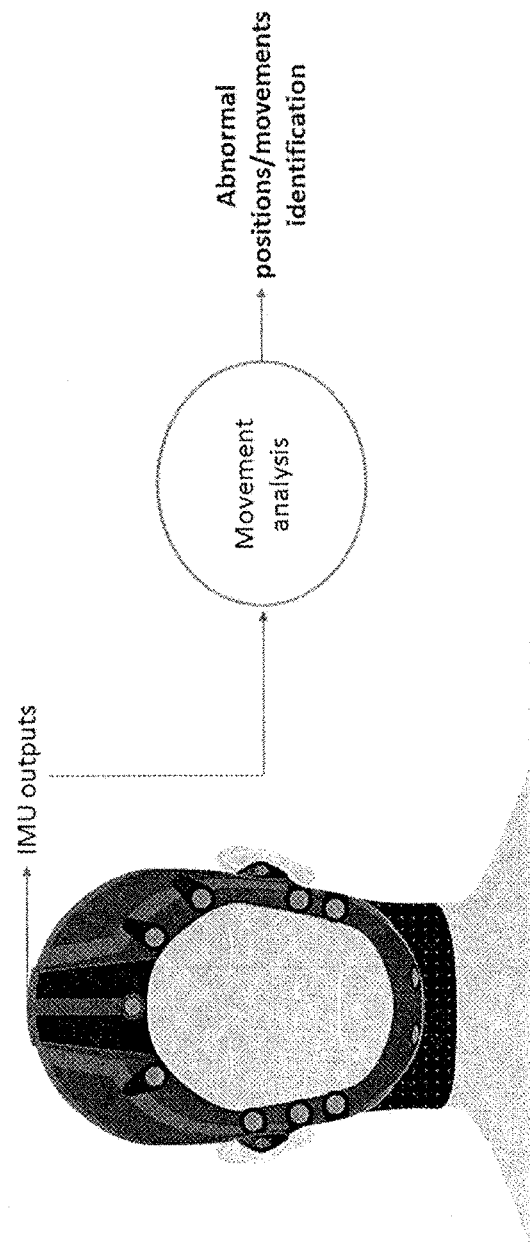
FIG. 69D illustrates a balaclava configured to acquire and relay biometric signals from a user that may be used for monitoring position and movements of the head (e.g., during sleep). The separately configurations of FIGS. 69A-69D may be combined in any combination to provide a head-monitoring device that may be worn, in particular, during sleep.

The user's experience may involve a multiparametric monitoring during sleep, followed by an off-line analysis of the acquired signals which produces a sleep report. The device may, for example, be part of an asset (do you mean 'a set') which implements a complete polysomnography. In some variations, the user wears both a monitoring garment (such as those shown and described above, including the shirts e.g., FIG. 61), and the Balaclava. They plug the Balaclava connectors to CTS_Med and to the Grivola. Then they go to bed and start a polysomnography recording through the proper App in their smartphone. They are allowed to select one or more of the following functions: (1) Sleep staging (using a configuration as shown in FIG. 69A, e.g., relying on the acquired biometric signals, a sleep staging report is performed. Signal parameters drive a classification into "awake", "nREM sleep" and "REM sleep" classes); Bruxism detection (using a configuration as shown in FIG. 69B, e.g., seamless monitoring of mandibular muscle activity supports the diagnosis of bruxism); (3) temperature monitoring; and/or (4) head position monitoring. The user's frontal temperature as well as the bedroom's ambient temperature are both monitored in order to study the temperature trends, patterns and correlations during sleep, as shown in the configuration of FIG. 69C. As shown in FIG. 69D, in the Head position/movements monitoring configuration, information about position and movements of the head during sleep is acquired in order to identify possible, unconscious abnormal positions/movements during sleep. An additional mode or function may include (5) Audio streaming. The garment-embedded earbuds may provide, if requested by the user, music or acoustic stimulation as a sleep aid.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wiring and sensor subsystem comprising a plurality of elastic electrical connector devices, each device comprising:
   an elongate strip of fabric substrate having a first side and a second side;
   a plurality of wires extending along a length of the first side of the elongate strip of fabric substrate in a sinusoidal or zig-zag pattern, wherein each of the plurality of wires is electrically insulated, and wherein the plurality of wires are slideably attached to the first side by a stitch with a thread through the elongate strip of fabric substrate at a plurality of peaks and troughs of the sinusoidal or zig-zag pattern; and
   an adhesive coating on the first side.

2. The subsystem of claim 1, wherein a first end of each of the plurality of elastic electrical connector devices is connected to a controller/processor.

3. The subsystem of claim 1, wherein each elastic electrical connector device has a maximum thickness of less than 2 mm.

4. The subsystem of claim 1, wherein the plurality of wires of each device comprises a bundle of wires twisted together.

5. The subsystem of claim 1, wherein each of the plurality of wires of each device is individually coded along its outer length.

6. The subsystem of claim 1, wherein each of the plurality of wires of each device is electrically insulated with a thermoremovable insulator.

7. The subsystem of claim 1, wherein each of the plurality of wires of each device comprises a copper wire electrically insulated with a polyurethane material.

8. The subsystem of claim 1, wherein the sinusoidal or zig-zag pattern has an amplitude from 0.5 mm to 15 mm.

9. The subsystem of claim 1, wherein a length between peak and trough stitches is between 1 mm and 15 mm.

10. The subsystem of claim 1, wherein the adhesive coating has a thickness of between 10 and 200 micrometers thick.

11. The subsystem of claim 1, wherein the adhesive coating comprises a hot melt film having a melting point of between 130 C and 200° C.

12. The subsystem of claim 1, wherein the plurality of wires comprises between 2 and 10 wires.

13. The subsystem of claim 1, wherein the elongate strip of fabric substrate comprises a stretchable fabric substrate.

14. The subsystem of claim 1, wherein the elongate strip of fabric substrate is between 0.6 mm and 3 cm wide and greater than 10 cm long.

15. The subsystem of claim 1, further comprising a removable backing on the first side covering the adhesive coating.

16. The subsystem of claim 1, wherein the plurality of wires may slide relative to the elongate strip of fabric substrate within the stitch of thread at the plurality of peaks and troughs.

17. A wiring and sensor subsystem comprising a plurality of elastic electrical connector devices, each device comprising:
   an elongate strip of fabric substrate having a first side with a length;
   a bundle of wires that are twisted together extending along the length of the first side of the elongate strip of fabric substrate in a sinusoidal or zig-zag pattern, wherein each of the bundle of wires is electrically insulated with a thermoremovable insulator, and wherein the bundle of wires are slideably attached to the first side by a stitch with a thread material through the elongate strip, wherein the length between peak and trough stitches is between 1 mm and 15 mm; and
   an adhesive coating on the first side, wherein the plurality of elastic electrical connector devices comprises a branching framework of strips that are connected to a controller/processor at a first end of each of the plurality of elastic electrical connector devices.

18. The wiring and sensor subsystem of claim 17, wherein the branching framework of strips is connected to the controller/processor via a sensor management system (SMS) connector.

19. A wiring and sensor subsystem comprising a plurality of elastic electrical connector devices, each device comprising:
   an elongate strip of fabric substrate having a first side and a second side;
   a plurality of wires extending along a length of the first side of the elongate strip of fabric substrate in a sinusoidal or zig-zag pattern, wherein each of the plurality of wires is electrically insulated, and wherein the plurality of wires are slideably attached to the first side by a stitch with a thread through the elongate strip of fabric substrate; and
   an adhesive coating on the first side, wherein a first end of each of the plurality of elastic electrical connector devices is connected to a controller/processor and a second end of each of the plurality of elastic electrical connector devices is configured to be connectable to at least one electronic component.

20. The wiring and sensor subsystem of claim 19, wherein the second end of at least one of the plurality of elastic electrical connector devices is connected to at least one sensor.

* * * * *